US008349850B2

(12) United States Patent
Tworowski et al.

(10) Patent No.: US 8,349,850 B2
(45) Date of Patent: Jan. 8, 2013

(54) HETEROCYCLIC COMPOUNDS AND USES THEREOF IN THE TREATMENT OF SEXUAL DISORDERS

(75) Inventors: Dmitry Tworowski, Rechovot (IL); Ron Matsievitch, Natania (IL); Vladimir Kogan, Rechovot (IL)

(73) Assignee: ATIR Holding S.A., Luxembourg (LU)

( * ) Notice: Subject to any disclaimer, the term of this patent is extended or adjusted under 35 U.S.C. 154(b) by 0 days.

(21) Appl. No.: 11/922,913

(22) PCT Filed: Mar. 28, 2007
(Under 37 CFR 1.47)

(86) PCT No.: PCT/IL2007/000404
§ 371 (c)(1),
(2), (4) Date: Jun. 11, 2009

(87) PCT Pub. No.: WO2007/110868
PCT Pub. Date: Oct. 4, 2007

(65) Prior Publication Data
US 2010/0029671 A1 Feb. 4, 2010

Related U.S. Application Data

(60) Provisional application No. 60/879,531, filed on Jan. 10, 2007, provisional application No. 60/786,379, filed on Mar. 28, 2006.

(51) Int. Cl.
*A61K 31/517* (2006.01)
(52) U.S. Cl. .................. 514/266.2; 514/266.3; 544/284; 544/287
(58) Field of Classification Search .................. 544/284, 544/287
See application file for complete search history.

(56) References Cited

U.S. PATENT DOCUMENTS

| | | | |
|---|---|---|---|
| 3,322,756 A | 5/1967 | Ruschig et al. | |
| 3,984,555 A | 10/1976 | Amschler et al. | |
| 4,835,157 A | 5/1989 | Press et al. | |
| 5,945,117 A | 8/1999 | El-Rashidy et al. | |
| 7,151,103 B2 | 12/2006 | Borsini et al. | |
| 2003/0087916 A1 | 5/2003 | Lavielle et al. | |
| 2004/0048853 A1 | 3/2004 | Bergnes | |
| 2004/0077667 A1* | 4/2004 | Matsuoka et al. | ......... 514/266.2 |
| 2010/0216807 A1 | 8/2010 | Kogan | |

FOREIGN PATENT DOCUMENTS

| | | |
|---|---|---|
| EP | 0465254 | 1/1992 |
| EP | 1724267 | 11/2006 |
| WO | WO 94/07869 | 4/1994 |
| WO | WO 96/16657 | 6/1996 |
| WO | WO 98/56792 | 12/1998 |
| WO | WO 00/32590 | 6/2000 |
| WO | WO 00/50417 | 8/2000 |
| WO | WO 02/48117 | 6/2002 |
| WO | WO 2004/018058 | 3/2004 |
| WO | WO 2004/089312 | 10/2004 |
| WO | WO 2004/105700 | 12/2004 |
| WO | WO 2005/005397 | 1/2005 |
| WO | WO 2005/082887 | 9/2005 |
| WO | WO 2007/000404 | 1/2007 |
| WO | WO 2007/011623 | 1/2007 |
| WO | WO 2007/110868 | 10/2007 |
| WO | WO 2008/117269 | 10/2008 |

OTHER PUBLICATIONS

Communication Relating to the Results of the Partial International Search Mar. 19, 2008 From the International Searching Authority Re: Application No. PCT/IL2007/001174.
Communication Relating to the Results of the Partial International Search Report Dated Aug. 7, 2007 From the International Searching Authority Re.: Application No. PCT/IL2007/000404.
International Preliminary Report on Patentability Dated Jul. 29, 2008 From the International Preliminary Examining Authority Re.: Application No. PCT/IL2007/000404.
International Search Report Dated Feb. 21, 2008 From the International Searching Authority Re.: Application No. PCT/IL2007/000404.
International Search Report Dated Oct. 29, 2008 From the International Searching Authority Re.: Application No. PCT/IL2007/001174.
Written Opinion Dated Feb. 21, 2008 From the International Searching Authority Re.: Application No. PCT/IL2007/000404.
Written Opinion Dated Oct. 29, 2008 From the International Searching Authority Re.: Appliation No. PCT/IL2007/001174.
Communication Pursuant to Article 94(3) EPC Dated Aug. 27, 2009 From the European Patent Office Re.: Application No. 07736144.2.
Communication Pursuant to Article 94(3) EPC Dated Feb. 22, 2010 From the European Patent Office Re.: Application No. 07736144.2.
Official Action Dated Mar. 18, 2010 From the US Patent and Trademark Office Re.: U.S. Appl. No. 11/922,913.
Response Dated Dec. 24, 2009 to Communication Pursuant to Article 94(3) EPC of Aug. 27, 2009 From the European Patent Office Re.: Application No. 07736144.2.
Response Dated Jun. 22, 2010 to Communication Pursuant to Article 94(3) EPC of Feb. 22, 2010 From the European Patent Office Re.: Application No. 07736144.2.
Ambinter "Ambinter Stock Screening Collection", Database CHEMCATS, Chemical Abstracts Service, XP-002468185, Order No. From T5926242/ON-T0518-5380/ON, Oct. 2007.

(Continued)

*Primary Examiner* — Brian McDowell

(57) ABSTRACT

Novel heterocyclic compounds having the formula:

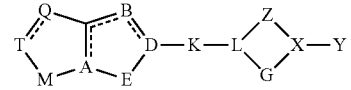

or a pharmaceutically acceptable salt thereof, wherein A, B, D, E, G, K, L, M, Q, T, X, Y and Z are as described in the specification, which exhibit a dopamine receptor (preferably a D4 receptor) agonistic activity, and/or a PDE5 inhibitory activity, are disclosed, as well as processes of preparing same, pharmaceutical compositions containing same and uses thereof in the treatment of sexual disorders such as decreased libido, orgasm disorder and erectile dysfunction.

3 Claims, No Drawings

OTHER PUBLICATIONS

Aurora "Aurora Screening Library", Aurora Fine Chemicals, Database CHEMCATS, Chemical Abstracts Service, Order No. Kenc-0060448, XP-002468184, Sep. 2007.

Communication Relating to the Results of the Partial International Search Dated Aug. 7, 2007 From the International Searching Authority Re.: Application No. PCT/IL2007/000404.

Communication Relating to the Results of the Partial International Search Dated Mar. 19, 2008 From the International Searching Authority Re.: Application No. PCT/IL2007/001174.

International Preliminary Report on Patentability Dated Feb. 16, 2009 From the International Preliminary Examining Authority Re.: Application No. PCT/IL2007/001174.

European Search Report and the European Search Opinion Dated Aug. 20, 2010 From the European Patent Office Re. Application No. 10153226.5.

Gupta et al. "Drugs Acting on the Central Nervous System. Syntheses of Substituted Quinazolones and Quinazolines and Triazepino- and Triazocinoquinazolinones", Journal of Medicinal Chemistry, XP002588388, 11(2): 392-395, 1968. p. 392: Pharmacology, Ex.26.

Communication Pursuant to Article 94(3) EPC Dated Dec. 27, 2010 From the European Patent Office Re.: Application No. 07736144.2.

Response Dated Jun. 29, 2011 to Communication Pursuant to Article 94(3) EPC Dated Mar. 2, 2011 From the European Patent Office Re. Application No. 07827148.3.

Response Dated Apr. 13, 2011 to Communication Pursuant to Article 94(3) EPC of Dec. 27, 2010 From the European Patent Office Re.: Application No. 07736144.2.

Response Dated Apr. 26, 2011 to Communication Pursuant to Article 94(3) EPC of Dec. 27, 2010 From the European Patent Office Re.: Application No. 07736144.2.

Communication Pursuant to Article 94(3) EPC Dated Jun. 6, 2011 From the European Patent Office Re.: Application No. 07736144.2.

Communication Pursuant to Article 94(3) EPC Dated May 23, 2011 From the European Patent Office Re. Application No. 10153226.5.

Response Dated May 16, 2011 to Official Action of Feb. 15, 2011 From the US Patent and Trademark Office Re. U.S. Appl. No. 12/532,869.

Response Dated Mar. 24, 2011 to European Search Report and the European Search Opinion of Aug. 20, 2010 From the European Patent Office Re. Application No. 10153226.5.

Enguehard-Gueiffier et al. "2-[(4-Phenylpiperazin-1-yl)Methyl]Imidazole(Di)Azines as Selective D4-Ligands. Induction of Penile Erection by 2-[4-(2-Methoxyphenyl)Piperazin-1-Ylmethyl]Imidazo[1,2-a]Pyridine (PIP3EA), A Potent and Selective D4 Partial Agonist", Journal of Medicinal Chemistry, 49: 3938-3947, 2006.

Testa et al. "Introduction: Metabolic Hydrolysis and Prodrug Design. Classification, Localization, and Some Physiological Roles of Hydrolytic Enzymes. The Hydrolysis of Carboxylic Acid Esters", Hydrolysis in Drug and Prodrug Metabolism, Helvetica Chimica Acta, Chap.1, 2, 7: 1-46, 370-387, 2003.

Response Dated Sep. 14, 2011 to Communication Pursuant to Article 94(3) EPC of May 23, 2011 From the European Patent Office Re. Application No. 10153226.5.

Response Dated Sep. 26, 2011 to Communication Pursuant to Article 94(3) EPC of Jun. 6, 2011 From the European Patent Office Re.: Application No. 07736144.2.

Response Dated Nov. 3, 2011 to Official Action of Aug. 4, 2011 From the US Patent and Trademark Office Re. U.S. Appl. No. 12/532,869.

Official Action Dated Aug. 4, 2011 From the US Patent and Trademark Office Re. U.S. Appl. No. 12/532,869.

Response Dated Dec. 27, 2011 to Communication Pursuant to Article 94(3) EPC of Oct. 18, 2011 From the European Patent Office Re.: Application No. 07736144.2.

FindLaw "*Eisai Co. Ltd.* v. *Dr. Reddy's Labs., Ltd.*", FindLaw, Nos. 2007-1397, 2007-1398, Jul. 21, 2008.

USPTO, Commerce "Examination Guidelines Update: Developments in the Obviousness Inquiry After *KSR* v. *Teleflex*", Federal Register, 75(169): 53643-53660, Sep. 1, 2010.

Communication Pursuant to Article 94(3) EPC Dated Oct. 18, 2011 From the European Patent Office Re.: Application No. 07736144.2.

Enguehard-Gueiffier et al. "2-[(4-Phenylpiperazin-1-yl)Methyl]Imidazole(Di)Azines as Selective D4-Ligands. Induction of Penile Erection by 2-[4-(2-Methoxyphenyl)Piperazin-1-Ylmethyl]Imidazo[1,2-a]Pyridine (PIP3EA), A Potent and Selective D4 Partial Agonist", Journal of Medicinal Chemistry, 49: 3938-3947, 2006.

Communication Pursuant to Article 94(3) EPC Dated Mar. 2, 2011 From the European Patent Office Re. Application No. 07827148.3.

Official Action Dated Feb. 15, 2011 From the US Patent and Trademark Office Re. U.S. Appl. No. 12/532,869.

Mehta et al. "Synthesis of Substuted Pyrido[3,4-b]Indole-3-Carboxamides and Related Compounds as Benzosiazepine Receptor Agonists/Antagonists", Indian Journal of Chemistry, Section B Organic Chemistry, Including Medicinal Chemistry, 27B(2): 140-143, Feb. 1988.

* cited by examiner

HETEROCYCLIC COMPOUNDS AND USES THEREOF IN THE TREATMENT OF SEXUAL DISORDERS

RELATED APPLICATIONS

This Application is a National Phase of PCT Patent Application No. PCT/IL2007/000404 having International Filing Date of Mar. 28, 2007, which claims the benefit of U.S. Provisional Patent Application Nos. 60/879,531 filed on Jan. 10, 2007; and 60/786,379 filed on Mar. 28, 2006. The contents of the above Applications are all incorporated herein by reference.

FIELD AND BACKGROUND OF THE INVENTION

The present invention relates to the field of pharmacology and, more particularly, to heterocyclic compounds and their use in the treatment of sexual disorders such as decreased libido, orgasm disorder and erectile dysfunction.

Erectile dysfunction (ED), the most common sexual arousal disorder, involves partial or complete failure to attain or maintain a penile erection adequately for intercourse. Erectile dysfunction is a very common problem, affecting from about 40 to 60 percents of men at some time in their life, and about 52 percents of men between 40 and 70 years old.

Penile erection occurs when blood vessels in the penis, particularly in the corpus cavernosum, become filled with large volumes of blood, causing an enlargement and stiffening of the organ. In response to stimuli from the cerebral cortex and/or the parasympathetic nervous system, nitric oxide is released in penile arteries. Nitric oxide causes the smooth muscle in arteries to relax by activating guanylyl cyclase, increasing the concentration of cyclic guanosine monophosphate (cGMP), which activates protein kinase G. The relaxation of the arterial smooth muscle causes the arteries to expand, increasing the volume of blood flowing through the arteries. The increased volume of blood entering the penis leads to an erection. In women, clitoral erection is caused by an analogous mechanism.

The biological effect of nitric oxide is limited by phosphodiesterases (PDEs) which hydrolyze cGMP. Inhibition of PDEs increases the levels of cGMP induced by nitric oxide, thereby magnifying the effects of nitric oxide. Eleven families of phosphodiesterase are known, and their effects depend on their distribution in the body and on their relative specificity for cGMP and/or cyclic adenosine monophosphate (cAMP). cAMP is a compound related to cGMP, which is known to affect many biological processes, including regulation of metabolism and blood flow, by activating protein kinase A.

For instance, PDE3 and PDE4 selectively hydrolyze cAMP (Beavo, 1998). However, while inhibition of these enzymes may prevent erectile dysfunction (Steers, 2002), it also leads to serious adverse side effects, such as enhanced myocardial contraction and heart rate and depression of systemic blood pressure (Andrews and Cowley, 1993).

In contrast, PDE5 is specific for cGMP, which affects fewer biological processes than does cAMP, and is located prominently in the penis. PDE5, first purified and characterized from rat (Francis and Corbin, 1988), is very abundant in vascular smooth muscle cells and appears to play a significant role in modulating smooth muscle tone in general and penile corpus cavernosal smooth muscle tone in particular (Beavo, 1998; Moreland and Goldstein, 1995). Selective inhibitors of PDE5 have therefore been suggested for inducing penile (and clitoral) erection by raising cGMP levels (Terret et al., 1996). It should be noted, however, that elevating cGMP levels would fail to lead to an erection in the absence of production of cGMP in response to a stimulus.

The principal currently available drugs belonging to the PDE5 inhibitors family are tadalafil (Cialis™), vardenafil (Levitra™) and sildenafil (Viagra™), the most famous one being Viagra™ (sildenafil).

Sildenafil was the first selective orally-administered PDE5 inhibitor for treating erectile dysfunction. Vardenafil has a structure very similar to that of sildenafil. Tadalafil contains a methylenedioxyphenyl moiety and is structurally different (Corbin et al., 2002). The chemical structures of these compounds are presented in Scheme 1 below.

Patients suffering from erectile dysfunction generally respond well to medications of the phosphodiesterase type 5 (PDE5) inhibitors family, with approximately 80% success rates (Evans et al., 1980; Hyttel, 1982).

In addition to erectile dysfunction patients, it has been found that many consumers of PDE5 inhibitors are physically healthy men, with no pathological sexual problem, who are aiming to improve the quality of their sexual performance by enhancing extent and duration of erection.

Although sildenafil is considered a selective inhibitor of PDE5, it has long been recognized that it effects on other body organs and hence its use is associated with several adverse side effects such as nausea, headache, and cutaneous flushing. These clinically significant adverse effects are thought to be due to nonspecific inhibition of other PDEs exhibited by this compound (Beavo, 1998; Moreland and Goldstein, 1995).

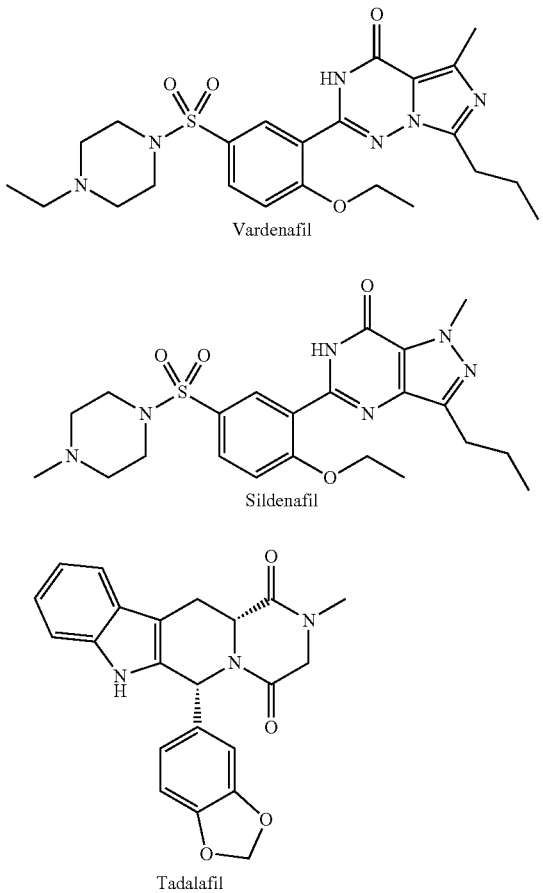

Scheme 1

Vardenafil

Sildenafil

Tadalafil

It has therefore been recognized that an improved, second generation of PDE5 inhibitors would be one with greater potency and specificity for PDE5, resulting in potentially fewer PDE-associated side effects and greater efficacy in the treatment of erectile dysfunction. To this end, several types of nitrogen-containing heterocyclic scaffolds such as quinazoline (Takase et al., 1994; Takase et al., 1994), pyrazolo-pyrimidine (Terret et al., 1993; Dumaitre, Dodic, 1996), isoquinoline (Ukida, 2001), phthalazine (Watanabe, 2000), and naphthalene (Ukida, 1999) derivatives have been synthesized. Some of these compounds have been identified as being potent and selective PDE5 inhibitors (Rotella D P, 2002)

In addition to PDE5, experimental data indicate that several neurotransmitters and neuropeptides in the central nervous system are involved in the control of penile erection and sexual behavior, one such prominent neurotransmitter being dopamine (Melis and Argiolas, 1995; Andersson, 2001). In contrast to PDE5 inhibition, which directly affects the blood vessels in the penis, dopamine is involved in the regulation of penile activity by the central nervous system.

Dopamine is one of the key mediators in the CNS and is involved in a variety of physiological functions, including sexual behavior, cognition, motor coordination, cardiovascular control, reward and hormonal regulation. Dopamine receptors in mammalian tissues have been classified as D1-like (D1 and D5) and D2-like (D2, D3, and D4) (Missale, 1998). It has been shown that several dopamine receptor agonists such as apomorphine, quinpirole, quinelorane, and (−)-3-(3-hydroxyphenyl)-N-n-propylpiperidine (3-PPP) induce penile erection after systemic administration in mammals (Melis and Argiolas, 1995).

Recent demonstration that apomorphine can facilitate penile erection in erectile dysfunction patients has introduced a new approach to pharmacological correction of erectile dysfunction. It is believed that apomorphine induces penile erection by activating the D4 receptor, although other dopamine receptors may also be involved (Brioni et al., 2004). However, apomorphine is classified as a nonselective agonist because it activates all of the dopamine receptor subtypes (Missale, 1998). It is believed that such non-selectivity is associated with the known emetic action that substantially restricts the practical application of apomorphine. It has therefore been considered desirable to obtain selective D4 agonists.

One selective D4 agonist that was found active in penile erection is ABT-724 (2-[(4-pyridin-2-ylpiperazin-1-yl)methyl]-1H-benzimidazole) (Brioni et al., 2004). Methods of using ABT-724 and related compounds in the treatment of various sexual dysfunctions are disclosed in U.S. Pat. Nos. 7,022,728 and 6,960,589, to Cowart et al. The chemical structures of apomorphine and ABT-724 are presented in Scheme 2 below.

Scheme 2

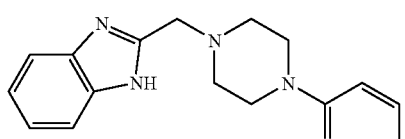

ABT-724

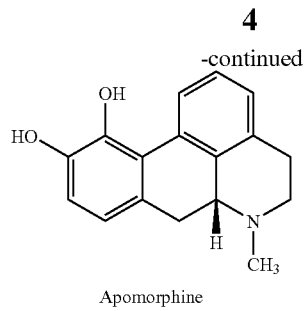

Apomorphine

Other highly selective dopamine receptor D4 agonists have also been developed. These include, for example, PD-168077 and PIP3EA (Melis et al., 2006), A-412997 (Moreland et al., 2005) and A-381393 (Nakane et al., 2005). These compounds are structurally similar to ABT-724, comprising substituted phenyl groups instead of the pyridine group in ABT-724. In addition, PIP3EA comprises 2-imidazo[1,2-a]pyridine instead of the benzoimidazole in ABT-724, A-412997 and PD-168077 comprise a monocyclic aryl group linked by an amide bond instead of benzoimidazole, and A-412997 comprises piperidine instead of piperazine.

In view of the significance of certain types of dopamine receptors in the control of sexual behavior and penile erection, the discovery of ABT-724 (Brioni et al, 2004; Cowart et al, 2004) and development of other highly selective dopamine receptor D4 agonists (Moreland, 2001) have provided a new strategy for the treatment of ED. A further potential advantage for the use of dopamine receptor agonists is the ability of dopamine receptor agonists, selective D4 agonists in particular, to treat a range of sexual disorders.

An example of another type of sexual disorder is the orgasm disorder, in which orgasm and/or ejaculation are absent or delayed to a degree in which sexual satisfaction is significantly reduced, even in the presence of an adequate erection. One common cause of orgasm disorder is selective serotonin reuptake inhibitor (SSRI) therapy.

Dopamine has been found to regulate ejaculation via D2-like receptors (Wolters & Hellstrom, 2006). Bupropion and amantadine, which stimulate dopamine pathways, have been reported to reverse orgasm disorders (Modell et al., 2000; Balon, 1996), and SSRI-induced orgasm disorders are suspected to be induced by inhibition of dopamine pathways (Alcantara, 1999). PDE5 inhibitors have also been found to reverse SSRI-induced orgasm disorders (Ashton, 2004; Damis et al., 1999).

Another example of a type of sexual disorder is decreased libido, or sexual desire disorder, which is often attributed to aging, psychological disorders such as depression, and medications such as SSRIs.

Dopamine release plays an important role in sexual desire, apparently as part of the general role of dopamine in providing motivation for rewarding activities (Giuliano and Allard, 2001). Consequently, dopamine antagonists tend to reduce sexual desire (Stimmel and Gutierrez, 2006). The D4 receptor in particular has been linked to sexual desire, as well as sexual arousal and function (Ben-Zion et al., 2006).

Thus, while the art teaches some PDE5 inhibitors that are useful in the treatment of erectile dysfunction, the use of these compounds is limited by the adverse side effects associated therewith and is further limited to by addressing only a single biological pathway that leads to erectile dysfunction. The art further teaches agents that act via the dopamine pathway, for treating erectile dysfunction and related disorders. The clinical effect of these agents, however, has not been practiced yet.

There is thus a widely recognized need for, and it would be highly advantageous to have novel compounds for treating sexual disorders, devoid of the above limitations.

SUMMARY OF THE INVENTION

The present inventors have now designed and successfully prepared and practiced novel compounds, which are aimed at exhibiting a PDE5 inhibition activity, a D4 agonizing activity or a combination of these activities, and hence can be beneficially used in the treatment of sexual disorders such as decreased libido, orgasm disorder and erectile dysfunction.

According to one aspect of the present invention there is provided a compound having the general Formula I:

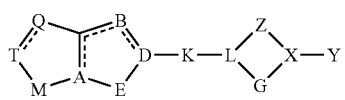

Formula I or a pharmaceutically acceptable salt thereof,
wherein:
the dashed line denotes a saturated or non-saturated bond;
M is —NRb-, —C(=O)—NRb-, —C(=S)—NRb-, or —CRb=CRc-;
Q is N, N⁺Rd, C=O, C=S, or CRd;
T is N, NRa, N⁺Ra, or CRa;
A is N or C;
B is N, NR$_{15}$, CR$_{15}$, O or S;
D is =C—, —CR$_1$—, —CR$_1$—CR$_2$R$_3$—, —C=CR$_2$—, =CR$_1$—N—, =C—NR$_2$—, —CR$_1$—NR$_2$—, —N—CR$_2$R$_3$—, or —C=N—;
E is C=O, C=S, —C(=O)—NR$_4$, —C(=S)—NR$_4$, —CR$_4$=N—, —CR$_4$=N⁺R$_5$—, NR$_4$ or CR$_4$R$_5$;
K is absent or is selected from the group consisting of alkyl, aryl and heteroaryl, each being independently non-substituted or substituted by alkyl, cycloalkyl, aryl, heteroaryl, carbonyl, hydroxy, alkoxy, alkenyl, alkynyl, nitro, amine, nitrile, isonitrile, halide, S(=O), S(=O)$_2$, and/or NR', whereas R' is hydrogen, alkyl, cycloalkyl, aryl, heteroaryl, carboxy, alkenyl or alkynyl;
L is N, —N⁺=CR''—, —C=CR''—, or —CR''—, whereas R'' is hydrogen, alkyl, cycloalkyl, aryl, heteroaryl, carboxy, alkenyl or alkynyl;
Z is absent or is —CR$_6$R$_7$—, —CR$_6$R$_7$—CR$_8$R$_9$—, or —CR$_6$=CR$_8$—;
G is —CR$_{10}$R$_{11}$—, —CR$_{10}$R$_{11}$—CR$_{12}$R$_{13}$—, or —CR$_{10}$=CR$_{12}$—;
X is N, CR$_{14}$, C, —CR$_{14}$=C— or C=O;
Y is absent or is alkyl, cyanoalkyl, alkenyl, carbonyl, carboxy, oxo, cycloalkyl, heteroalicyclic, aryl or heteroaryl, each being substituted or non-substituted;
R$_6$-R$_{14}$ are each independently selected from the group consisting of hydrogen, alkyl, alkenyl, or cycloalkyl, or, alternatively, two of any of Y and R$_6$-R$_{14}$ form a five- or six-membered alicyclic or aromatic ring; and
Ra-Rd, R$_{15}$ and R$_1$-R$_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted, or, alternatively, any two of Ra-Rd form a five- or six-membered alicyclic or aromatic ring.

According to further features in preferred embodiments of the invention described below, A is C; B is N; D is =C—NR$_2$—; and E is C=O or C=S.

According to still further features in the described preferred embodiments A is C; B is O; D is —C=CR$_2$—, —C=N—, or —CR$_1$—CR$_2$R$_3$—; and E is C=O or C=S.

According to still further features in the described preferred embodiments A is N; B is N; D is —C=CR$_2$—; and E is C=O or C=S.

According to still further features in the described preferred embodiments A is C; B is N; D is =C—; and E is —C(=O)—NR$_4$.

According to still further features in the described preferred embodiments A is C; B is CR$_{15}$; D is =C—; and E is —CR$_4$=N—.

According to still further features in the described preferred embodiments R$_{15}$ is selected from the group consisting of hydroxy, alkoxy, aryloxy, carboxy, sulfate and carbamate.

According to still further features in the described preferred embodiments A is C; B is N; D is =C—; and E is NR$_4$.

According to still further features in the described preferred embodiments M is —CRb=CRd-, T is CRa, and Q is CRd.

According to still further features in the described preferred embodiments M is —C(=O)—NRb- or —C(=S)—NRb-; Q is C=O or C=S; and T is NRa.

According to still further features in the described preferred embodiments M is NRb, T is CRa, Q is CRd, and Rd and Ra are linked such that together they form a substituted or non-substituted aromatic ring.

According to still further features in the described preferred embodiments M is —NRb- and Q is N.

According to still further features in the described preferred embodiments L is N; Z is —CR$_6$R$_7$—CR$_8$R$_9$—; G is —CR$_{10}$R$_{11}$—CR$_{12}$R$_{13}$—; and X is N.

According to still further features in the described preferred embodiments L is N; Z is —CR$_6$R$_7$—; G is —CR$_{10}$R$_{11}$—CR$_{12}$R$_{13}$—; and X is —CR$_{14}$=C—.

According to still further features in the described preferred embodiments L is N; Z is —CR$_6$R$_7$—CR$_8$R$_9$—; G is —CR$_{10}$R$_{11}$—CR$_{12}$R$_{13}$—; and X is CR$_{14}$.

According to still further features in the described preferred embodiments Y and R$_{14}$ together form an aromatic ring.

According to still further features in the described preferred embodiments Y is selected from the group consisting of aryl and heteroaryl.

According to still further features in the described preferred embodiments Y has the general formula II:

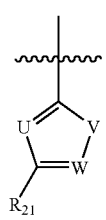

Formula II wherein:
U is CR$_{20}$ or N;
V is —CR$_{24}$=CR$_{23}$—, —N=CR$_{23}$—, S or O;
W is CR$_{22}$ or N; and $R_{20}$-$R_{24}$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

According to still further features in the described preferred embodiments K is methylene.

According to still further features in the described preferred embodiments K is benzyl.

According to still further features in the described preferred embodiments U is $CR_{20}$, W is $CR_{22}$, and V is —$CR_{24}$=$CR_{23}$—.

According to still further features in the described preferred embodiments at least one of $R_{20}$-$R_{24}$ is selected from the group consisting of alkoxy, halide and nitrile.

According to still further features in the described preferred embodiments $R_{20}$ is selected from said group consisting of alkoxy, aryloxy, halide and nitrile; and $R_{21}$-$R_{24}$ are each hydrogen.

According to still further features in the described preferred embodiments the alkoxy is selected from the group consisting of propoxy, ethoxy and methoxy.

According to still further features in the described preferred embodiments the halide is selected from the group consisting of fluoride and chloride.

According to still further features in the described preferred embodiments L is N; Z is —$CR_6R_7$—; G is —$CR_{10}R_{11}$—$CR_{12}R_{13}$; and X is —$CR_{14}$=C—.

According to still further features in the described preferred embodiments Y is attached to the X at a gamma position with respect to L.

According to still further features in the described preferred embodiments Y is phenyl.

According to still further features in the described preferred embodiments U is N.

According to still further features in the described preferred embodiments W is $CR_{22}$ and V is —$CR_{24}$=$CR_{23}$—.

According to still further features in the described preferred embodiments at least one of $R_{21}$-$R_{24}$ is selected from the group consisting of alkoxy and aryloxy.

According to still further features in the described preferred embodiments $R_{24}$ is selected from the group consisting of hydrogen, alkoxy and aryloxy; and $R_{21}$-$R_{23}$ are each hydrogen.

According to still further features in the described preferred embodiments the alkoxy is selected from the group consisting of benzoxy, ethoxy and propoxy.

According to still further features in the described preferred embodiments V is —N=$C_{23}$— and W is $CR_{22}$.

According to still further features in the described preferred embodiments each of $R_{21}$-$R_{23}$ is hydrogen.

According to still further features in the described preferred embodiments V is S and W is $CR_{22}$.

According to still further features in the described preferred embodiments each of $R_{21}$ and $R_{22}$ is hydrogen.

According to still further features in the described preferred embodiments U is $CR_{20}$, W is $CR_{22}$, and V is —$CR_{24}$=$CR_{23}$—.

According to still further features in the described preferred embodiments $R_{21}$ is hydroxy.

According to still further features in the described preferred embodiments each of $R_{20}$ and $R_{22}$-$R_{24}$ is hydrogen.

According to still further features in the described preferred embodiments L is N; Z is —$CR_6R_7$—; G is —$CR_{10}R_{11}$—$CR_{12}R_{13}$—; and X is —$CR_{14}$=C—.

According to still further features in the described preferred embodiments K is methylene.

According to still further features in the described preferred embodiments Y is aryl or heteroaryl.

According to still further features in the described preferred embodiments Y is attached to the X at a beta position with respect to L.

According to still further features in the described preferred embodiments Y is pyridin-2-yl.

According to still further features in the described preferred embodiments M is —CRb=CRd- and Q is CRd.

According to still further features in the described preferred embodiments the compounds described herein is capable of inhibiting an activity of PDE-5.

According to still further features in the described preferred embodiments the compound described herein is characterized as a dopamine receptor agonist, preferably as a selective D4 receptor agonist.

According to still further features in the described preferred embodiments the compound described herein is capable of inhibiting an activity of PDE-5 and is further characterized as a dopamine receptor agonist.

According to another aspect of the present invention there is provided a pharmaceutical composition comprising any of the compounds described herein and a pharmaceutically acceptable carrier.

According to further features in preferred embodiments of the invention described below, the pharmaceutical composition is packaged in a packaging material and identified in print, in or on the packaging material, for use in the treatment of a sexual disorder.

According to still further features in the described preferred embodiments the sexual disorder is selected from the group consisting of erectile dysfunction, an orgasm disorder and a decreased libido.

According to further features in preferred embodiments of the invention described below, the pharmaceutical composition is packaged in a packaging material and identified in print, in or on the packaging material, for use in the treatment of a condition is which inhibiting an activity of PDE-5 is beneficial.

According to further features in preferred embodiments of the invention described below, the pharmaceutical composition is packaged in a packaging material and identified in print, in or on the packaging material, for use in the treatment of a condition in which activating a dopamine receptor is beneficial.

According to further features in preferred embodiments of the invention described below, the pharmaceutical composition is packaged in a packaging material and identified in print, in or on the packaging material, for use in the treatment of a condition is which inhibiting an activity of PDE-5 and activating a dopamine receptor is beneficial.

According to still another aspect of the present invention there is provided a method of treating a sexual disorder, the method comprising administering to a subject in need thereof a therapeutically effective amount of any of the compounds described herein.

According to yet another aspect of the present invention there is provided a use of any of the compounds described herein in the manufacture of a medicament for treating a sexual disorder.

According to an additional aspect of the present invention there is provided a method of inhibiting an activity of PDE-5, the method comprising contacting PDE-5 with an effective amount of any of the compounds described herein.

The contacting can be effected in vitro or in vivo.

According to further features in preferred embodiments of the invention described below, the method is for treating condition in which inhibiting an activity of PDE-5 is beneficial.

According to yet an additional aspect of the present invention there is provided a use of any of the compounds described herein as an inhibitor of an activity of PDE-5 and/or in the manufacture of a medicament for treating a condition in which inhibiting an activity of PDE-5 is beneficial.

According to still an additional aspect of the present invention there is provided a method of activating a dopamine receptor, the method comprising contacting the dopamine receptor with an effective amount of any of the compounds described herein.

The contacting can be effected in vitro or in vivo.

According to further features in preferred embodiments of the invention described below, the method is for treating condition in which activating a dopamine receptor is beneficial.

According to yet a additional aspect of the present invention there is provided a use of any of the compounds described herein as an agonist of a dopamine receptor and/or in the manufacture of a medicament for treating a condition in which activating a dopamine receptor is beneficial.

According to further features in preferred embodiments of the invention described below, the dopamine receptor is a D4 receptor, and the compound is characterized as a selective agonist of the D4 receptor.

According to a further aspect of the present invention there is provided a process of preparing the compound described herein, the process comprising: reacting a compound having the general Formula:

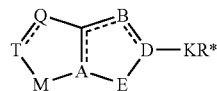

wherein R* is a leaving group, and a compound having the general Formula:

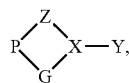

wherein P is selected from the group consisting of NH, —N═CR''—, —CH═CR''— and —CHR''—, thereby obtaining the compound having the general Formula I.

The present invention successfully addresses the shortcomings of the presently known configurations by providing novel heterocyclic compounds which are capable of inhibiting a PDE-5 activity and/or are characterize as dopamine agonists and hence can serve as therapeutic agents for the treatment of sexual disorders which are far superior to the presently used drugs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a", "an" and "the" include plural references unless the context clearly dictates otherwise. For example, the term "a protein" or "at least one protein" may include a plurality of proteins, including mixtures thereof.

As used herein the term "about" refers to ±10%.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein the term "about" refers to ±10%.

DESCRIPTION OF THE PREFERRED EMBODIMENTS

The present invention is of novel heterocyclic compounds, which are designed to exhibit a dopamine receptor (preferably a D4 receptor) agonistic activity, and/or a PDE5 inhibitory activity, and hence can be beneficially utilized in the treatment of sexual disorders such as decreased libido, orgasm disorder and erectile dysfunction.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, PDE5 inhibitors are commonly used to treat erectile dysfunction. In addition, growing evidence suggests that D4 dopamine receptor agonists may also have a role in the treatment and/or prevention of erectile dysfunction, as well as other sexual disorders, such as orgasm disorder and sexual desire disorder.

However, as further discussed hereinabove, current treatment methods are severely limited by side effects such as nausea, headache, and cutaneous flushing in the case of PDE5 inhibitors, and emesis in the case of the non-selective dopamine receptor agonist apomorphine.

While conceiving the present invention, it was envisioned that a novel and effective treatment of sexual disorders could be achieved by the design and preparation of compounds with molecular structures that combine the structural features of selective D4 dopamine receptor agonists with the structural features of PDE5 inhibitors.

It was further envisioned that such compounds, when used to treat erectile dysfunction, would be more effective than either PDE5 inhibitors or D4 receptor agonists, due to their ability to simultaneously promote erection by both PDE5 inhibition and D4 receptor activation. It was further envisioned that simultaneous PDE5 inhibition and D4 receptor activation could potentially result in a synergistic therapeutic effect. It was further envisioned that simultaneous PDE5 inhibition and D4 receptor activation would result in an effective therapy for other, dopamine-related sexual disorders such as decreased libido and orgasm disorders.

As described hereinabove, several selective D4 receptor agonists are known, which feature a piperazine or piperidine moiety which is linked directly to an aryl or substituted aryl group at one end, and linked by a linking group to a monocyclic or bicyclic aryl or heteroaryl moiety at the other end (see, Scheme 2 above).

The molecular structures of the common PDE5 inhibitors, sildenafil, vardenafil, and tadalafil (see, Scheme 1 above), feature a bicyclic heteroaryl moiety and a moiety comprising piperazine or a derivative thereof.

The present inventors have therefore envisioned that the slight similarity between the two existing drug families (PDE5 inhibitors and D4 agonists) can be exploited in the design of molecular structures that would be sufficiently similar to both families so as to exhibit the therapeutic effect of at least one and preferably both drug families and thus would provide an overall solution to sexual disorders, both in term of CNS-regulated therapeutic activity, mediated by dopamine, and actual effect on physiological paths such as an effect on blood vessels, mediated by PDE-5.

While reducing the present invention to practice, a plurality of compounds was designed according to the underlying principles outlined above and readily synthesized. Representative examples of these compounds are presented in Table 1 hereinbelow. As is demonstrated in the Examples section that follows, these compounds were found highly efficacious in inhibiting PDE5 and/or in selectively activating the D4 dopamine receptor, and dual activity was observed among these compounds (see, Table 2).

As used herein, the phrase "dual activity" is meant to describe a property of a compound, whereby the compound exhibits both inhibition of PDE-5 activity and agonism (activation) of D4 dopamine receptor.

The compounds described herein are also referred to herein as heterocyclic compounds and can be collectively represented by the general Formula I:

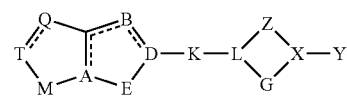

Formula I wherein:
the dashed line denotes a saturated or non-saturated bond;
M is —NRb-, —C(=O)—NRb-, —C(=S)—NRb-, or —CRb=CRc-;
Q is N, N$^+$Rd, C=O, C=S, or CRd;
T is N, NRa, N$^+$Ra, or CRa;
A is N or C;
B is N, NR$_{15}$, CR$_{15}$, O or S;
D is =C—, —CR$_1$—, —CR$_1$—CR$_2$R$_3$—, —C=CR$_2$—, =CR$_1$—N—, =C—NR$_2$—, —CR$_1$—NR$_2$—, —N—CR$_2$R$_3$—, or —C=N—;
E is C=O, C=S, —C(=O)—NR$_4$, —C(=S)—NR$_4$, —CR$_4$=N—, —CR$_4$=N$^+$R$_5$—, NR$_4$ or CR$_4$R$_5$;
K is absent or is selected from the group consisting of alkyl, aryl and heteroaryl, each being independently non-substituted or substituted by alkyl, cycloalkyl, aryl, heteroaryl, carbonyl, hydroxy, alkoxy, alkenyl, alkynyl, nitro, amine, nitrile, isonitrile, halide, S(=O), S(=O)$_2$, and/or NR', where R' is hydrogen, alkyl, cycloalkyl, aryl, heteroaryl, carboxy, alkenyl or alkynyl;
L is N, —N$^+$=CR"—, —C=CR"—, or —CR"—, whereas R" is hydrogen, alkyl, cycloalkyl, aryl, heteroaryl, carboxy, alkenyl or alkynyl;
Z is absent or is —CR$_6$R$_7$—, —CR$_6$R$_7$—CR$_8$R$_9$—, or —CR$_6$=CR$_8$—;
G is —CR$_{10}$R$_{11}$—, —CR$_{10}$R$_{11}$—CR$_{12}$R$_{13}$—, or —CR$_{10}$=CR$_{12}$—;
X is N, CR$_{14}$, C, —CR$_{14}$=C— or C=O;
Y is absent or is alkyl, cyanoalkyl, alkenyl, carbonyl, carboxy, oxo, cycloalkyl, heteroalicyclic, aryl or heteroaryl, each being substituted or non-substituted;
R$_6$-R$_{14}$ are each independently selected from the group consisting of hydrogen, alkyl, alkenyl, or cycloalkyl, or, alternatively, two of any of Y and R$_6$-R$_{14}$ form a five- or six-membered alicyclic or aromatic ring; and
Ra-Rd, R$_{15}$ and R$_1$-R$_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted, or, alternatively, any two of Ra-Rd form a five- or six-membered alicyclic or aromatic ring.

It will be appreciated by one of skills in the art that the feasibility of each of the substituents (Ra-Rd, R', R" and R$_1$-R$_{24}$) to be located at the indicated positions depends on the valency and chemical compatibility of the substituent, the substituted position and other substituents. Hence, the present invention is aimed at encompassing all the feasible substituents for any position.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

As used herein, the term "amine" describes both a —NRxRy group and a —NRx- group, wherein Rx and Ry are each independently hydrogen, alkyl, cycloalkyl, aryl, as these terms are defined herein.

The amine group can therefore be a primary amine, where both Rx and Ry are hydrogen, a secondary amine, where Rx is hydrogen and Ry is alkyl, cycloalkyl or aryl, or a tertiary amine, where each of R' and R" is independently alkyl, cycloalkyl or aryl.

Alternatively, Rx and Ry can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine.

The term "halide" and "halo" describes fluorine, chlorine, bromine or iodine.

The term "haloalkyl" describes an alkyl group as defined above, further substituted by one or more halide(s). Accordingly, the term "trihaloalkyl" describes an alkyl group, as defined above, further substituted by three halides.

The term "sulfate" describes a —O—S(=O)$_2$—ORx end group, as this term is defined hereinabove, or an —O—S(=O)$_2$—O— linking group, as these phrases are defined hereinabove, where $R_X$ is as defined hereinabove.

The term "thiosulfate" describes a —O—S(=S)(=O)—ORx end group or a —O—S(=S)(=O)—O— linking group, as these phrases are defined hereinabove, where Rx is as defined hereinabove.

The term "sulfite" describes an —O—S(=O)—O-Rx end group or a —O—S(=O)—O— group linking group, as these phrases are defined hereinabove, where $R_X$ is as defined hereinabove.

The term "thiosulfite" describes a —O—S(=S)—O-Rx end group or an —O—S(=S)—O— group linking group, as these phrases are defined hereinabove, where $R_X$ is as defined hereinabove.

The term "sulfinate" describes a —S(=O)—ORx end group or an —S(=O)—O— group linking group, as these phrases are defined hereinabove, where $R_X$ is as defined hereinabove.

The term "sulfoxide" or "sulfinyl" describes a —S(=O)Rx end group or an —S(=O)— linking group, as these phrases are defined hereinabove, where Rx is as defined hereinabove.

The term "sulfonate" or "sulfonyl" describes a —S(=O)$_2$—Rx end group or an —S(=O)$_2$— linking group, as these phrases are defined hereinabove, where Rx is as defined herein.

The term "sulfonimade", as used herein, encompasses both S-sulfonamides and N-sulfonamides.

The term "S-sulfonamide" describes a —S(=O)$_2$—NRxR$_Y$ end group or a —S(=O)$_2$—NRx- linking group, as these phrases are defined hereinabove, with Rx and R$_Y$ as defined herein.

The term "N-sulfonamide" describes an RxS(=O)$_2$—NR$_Y$— end group or a —S(=O)$_2$—NRx- linking group, as these phrases are defined hereinabove, where Rx and R$_Y$ are as defined herein.

The term "disulfide" refers to a —S—SRx end group or a —S—S— linking group, as these phrases are defined hereinabove, where Rx is as defined herein.

The term "carbonyl" or "carbonate" as used herein, describes a —C(=O)—Rx end group or a —C(=O)— linking group, as these phrases are defined hereinabove, with Rx as defined herein.

The term "thiocarbonyl" as used herein, describes a —C(=S)—Rx end group or a —C(=S)— linking group, as these phrases are defined hereinabove, with Rx as defined herein.

The term "oxo", as used herein, describes an =O end group.

The term "oxime" describes a =N—OH end group or a =N—O— linking group, as these phrases are defined hereinabove.

The terms "hydroxy" and "hydroxyl" describe a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "ether" describes groups in which a carbon atom in an alkyl, cycloalkyl, aryl or heteroaryl is attached to an alkoxy or aryloxy group.

The term "thioether" describes groups in which a carbon atom in an alkyl, cycloalkyl, aryl or heteroaryl is attached to a thioalkoxy or thioaryloxy group.

The terms "cyano" and "nitrile" describe a —C≡N group.

The term "isonitrile" describes a —N≡C group.

The term "isocyanate" describes an —N=C=O group.

The term "nitro" describes an —NO$_2$ group.

The term "acyl halide" describes a —(C=O) Rz group wherein Rz is halide, as defined hereinabove.

The term "azo" or "diazo" describes an —N=NR' end group or an —N=N— linking group, as these phrases are defined hereinabove, with R' as defined hereinabove.

The term "peroxo" describes an —O—ORx end group or an —O—O— linking group, as these phrases are defined hereinabove, with Rx as defined hereinabove.

The term "carboxy", as used herein, encompasses both C-carboxy and O-carboxy groups.

The term "C-carboxy" describes a —C(=O)—ORx end group or a —C(=O)—O— linking group, as these phrases are defined hereinabove, where Rx is as defined herein.

The term "O-carboxy" describes a —OC(=O)—Rx end group or a —OC(=O)— linking group, as these phrases are defined hereinabove, where R' is as defined herein.

The term "thiocarboxy", as used herein, encompasses both C-thiocarboxy and O-thiocarboxy groups.

The term "C-thiocarboxy" describes a —C(=S)—ORx end group or a —C(=S)—O— linking group, as these phrases are defined hereinabove, where Rx is as defined herein.

The term "O-thiocarboxy" describes a —OC(=S) Rx end group or a —OC(=S)— linking group, as these phrases are defined hereinabove, where Rx is as defined herein.

The term "urea" describes a —NRxC(=O)—NRyRw end group or a —NR$_X$C(=O)—NR$_Y$— linking group, as these phrases are defined hereinabove, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The term "amide", as used herein, encompasses both C-amides and N-amides.

The term "C-amide" describes a —C(=O)—NRxRy end group or a —C(=O)—NRx- linking group, as these phrases are defined hereinabove, where Rx and Ry are as defined herein.

The term "N-amide" describes a RxC(=O)—NRy- end group or a RxC(=O)—N— linking group, as these phrases are defined hereinabove, where Rx and Ry are as defined herein.

The term "carbamyl" or "carbamate", as used herein, encompasses both N-carbamates and O-carbamates.

The term "N-carbamate" describes an RyOC(=O)—NRx- end group or a —OC(=O)—NRx- linking group, as these phrases are defined hereinabove, with Rx and Ry as defined herein.

The term "O-carbamate" describes an —OC(=O)—NRxRy end group or an —OC(=O)—NRx- linking group, as these phrases are defined hereinabove, with Rx and Ry as defined herein.

The term "thiocarbamyl" or "thiocarbamate", as used herein, encompasses both O-thiocarbamates and N-thiocarbamates.

The term "O-thiocarbamate" describes a —OC(=S)—NRxRy end group or a —OC(=S)—NRx- linking group, as these phrases are defined hereinabove, with Rx and Ry as defined herein.

The term "N-thiocarbamate" describes an RyOC(=S) NRx- end group or a —OC(=S)NRx- linking group, as these phrases are defined hereinabove, with Rx and Ry as defined herein.

As used herein, the term "epoxide" describes a

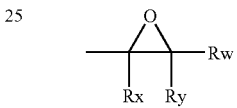

end group or a

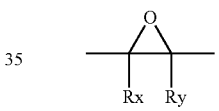

linking group, as these phrases are defined hereinabove, where Rx, Ry and Rw are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, Rq, wherein Rq is defined according to the same definition as Rx.

The term "guanyl" describes a RxRyNC(=N)— end group or a —RxNC(=N)— linking group, as these phrases are defined hereinabove, where Rx and R$_y$ are as defined herein.

The term "nitroso" describes a —O—N=O group.

The term "guanidine" describes a —RxNC(=N)—NRyRw end group or a —RxNC(=N)—NRy- linking group, as these phrases are defined hereinabove, where Rx, Ry and Rw are as defined herein.

The term "hydrazine", as used herein, describes a —NRx-NRyRw end group or a —NR$_x$—NRy- linking group, as these phrases are defined hereinabove, with Rx, Ry, and Rw as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

According to one preferred embodiment of the present invention, each of the compounds described herein is capable of inhibiting an activity of PDE-5.

As used herein, the term PDE-5 encompasses any isoform or conformer of the enzyme phosphodiesterase type 5.

The phrase "inhibiting an activity of PDE-5" describes reducing to some extent, and preferably by 10% or more, an activity of PDE-5, whereby the activity of PDE-5 is preferably a catalytic activity of PDE-5 that leads to hydrolysis of cGMP. Reducing the catalytic activity of PDE-5 (e.g., by 10% or more) is preferably determined by comparing an activity of the enzyme in the presence and absence of a compound as described herein. Preferably the activity of PDE-5 is reduced by at least 20% by the compounds described herein, more preferably by at least 30%, more preferably by at least 40%, more preferably by at least 50%, more preferably by at least 60% and even more preferably by at least 70% and even more.

According to another preferred embodiment of the present invention, each of the compounds described herein is characterized as being a dopamine receptor agonist. Preferably, the dopamine agonist is a selective D4 receptor agonist.

As used herein, the phrase "dopamine receptor" encompasses any subtype of dopamine receptor, including, but not limited to, the D1, D2, D3, D4 and D5 subtypes, except where a specific subtype is referred to. The phrase further encompasses all isoforms and conformers of each subtype.

As used herein, the phrase "D4 receptor" encompasses D4 dopamine receptor, including all isoforms and conformers of thereof.

The term "agonist" with respect to any of the dopamine receptors describes a compound that can act bind the receptor, thus acting as a ligand of the receptor, whereby the binding of the compound to the receptor results in activating the receptor.

The phrase "selective agonist" with respect to D4 receptor, describes a compound that binds to a D4 receptor at higher affinity as compared to other subtypes of dopamine receptors (e.g., D2). Preferably, the selectivity of the D4 receptor agonist is determined by measuring the ratio of its binding to D4 and to D2. Such a ratio is preferably 10:1 or more, and can be, for example, 10:1, 20:1, 50:1, 100:1, 200:1 and even 500:1.

The phrase "activating a dopamine receptor" describes activating a biological pathway that is mediated by the dopamine receptor.

According to further preferred embodiments of the present invention, the compound is both capable of inhibiting an activity of PDE5 and characterized as a dopamine receptor agonist, preferably as a selective D4 receptor agonist.

The compounds described herein, represented by general Formula I above, can be divided into subfamilies according to the chemical nature of their heterocyclic core, represented by the bicyclic moiety on the left side of general Formula I (formed by the variables A, B, D, E, M, Q and T).

In each of the families described hereinbelow, Q, T and M, as defined hereinabove, preferably form a complete conjugation of the pi-electron system in the bicyclic moiety.

Hence, in a preferred embodiment of the present invention, unless specifically described otherwise, each of the compounds described herein is selected such that M is —CRb═CRc-, T is CRa, and Q is CRd, wherein Q and T are linked by a double bond. As mentioned hereinabove, the double bonds present in such a compound (including, but not limited to, the double bonds CRb═CRc and CRd═CRa) are preferably conjugated to a pi-electron system in the other ring of the bicyclic moiety (the ring comprising A-A'-B-D-E) which typically comprises at least one double bond.

In compounds where M is —CRb═CRc-, preferably, CRb is designated herein as the carbon adjacent to T, whereas CRc is designated as the carbon adjacent to A.

As used herein, "A'" refers to the carbon atom in Formula I located between, and bound directly to, A, B and Q.

As used herein, the phrase "bicyclic moiety" refers to the moiety comprising the two fused rings shown in Formula I, which are optionally substituted by Ra-Rd and $R_1$-$R_5$. The bicyclic moiety may be a heteroaryl or a heteroalicyclic. In preferred embodiments, as detailed herein, the bicyclic moiety is heteroaryl.

Thus, in one preferred embodiment of the present invention, the compound of Formula I is selected such that:

A is carbon;
B is nitrogen;
D is ═C—NR$_2$—; and
E is —C(═O)— or —C(═S)—.

Preferably, there is a double bond between A and A', thereby conjugating all the pi-electrons in the bicyclic moiety. The nitrogen atom of D is preferably located adjacent to E, rather than B, such that K in Formula I above is linked to position 2 of the bicyclic moiety. Such compounds are collectively referred to herein interchangeably as compounds of Family 1 or Family 1 compounds. Family 1 compounds are preferably selected such that M is —CRb═CRc-, T is CRa, and Q is CRd. Alternatively, Family 1 compounds are selected such that M is NRb, T is CRa, and Q is NRd.

In another preferred embodiment of the present invention, the compound of Formula I is selected such that:
A is carbon;
B is oxygen;
D is —C═CR$_2$—, —C═N—, or —CR$_1$—CR$_2$R$_3$—; and
E is —C(═O)— or —C(═S)—.

Preferably, there is a double bond between A and A'. The optional nitrogen atom of D (when D is —C═N—) is preferably located adjacent to E, rather than B. Similarly, the C carbon in a —C═CR$_2$— moiety is preferably located adjacent to B and the carbon in CR$_1$ in a —CR$_1$—CR$_2$R$_3$— moiety is preferably located adjacent to B. Thus, K in Formula I above is preferably linked to position 2 of the bicyclic moiety. Such compounds are collectively referred to herein interchangeably as compounds of Family 2 or Family 2 compounds.

In still another preferred embodiment of the present invention, the compound of Formula I is selected such that:
A is nitrogen;
B is nitrogen;
D is —C═CR$_2$—; and
E is —C(═O)— or —C(═S)—.

Preferably there is a double bond between A' and B. Further preferably, the C carbon in a —C═CR$_2$— moiety of D is preferably located adjacent to B, such that K in Formula I above is preferably linked to position 2 of the bicyclic moiety. Such compounds are collectively referred to herein interchangeably as compounds of Family 3 or Family 3 compounds.

In yet another preferred embodiment of the present invention, the compound of Formula I is selected such that:
A is carbon;
B is nitrogen;
D is ═C—; and
E is —NR$_4$—.

Preferably, there is a double bond between A and A'. Such compounds are collectively referred to herein interchangeably as compounds of Family 4 or Family 4 compounds. Family 4 compounds are preferably selected such that K is benzyl or a derivative thereof.

In yet another preferred embodiment of the present invention, the compound of Formula I is selected such that:
A is carbon;
B is nitrogen;
D is ═C—; and
E is —C(═O)—NR$_4$—.

Preferably, there is a double bond between A and A'. Further preferably the carboxyl moiety in E (C═O) is adjacent to D. Such compounds are collectively referred to herein interchangeably as compounds of Family 5 or Family 5 compounds.

In yet another preferred embodiment of the present invention, the compound of Formula I is selected such that:
A is carbon;
B is nitrogen;
D is ═C—;
E is NR$_4$;
M is —C(═O)—NRb-;
Q is C═O; and
T is NRa.

Preferably, there is a double bond between A and A'. M is preferably configured such that the NRb group is adjacent to A, and the carbonyl is adjacent to T. Such compounds are collectively referred to herein interchangeably as compounds of Family 6 or Family 6 compounds.

In still another preferred embodiment of the present invention, the compound of Formula I is selected such that:
A is carbon;
B is CR$_{15}$;
D is ═C—;
E is —CR$_4$═N—;
M is NRb-;
Q is CRd; and
T is CRa;
and Rd and Ra are linked such that together they form an optionally substituted benzene ring.

Preferably, there is a double bond between A and A'. E is preferably configured such that the nitrogen atom is adjacent to D, and the carbon atom is adjacent to A. Such compounds are collectively referred to herein interchangeably as compounds of Family 7 or Family 7 compounds.

In still another preferred embodiment of the present invention, the compound of Formula I is selected such that:
A is carbon;
B is CR$_{15}$;
D is ═C—;
E is —CR$_4$═N—;
and R$_{15}$ is a group comprising an oxygen atom that is directly bound to the B carbon atom. Examples of such groups include, but are not limited to, hydroxy, alkoxy, aryloxy, O-carboxy, O-carbamate and sulfate.

Preferably, there is a double bond between A and A'. E is preferably configured such that the nitrogen atom is adjacent to A, and the carbon atom is adjacent to D. Such compounds are collectively referred to herein interchangeably as compounds of Family 8 or Family 8 compounds. R$_{15}$ is preferably hydroxy.

Alternatively, each of the compounds described herein, and preferably compounds of Family 1, is selected such that M is —NRb-, T is CRa, and Q is nitrogen. As mentioned hereinabove, the conjugated pi-electron system in such a compound (including, but not limited to, the double bond N═CRa and the NRb nitrogen atom) is preferably conjugated to a pi-electron system present in the other ring of the bicyclic moiety (i.e., the ring comprising A-A'-B-D-E) comprising at least one double bond.

Family 1 compounds in which M is —CRb═CRc-, T is CRa, and Q is CRd, have a quinazolin-4(3H)-one bicyclic moiety.

Family 1 compounds in which M is —NRb, T is CRa, and Q is N, have a 1H-purin-6-one bicyclic moiety.

Family 2 compounds in which D is —C═CR$_2$ have a 4H-chromen-4-one bicyclic moiety.

Family 2 compounds in which D is —CR$_1$—CR$_2$R$_3$— have a chroman-4-one bicyclic moiety.

Family 2 compounds in which D is —C═N— have a 4H-benzo[e][1,3]oxazin-4-one bicyclic moiety.

Family 3 compounds have a 4H-pyrido[1,2-a]pyrimidin-4-one bicyclic moiety.

Family 4 compounds have a 1H-benzo[d]imidazole bicyclic moiety.

Family 5 compounds have a 3,4-dihydroquinoxalin-2(1H)-one bicyclic moiety.

Family 6 compounds have a purine-2,6(3H,7H)-dione bicyclic moiety.

Family 7 compounds have a 9H-pyrido[3,4-b]indole (also known as β-carboline) tricyclic moiety, the tricyclic moiety comprising the bicyclic moiety described in Formula I fused with an optional additional ring comprised of Ra and Rd.

Family 8 compounds having a quinolin-4-ol bicyclic moiety.

Preferably, the compound is a Family 1 compound.

As defined in Formula I hereinabove, the bicyclic moiety in each of the compounds described herein may be substituted or non-substituted by Ra-Rd, $R_{15}$, and $R_1$-$R_5$, as defined herein.

Preferably, the bicyclic moiety is a non-substituted bicyclic moiety, such that each of Ra-Rd, $R_{15}$, and $R_1$-$R_5$ is either hydrogen or absent, except for the particular substituents that form part of the bicyclic (or tricyclic) moieties, as for Ra and Rd in Family 7 and $R_{15}$ in Family 8.

Alternatively, at least one of Ra-Rd and $R_1$-$R_5$ is other than hydrogen. As demonstrated in the Examples section that follows (see, Example 9), it has been found that these substituents, and particularly Ra-Rd, may have an effect on the activity of the compound.

Hence, at least one of Ra-Rd is preferably hydrogen, alkyl, hydroxy, alkoxy and halide, and more preferably, Ra-Rd are as follows: Ra is hydrogen or halide (e.g., chloride), short alkyl (e.g., ethyl) or short alkoxy (e.g., methoxy), preferably halide; Rb is hydrogen, short alkyl (e.g., ethyl, propyl, or trifluoromethyl), alkaryl (e.g., benzyl) or alkoxy (e.g., methoxy), preferably hydrogen or alkoxy; Rc is hydrogen, alkoxy, halide or alkyl (e.g., methyl), preferably hydrogen, halide (e.g. fluoride) or alkyl; and Rd is hydrogen or alkyl (e.g., methyl or propyl).

Further preferably, $R_2$ is hydrogen or benzyl; and $R_{15}$ is hydrogen or hydroxy.

As further described hereinabove, the cyclic amine piperazine and related cyclic amines are present in known PDE5 inhibitors and D4 receptor agonists. It is therefore preferable that the ring L-Z—X-G in Formula I constitutes a cyclic amine. As is demonstrated in Table 1, representative compounds comprising a number of types of cyclic amines have been synthesized. The cyclic amine moiety is also referred to herein interchangeably as the "linker" moiety.

As used herein, the phrase "cyclic amine" refers to a cyclic chemical moiety that comprises a ring, wherein one of the atoms of the ring is a nitrogen atom.

Thus in a preferred embodiment of the present invention, the compound of Formula I is selected such that:

L is nitrogen;
Z is —$CR_6R_7$—$CR_8R_9$—;
G is —$CR_{10}R_{11}$—$CR_{12}R_{13}$—; and
X is nitrogen.

In another preferred embodiment of the present invention, the compound of Formula I is selected such that:

L is nitrogen;
Z is —$CR_6R_7$—;
G is —$CR_{10}R_{11}$—$CR_{12}R_{13}$—; and
X is —$CR_{14}$=C—.

In this embodiment, the Y group may be attached to X at either a beta or gamma position with respect to L (namely, the second or third positions, respectively, next to L in the cyclic amine ring). Preferably, Y is attached at a gamma position, such that $CR_{14}$ is linked to Z and Y is attached to the carbon in X that is linked to G.

In still another preferred embodiment of the present invention, the compound of Formula I is selected such that:

L is nitrogen;
Z is —$CR_6R_7$—$CR_8R_9$—;
G is —$CR_{10}R_{11}$—$CR_{12}R_{13}$—; and
X is $CR_{14}$.

In yet another preferred embodiment of the present invention, the compound of Formula I is selected such that:

L is nitrogen;
Z is —$CR_6R_7$—$CR_8R_9$—;
G is —$CR_{10}R_{11}$—$CR_{12}R_{13}$—; and
X is C=O.

In yet another preferred embodiment of the present invention, the compound of Formula I is selected such that:

L is —$N^+$=CR"—;
Z is absent;
G is —$CR_{10}$=$CR_{12}$—; and
X is nitrogen.

The chemical structures of the various preferred cyclic amine groups are illustrated in the Examples section that follows.

As defined in Formula I hereinabove, the cyclic amine in the compounds described herein may be substituted or non-substituted by $R_6$-$R_{14}$, as defined herein.

Preferably, the cyclic amine is a non-substituted cyclic amine, such that each of $R_6$-$R_{14}$ is either hydrogen or absent.

Alternatively, at least one of $R_6$-$R_{14}$ is other than hydrogen. In such cases, preferably, $R_6$-$R_{14}$ are as follows: $R_6$-$R_8$ and $R_{10}$-$R_{11}$ are hydrogen or methyl; $R_9$ and $R_{12}$-$R_{13}$ are hydrogen; $R_{14}$ is hydrogen or hydroxy, or $R_{14}$ is linked with Y to form an aromatic (e.g., benzene ring) that is fused to the cyclic amine.

The cyclic amine moiety in the compounds described herein is preferably linked to the bicyclic moiety described herein via K, as defined hereinabove, which serves as a bridging moiety.

In a preferred embodiment of the present invention, the compound of Formula I is selected such that K is methylene (—$CH_2$—), ethylene (—$CH_2$—$CH_2$—), ethylidene (—CH(—$CH_3$)—), benzyl (—CH($C_6H_5$)—) or a derivative of benzyl. The most preferable benzyl derivative is 4-methoxybenzyl.

K is preferably benzyl or a derivative thereof, most preferably benzyl, in Family 4 compounds, as defined hereinabove, whereas K is preferably methylene in other compounds.

Without being bound to any particular theory, the bridging moiety K is preferably selected so as to allow a conformational freedom for binding to the desired binding sites in both D4 and PDE-5 and hence is expected to act as a spacer that provides a distance between that part of the molecule that binds to certain binding sites at the PDE-5 and that part of the molecule that binds to certain binding sites at the D4 receptor, and further enables these two parts of the molecule to adopt a desired conformation in order to bind to these different types of binding sites.

The cyclic amine moiety in the compounds described herein is preferably linked to a third moiety, denoted "Y" in general Formula I above, and also referred to herein interchangeably as a "tail" moiety.

In a preferred embodiment of the present invention, Y is aryl, heteroaryl, carbonyl, cyclohexyl, allyl or 3-cyanopropyl. Examples of carbonyl groups include, without limitation, acetyl, 2-furoyl, 2-tetrahydrofuran-2-ylcarbonyl, and ethoxycarbonyl.

As described hereinabove, known D4 receptor agonists comprise an aryl or heteroaryl group bound to the abovementioned cyclic amine. Hence, Y is preferably aryl or heteroaryl. Alternatively, Y may be bound to a side group of the cyclic amine moiety, being any of $R_6$-$R_{14}$, preferably $R_{14}$, such that the combination of Y and the side group comprises an aryl that is fused with the cyclic amine ring, whereby the aryl ring and the cyclic amine ring share at least two atoms.

Most preferably, Y is an aryl or heteroaryl, whereby the aryl or heteroaryl has the general formula II:

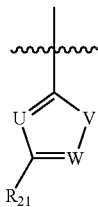

Formula II wherein:
U is $CR_{20}$ or nitrogen;
V is —$CR_{24}$=$CR_{23}$—, —N=$CR_{23}$—, sulfur or oxygen;
W is $CR_{22}$ or nitrogen; and
$R_{20}$-$R_{24}$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

As demonstrated in the Examples section that follows, it has been found that the substituents on the aryl or heteroaryl groups constituting Y may have an effect on the activity of the compound.

Thus, in a preferred embodiment of the present invention, the group Y of Formula II is selected such that U is $CR_{20}$, W is $CR_{22}$, and V is —$CR_{24}$=$CR_{23}$—, that is, Y comprises phenyl or a derivative thereof. Preferably, at least one of $R_{20}$-$R_{24}$ is alkyl, hydroxyl, alkoxy, halide or nitrile. The alkyl is preferably methyl, the alkoxy group is preferably propoxy, ethoxy or methoxy and the halide is preferably fluoride or chloride. More preferably, $R_{20}$ is alkyl, hydroxyl, alkoxy, halide or nitrile and $R_{21}$-$R_{24}$ are hydrogen, or $R_{21}$ is hydroxy. Especially preferable are compounds wherein $R_{21}$ is hydroxy and $R_{20}$ and $R_{22}$-$R_{24}$ are hydrogen, which, as shown in Table 2 hereinbelow exhibit dual activity.

In another preferred embodiment of the present invention, the group Y of Formula II is selected such that U is N, W is $CR_{22}$, and V is —$CR_{24}$=$CR_{23}$—, that is, Y comprises pyridin-2-yl or a derivative thereof. $R_{21}$-$R_{24}$ in such compounds are preferably hydrogen, alkoxy or aryloxy. More preferably, the alkoxy or aryloxy is located at $R_{24}$, at position 3 of the pyridine ring, and $R_{21}$-$R_{23}$ are preferably hydrogen. As demonstrated hereinbelow, such compounds exhibit dual activity. Preferred alkoxy groups are ethoxy and propoxy, while the aryloxy group is preferably benzoxy. In yet another preferred embodiment of the present invention, Y is pyrimidin-2-yl or thiazol-2-yl, or derivatives thereof. Preferably, Y in this embodiment is not substituted.

Each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of the present embodiments, preferably, a pharmaceutically acceptable salt of the compounds described herein is an acid addition salt which includes a cyclic amine, as described herein, in which the amine is in a form of a quaternary ammonium ion, and a counter ion, derived from the selected acid, that forms a pharmaceutically acceptable salt.

Depending on the stoichiometric proportions between the base (the amine) and the acid in the salt, the acid additions salts can be either mono addition salts or poly addition salts.

The phrase "mono addition salt", as used herein, refers to a salt in which the stoichiometric ratio between the acid anion and amine cation is 1:1, such that the acid addition salt includes one molar equivalent of the acid per one molar equivalent of the compound.

The phrase "poly addition salt", as used herein, refers to a salt in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the compound.

The acid addition salts of the compounds described herein are therefore complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono acid addition salt or a poly acid addition salt, as these terms are defined hereinabove, and can further be in a form of a hydrate thereof, as defined hereinbelow.

Further, each of the compounds described herein, including the salts thereof, can be in a form of a prodrug, a solvate or a hydrate thereof.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

As implied hereinabove and is further discussed in more detail in the Examples section that follows, the compounds described herein are preferably selected capable of binding, preferably simultaneously, to pharmacophoric binding sites of a dopamine (D4) receptor and of PDE-5, so as to activate the dopamine receptor while, at the same time, inhibit the activity of PDE-5. As further discussed hereinabove, in order to avoid adverse side effects, it is desirable that the binding of the compounds would be effected selectively to the D4 receptor and to PDE-5.

The compounds described herein are therefore preferably selected so as to have at least one moiety in which at least some, preferably most, of its various functionalities would be in a suitable proximity and orientation to the pharmacophoric binding sites of a D4 receptor, so as to induce activation of the receptor, as defined herein, and hence act as a selective D4 receptor agonist. Thus, for example, it is desired that the cyclic amine moiety would adopt a spatial conformation that would allow it to be present in a desired proximity and orientation to these binding sites, so as to exhibit a strong interaction therewith.

The compounds described herein are preferably further selected so as to have at least one moiety in which at least some, preferably most, of its various functionalities would be in a suitable proximity and orientation to the pharmacophoric binding sites of PDE-5, so as to inhibit the catalytic activity of the enzyme, as defined herein, and hence act as a selective PDE-5 inhibitor. Thus, for example, it is desired that the bicyclic heterocyclic moiety would adopt a spatial conformation that would allow it to be present in a desired proximity and orientation to these binding sites, so as to exhibit a strong interaction therewith.

The compounds described herein are therefore preferably selected so as to comprise at least one moiety that is capable of selectively interacting with the desired binding sites of a D4 receptor that would result in activation thereof and at least one moiety that is capable of selectively interacting with the desired binding sites of a PDE-5 that would result in inhibition of its activity, whereby the compound is designed so as to allow an appropriate proximity and orientation of these moieties with respect to the respective binding sites and thus to allow an interaction of these moieties with these binding sites.

As used herein, the phrase "binding site" describes a specific site in a receptor or in the catalytic domain of an enzyme that includes one or more reactive groups through which the interactions with the substrate, receptor ligand and/or other components can be effected. Typically, the binding site is composed of one or two amino acid residues, whereby the interactions typically involve reactive groups at the side chains of these amino acids.

The interactions of the various functional groups of the compound with the various binding sites of the enzyme or the receptor can be, for example, Van der Waals interactions, electrostatic interactions, hydrogen bonding interactions, hydrophobic interactions, aromatic interactions, π-stacking interactions, and the like, depending on the reactive groups that participate in the interactions and their proximity and orientation to one another.

Exemplary electrostatic interactions include anion-cation interactions and acid-base interactions such as, for example, interactions between ammonium cation and carboxylate anion.

Exemplary hydrogen bonding interactions include interactions between hydrogens of amine, hydroxyl or thiol of one or more component(s) and e.g., oxygen, nitrogen and sulfur atoms of other component(s).

Exemplary hydrophobic interactions include interactions between two or more hydrocarbon moieties such as alkyl, cycloalkyl and aryl.

Exemplary aromatic interactions include interactions between two or more aromatic moieties such as aryls and heteroaryls, which are based on overlap in the aromatized molecular orbitals of the moieties.

Exemplary π-stacking interactions include interactions between two or more moieties that contain π-electrons (e.g., unsaturated moieties), which are based on overlap in the π-orbitals of the moieties.

Being designed capable of inhibiting a catalytic activity of PDE-5 and/or acting as dopamine receptor agonists, the compounds described herein are particularly suitable for use in the treatment of conditions in which these activities are beneficial.

Hence, according to further aspects of the present invention there is provided a method of inhibiting a PDE-5 activity, which is effected by contacting the enzyme with any of the compounds described herein. Further provided is a method of activating a dopamine receptor, particularly a D4 receptor, which is effected by contacting the receptor with any of the compounds described herein. The contacting can be effected in vivo or ex-vivo (in vitro). Further provided are uses of the compounds described herein as agents for inhibiting a PDE-5 activity and/or for activating a D4 receptor.

More importantly, according to another aspect of the present invention, there is provided a method of treating a sexual disorder. The method, according to this aspect of the present invention is effected by administering to a subject in need thereof a therapeutically effective amount, as defined hereinabove, of any of the abovementioned compounds.

In still another aspect of the present invention, there is provided a use of any of the abovementioned compounds, in the manufacture of a medicament for treating a sexual disorder.

As used herein the terms "treating", "treatment" and any grammatical diversion thereof include abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the phrase "sexual disorder", also referred to herein and in the art as "sexual dysfunction" describes a medical condition that is expressed by a difficulty during any stage of the sexual act (which includes desire, arousal, orgasm, and resolution) that prevents the individual or couple from enjoying sexual activity. The medical condition can be associated with a mental malfunction, a physical malfunction and/or can be as a result of a medication, a drug, alcohol, and other external factors.

Sexual disorders are generally classified into the following categories: sexual desire disorders (decreased libido), sexual arousal disorders (e.g., erectile dysfunction), and orgasm disorders (e.g., expressed by delay or absence of orgasm following a normal sexual excitement phase).

The subject is preferably a mammal, more preferably a human.

The methods and uses described herein can optionally be effected by combining the compounds described herein with other agents for treating sexual disorders (e.g., additional active agents that act as PDE-5 inhibitors or D4 agonists), or, alternatively, by combining the compounds described herein with, for example, a drug such as SSRI, which is known to cause a sexual dysfunction, in order to reduce or prevent the adverse effect of the drug in this regard.

In any of the methods and uses described herein, the compounds presented herein, can be utilized either per se, or, preferably as a part of a pharmaceutical composition.

Hence, according to another aspect of the present invention, there are provided pharmaceutical compositions, which comprise one or more of the compounds described above and a pharmaceutically acceptable carrier.

As used herein a "pharmaceutical composition" refers to a preparation of one or more of the compounds described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the abovementioned compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the compounds of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds of the present invention and a suitable powder base such as, but not limited to, lactose or starch.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds of the present invention prepared in water-soluble form. Additionally, suspensions of the compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds to allow for the preparation of highly concentrated solutions.

Alternatively, the compounds of the present invention may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in a therapeutically effective amount for achieving the intended purpose. More specifically, a "therapeutically effective amount" means an amount of one or more of the compounds of the present invention sufficiently effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from activity assays in animals. For example, a dose can be formulated in animal models to achieve a circulating concentration range that has been shown by activity assays to result in both significant D4 receptor binding and/or activation, and significant inhibition of PDE5. Such information can be used to more accurately determine useful doses in humans.

Toxicity and therapeutic efficacy of the compounds described herein can be determined by standard pharmaceutical procedures in experimental animals, e.g., by determining the $EC_{50}$, the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% of the maximal level of D4 receptor activation and/or PDE5 inhibition. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition, as is detailed hereinabove.

Thus, according to an embodiment of the present invention, depending on the selected compound(s), the pharmaceutical compositions of the present invention are packaged in a packaging material and identified in print, in or on the packaging material, for use in the treatment of a condition in which activation of the D4 receptor and inhibition of PDE5 are desirable, as described hereinabove.

In each of the methods, uses and compositions described herein, the compound can optionally be utilized (co-administered or co-formulated) in combination with another active agent.

Such active agents can be, for example, an additional dopamine agonist and/or an additional PDE-5 inhibitor.

Alternatively, the compounds can be utilized in combination with drugs or other agents that are known to cause a sexual disorder as an adverse side effect thereof (e.g., SSRIs), in order to reduce or prevent the sexual dysfunction caused thereby.

Further according to the present invention there are provided processes for preparing the compounds described herein. These processes are generally effected by reacting a compound having the general Formula:

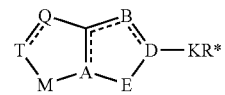

wherein R* is a leaving group,
and a compound having the general Formula:

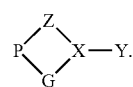

P in the Formula above is selected such that upon the reaction, L, as defined hereinabove, is formed and is linked to K (see, Formula I). Thus, for example, in cases where L is N, P can be, for example, NH. In cases where L —N⁺=CR"—, P can be, for example, —N=CR"—. In cases where L is —C=CR"—, P can be, for example, —CH=CR"—. In cases where L is —CR"—, P can be, for example, —CHR"—.

The reaction is preferably a nucleophilic reaction, and thus, the compound

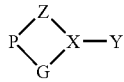

is preferably a nucleophile.

As used herein, and is well known in the art, As used herein, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, halide, acetate, tosylate, triflate, mesylate, sulfonate, azide, hydroxy, thiohydroxy, alkoxy, cyanate, thiocyanate, nitro and cyano. Preferably, the leaving group is selected from halide, acetate, tosylate, triflate, mesylate and sulfonate.

The term "acetate" refers to acetic acid anion.

The term "tosylate" refers to toluene-4-sulfonic acid anion.

The term "triflate" refers to trifluoro-methanesulfonic acid anion.

The term "azide" refers to an $N_3^-$.

The terms "cyanate" and "thiocyanate" refer to $[O=C=N]^-$ and $[S=C=N]^-$ anions respectively.

The process described hereinabove is preferably effected in the presence of a base, and more preferably, in the presence of an excess of a base, so as to prevent the formation of a corresponding salt. Any of the commonly used bases can be utilized, including, for example, carbonates, amines, and the like.

Alternatively, the process described hereinabove can further be effected by reacting the obtained product with an acid, so as to form the corresponding acid addition salt.

For further details regarding the reagents and conditions at which the process is preferably effected are delineated in the Examples section that follows.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

The compounds presented herein are all based on a heterocyclic core, derived from known PDE5 inhibitors and/or dopamine D4 agonists, which is linked to a second moiety, optionally via a bridging moiety. The second moiety is mostly a heteroalicyclic moiety, a heteroaryl moiety and/or an aryl moiety. As demonstrated hereinbelow (see, for example, Table 1), compounds having a variety of heterocyclic cores have been prepared and practiced. Based on their heterocyclic core, the compounds presented herein may be grouped into several families.

Family 1 comprises compounds having a quinazolin-4 (3H)-one or 1H-purin-6-one heterocyclic core moiety, being substituted or non-substituted, which is linked to a second moiety, preferably via position 2 of the quinazolinone or the purinone. Such compounds correspond to compounds having general Formula I above, in which A is C, B is N, D is $=C-NR_2-$, E is $C=O$, and T is CRa. For quinazolinones, Q is —CRd- and M is —CRb=CRc-; for purinones, Q is N and M is NRb (see, general Formula I).

Family 2 comprises compounds having a 4H-chromen-4-one, chroman-4-one, or 4H-benzo[e][1,3]oxazin-4-one heterocyclic core moiety, being substituted or non-substituted, which is linked to a second moiety, preferably via position 2 of the chromenone, chromanone or benzoxazinone. Such compounds correspond to compounds having general Formula I above, in which A is C, B is O, D is $-C=CR_2$, $-CR_1-CR_2R_3-$, or $-C=N-$, E is $C=O$, M is —CRb=CRc-, T is CRa, and Q is —CRd-.

Family 3 comprises compounds having a 4H-pyrido[1,2-a]pyrimidin-4-one heterocyclic core moiety, being substituted or non-substituted, which is linked to a second moiety, preferably via position 2 of the pyridopyrimidinone. Such compounds correspond to compounds having general Formula I above, in which A is N, B is N, D is $-C=CR_2-$, E is $C=O$, M is —CRb=CRc-, T is CRa, and Q is CRd.

Family 4 comprises compounds having a 2-benzyl-1H-benzo[d]imidazole heterocyclic core moiety, being substituted or non-substituted, which is linked to a second moiety via, preferably via position 2 of the benzoimidazole. Such compounds correspond to compounds having general Formula I above, in which A is C, B is N, D is $=C-$, E is $NR_4$, K is $-CH(C_6H_5)$ or a derivative thereof, M is —CRb=CRc-, T is CRa, and Q is —CRd-.

Family 5 comprises compounds having a quinoxalin-2 (1H)-one heterocyclic core moiety, being substituted or non-substituted, which is linked to a second moiety, preferably via position 3 of the quinoxalinone. Such compounds correspond to compounds having general Formula I above, in which A is C, B is N, D is $=C-$, E is $-C(=O)-NR_4-$, M is —CRb=CRc-, T is CRa, and Q is CRd.

Family 6 comprises compounds having a purine-2,6(3H, 7H)-dione heterocyclic core moiety, being substituted or non-substituted, which is linked to a second moiety, preferably via position 8 of the purinedione. Such compounds correspond to compounds having general Formula I above, in which A is C, B is N, D is $=C-$, E is $NR_4$, M is $-C(=O)-NRb-$, Q is $C=O$, and T is NRa.

Family 7 comprises compounds having a 9H-pyrido[3,4-b]indole (also known as β-carboline) heterocyclic core moiety, being substituted or non-substituted, which is linked to a second moiety, preferably via position 3 of the pyridoindole. Such compounds correspond to compounds having general Formula I above, in which A is C, B is $CR_{15}$, D is $=C-$, E is $-CR_4=N-$, M is NRb, T is CRa, Q is CRd, and Rd and Ra are linked such that together they form an optionally substituted benzene ring.

Family 8 comprises compounds having a quinolin-4-ol heterocyclic core moiety, being substituted or non-substituted, which is linked to a second moiety, preferably via position 3 of the quinolinol. Such compounds correspond to compounds having general Formula I above, in which A is C, B is $CR_{15}$, D is $=C-$, E is $-CR_4=N-$, M is CRb=CRc-, Q is CRd, T is CRa, and $R_{15}$ is hydroxy and related derivatives such as, for example, alkoxy, aryloxy, carboxy, sulfate and carbamate.

The chemical structures of exemplary compounds of Families 1-8, as well as other exemplary compounds according to the present embodiments, which have been successfully prepared, are presented in Table 1 below.

Materials and Experimental Methods

Materials and Instrumental Data:

All reagents were commercially available and were used without further purification, unless otherwise indicated. Dry THF and diethyl ether were obtained by distillation from benzophenonesodium under nitrogen immediately before use.

Column chromatography was carried out using silica gel 60 (230-400 mesh).

J. T. Baker flexible thin layer chromatography sheets (silica gel IB2-F) were used to monitor reactions.

$^1$H-NMR spectra were recorded using a 300 MHz Bruker ARX-300NMR spectrometer. Chemical shifts are reported in δ values ppm relative to an internal reference (0.03%, v/v) of tetramethylsilane (TMS) in $CDCl_3$, unless otherwise indicated.

Activity Assays:

Binding to Dopamine Receptors:

Compounds were assayed for competitive binding to $D_2$ $_{SHORT}$ and $D_{4.4}$ type dopamine receptors. Both receptor types are expressed as human recombinant proteins in CHO cells, as described, for example, in Jarvis et al. (1973); Van Tol et al. (1991) and Van Tol et al. (1992).

Determination of binding to D2 short receptor was performed using [$^3$H]-spiperone, a D2 receptor ligand (Gundlach et al., 1984), as a radioligand (20-60 Ci/mmol, 0.2 nM) in the presence of various concentrations of the tested compound. Reactions were carried out in 50 mM TRIS-HCl (pH 7.4) containing 120 mM NaCl, 5 mM KCl, 5 mM $MgCl_2$ and 1 mM EDTA, for 60 minutes at 25° C. The reaction was terminated by rapid vacuum filtration onto glass fiber filters. Radioactivity trapped onto the filters was determined (counted) and compared to control values in order to accurately evaluate any interaction of the test compound(s) with the cloned dopamine D2 short binding site.

Determination of binding to D4.4 receptor was performed using [$^3$H]-YM-09151-2 (70-87 Ci/mmol, 0.3 nM), as a radioligand, in with the presence of various concentrations of the tested compound. Reactions were carried out in 50 mM TRIS-HCl (pH 7.4) containing 5 mM $MgCl_2$, 5 mM EDTA, 5 mM KCl and 1.5 mM $CaCl_2$, for 60 minutes at 22° C. The reaction was terminated by rapid vacuum filtration onto glass fiber filters. Radioactivity trapped onto the filters was determined (counted) and compared to control values in order to accurately evaluate any interaction of the tested compound(s) with the cloned dopamine D4.4 binding site.

D4/D2 binding ratios were determined based on the ratio of the concentration of each tested compound required to inhibit 50% of the radioligand binding for each receptor.

GTPgammaS Cellular Assay:

Human recombinant dopamine $D_{4.4}$ receptors expressed in CHO-K1 cells were used. The tested compound was pre-incubated with 0.1 mg/ml membranes and 10 μM GDP for 20 minutes at 25° C. in modified HEPES buffer (pH 7.4). SPA beads were then added and the mixture was maintained for additional 60 minutes at 30° C. The reaction was initiated by the addition of 0.3 nM [$^{35}$S]GTPγS, and the obtained reaction mixture were incubated for 30 minutes. Test compound-induced increase of [$^{35}$S]GTPγS binding by 50 percent or more (≧50%) relative to the 1 μM dopamine response indicated dopamine $D_{4.4}$ agonist activity. Test compound-induced inhibition of 1 μM dopamine-induced increase of [$^{35}$S]GTPγS binding response by 50 percent or more (≧50%) indicated receptor antagonist activity. Compounds were tested at concentrations of 5, 1, 0.1, 0.01 μM.

Phosphodiesterase Type 5 (PDE5) Inhibition:

Phosphodiesterase type 5 (PDE5) catalyzes the conversion of cAMP or cGMP to their respective monophosphate forms. PDE5 has a high $K_m$ for cAMP and a low $K_m$ for cGMP, is insensitive to $Ca^{2+}$/calmodulin or cGMP regulation, and is relatively sensitive to inhibitors such as dipyridamol and zaprinast.

PDE5 partially purified from human platelets was used. The tested compound (at a concentration of 0.1, 1, 20 or 50 μM) and/or vehicle was incubated with 3.5 μg enzyme and 1 μM cGMP containing 0.01 μM [$^3$H]cGMP in Tris buffer pH 7.5 for 20 minutes at 30° C. Since enzyme activity may change from lot to lot, the concentration used was adjusted if required.

The reaction was terminated by boiling the reaction mixture for 2 minutes. The obtained GMP was then converted to guanosine by addition of 10 mg/ml snake venom nucleotidase and further incubation at 30° C. for 10 minutes. Unhydrolyzed cGMP was bound to AG1-X2 resin, and remaining [$^3$H]Guanosine in the aqueous phase was quantitated by scintillation counting.

Example 1

Preparation of Family 1 Compounds

General Procedure

The general synthetic pathway for preparing Family 1 compounds is depicted in Scheme I below:

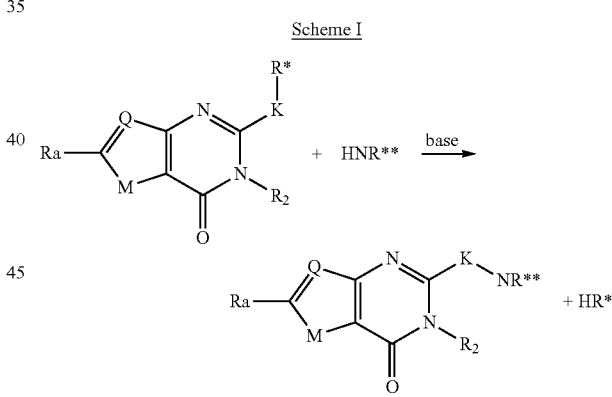

wherein:

R* is a suitable leaving group such as, for example, halide, mesylate and triflate, and is preferably halide (e.g., chloride).

HNR** is a cyclic (alicyclic or aromatic) nucleophile, containing a nucleophilic nitrogen atom, preferably selected from the following groups of compounds:

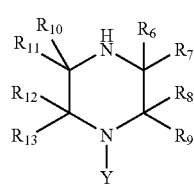

-continued

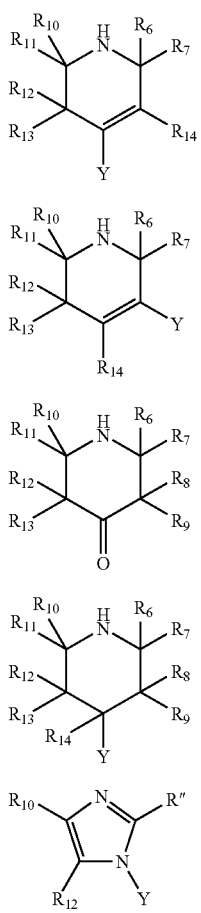

and

K, Q, M, Y, Ra, R", $R_2$, $R_6$-$R_{14}$ are as defined hereinabove for general Formula I.

Approximately equimolar amounts of 2-(chloromethyl)quinazolin-4(3H)-one (or a derivative thereof in which the quinazolinone is substituted) and a cyclic nucleophile (HNR** in Scheme I above) are dissolved in a polar solvent such as DMF. After a few seconds, an excess of a base (e.g., triethylamine) is added, and the reaction is stirred until no traces of reactant materials are observed by TLC. A further excess of the base is then added along with an excess of water. The solid precipitate is then collected by vacuum filtration, washed with cold water and dried for several hours to give the product.

Similarly, 2-(chloromethyl)-1H-purin-6(7H)-one (or a derivative thereof) is used as a starting material instead of 2-(chloromethyl)quinazolin-4(3H)-one.

Since excess of base is used, the salt HR* (e.g., a hydrochloride salt, a methanesulfonate salt, a trifluromethanesulfonate salt, see, Scheme I) is obtained as a by-product, whereby the product itself is obtained in a free base form.

However, when (f) is used a cyclic amine, a salt of a positively charged compound is obtained due to the formation of a quaternary ammonium and an anion, is formed.

For other compounds in this family, formed upon reacting a quinazolinone with other cyclic amines, optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds 101-130, 405, 408, 409, B-4, B-8, B-9, B-10, B-11, B-14, B-33, B-43, B-72, B-75, and B-82 (see, Table 1) have been prepared.

In a typical example, 2-((4-(pyrimidin-2-yl)piperazin-1-yl)methyl)quinazolin-4-one (Compound 123, see, Table 1) was prepared as follows:

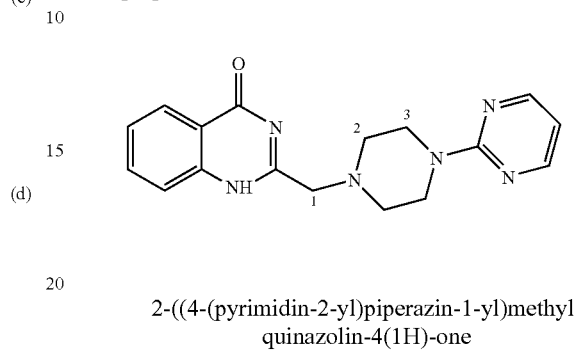

2-((4-(pyrimidin-2-yl)piperazin-1-yl)methyl)quinazolin-4(1H)-one 300 mg of 2-(chloromethyl)quinazolin-4(3H)-one and 300 mg 2-(piperazin-1-yl)pyrimidine were dissolved in 5 ml of DMF at room temperature. After a few seconds, 0.5 ml of triethylamine was added, and the reaction mixture was stirred at ambient temperature, while being monitored by TLC. Once the reaction was completed (overnight), additional 0.2 ml of triethylamine was added, followed by 3 ml of water, and the mixture was cooled to 0° C. The solid precipitate was thereafter collected by vacuum filtration, washed with cold water and dried for 2 hours at 50° C., to give 370 mg (75% yield) of the product.

$^1$H-NMR (CDCl$_3$): δ=10.05 (bs, 1H, NH), 8.32-6.48 (m, 7H, H$_{ar}$), 3.93-3.88 (t, 4H), 3.62 (s, 2H), 2.68-2.63 (t, 4H) ppm.

Example 2

Preparation of Family 2 Compounds

General Procedure

The general synthetic pathway for preparing Family 2 compounds is depicted in Scheme II below:

Scheme II

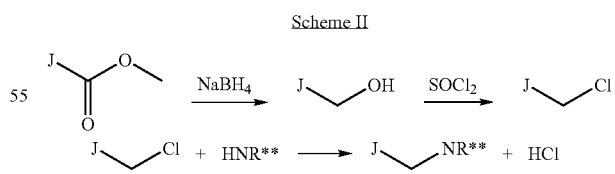

wherein:

J is the substituted or non-substituted 4H-chromen-4-one, chroman-4-one, or 4H-benzo[e][1,3]oxazin-4-one heterocyclic core moiety for family 2 compounds, as defined hereinabove;

HNR** is a cyclic nitrogen-containing nucleophile such as:

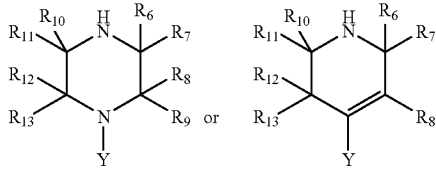

and

Y and $R_6$-$R_{13}$ are as defined hereinabove for general Formula I.

Methyl 4-oxo-4H-chromene-2-carboxylate (or a derivative thereof in which the oxochromene is substituted, J in Scheme II above) is dissolved in an alcoholic solvent (e.g., methanol) at room temperature, and a reducing agent (e.g., $NaBH_4$) is slowly added to the solution until the starting material is no longer detected by TLC. The solvent is then evaporated and the resulting residue is mixed with water. The pH of the resulting mixture is adjusted to between 5 and 9, to prevent decomposition of the chromone. The water is then washed several times with a non-polar solvent such as chloroform. The combined organic extracts are dried over $Na_2SO_4$, and the solvent is evaporated.

The obtained residue is dissolved in an anhydrous non-polar solvent such as chloroform at room temperature, and an excess of thionyl chloride is added. The reaction mixture is stirred for approximately 24 hours at room temperature. The solvent is thereafter evaporated, and the resulting liquid is dissolved in anhydrous hexane, which is thereafter evaporated.

Alternatively, the hydroxymethyl oxochromene can be reacted with other reagents, such as triflic anhydride or mesyl chloride, so as to produce an oxochromene substituted by a moiety that contains a leaving group other than chloride.

The obtained residue is then reacted with a cyclic amine (HNR** in Scheme II above), at a ratio of e.g., 5:3, in the presence of an excess of a base such as $K_2CO_3$ or $Na_2CO_3$ in an as alcoholic solvent (e.g., ethanol), while refluxing the reaction mixture for a few hours. The solvent is thereafter evaporated and the crude product is optionally purified by column chromatography to yield the final product.

Similarly, methyl 4-oxochroman-2-carboxylate, or methyl 4-oxo-4H-benzo[e][1,3]oxazine-2-carboxylate (substituted or non-substituted) may be used as starting materials instead of methyl 4-oxo-4H-chromene-2-carboxylate (J in Scheme II above).

Since excess of base is used, the salt HCl (or any other salt, depending on the reactive oxochromene derivative used), is obtained as a by-product, whereby the product itself is obtained in a free base form.

Using this general procedure, Compounds 201-207 and 401-404 (see, Table 1) have been prepared.

In a typical example, 2-((4-(pyridin-2-yl)piperazin-1-yl)methyl)-4H-chromen-4-one (Compound 204, see, Table 1) was prepared as follows:

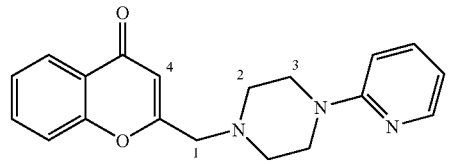 [SMILES: O=c1cc(CN2CCN(c3ccccn3)CC2)oc2ccccc12]

2-((4-(pyridin-2-yl)piperazin-1-yl)methyl)-4H-chromen-4-one 500 mg of methyl 4-oxo-4H-chromene-2-carboxylate were dissolved in 25 ml of anhydrous methanol at room temperature, and $NaBH_4$ was thereafter added to the solution slowly, until the starting material was no longer detected by TLC (about 300 mg). The solvent was then evaporated and a mixture of 1.1 gram of $NaH_2PO_4.2H_2O$ in 30 ml of water was added to the resulting residue. The pH of the mixture was maintained between 5 and 9, so as to prevent decomposition of chromone. The aqueous solution was washed with chloroform (3×50 ml) and the combined organic extracts were dried over $Na_2SO_4$. The solvent was evaporated to give 2-(hydroxymethyl)-4H-chromen-4-one which was used without future purification.

The 2-(hydroxymethyl)-4H-chromen-4-one was dissolved in 30 ml of anhydrous chloroform at room temperature, 1 ml of thionyl chloride was added to the solution, and reaction mixture was stirred at room temperature for 24 hours. The solvent was thereafter evaporated, and the obtained liquid was dissolved in anhydrous hexane, which was also evaporated again to give 2-(chloromethyl)-4H-chromen-4-one which was further reacted without purification.

The 2-(chloromethyl)-4H-chromen-4-one, excess of $Na_2CO_3$ and 250 mg of 1-(pyridin-2-yl)piperazine were mixed in 20 ml of anhydrous ethanol. The mixture was refluxed for 6 hours, and the solvent was thereafter evaporated. The obtained gel was purified by column chromatography, using a gradient mixture of 10-30% ethyl acetate in hexanes as eluent, to give 176-250 mg (21-30% total yield) of Compound 204 as yellowish crystals.

$^1$H-NMR ($CDCl_3$): δ=8.22-6.60 (m, 8H, $H_{ar}$), 6.49 (s, 1H), 3.66-3.58 (t, 4H), 3.55 (s, 2H), 2.74-2.70 (t, 4H) ppm.

Example 3

Preparation of Family 3 Compounds

General Procedure

The general synthetic pathway for preparing Family 3 compounds is depicted in Scheme III below:

Scheme III

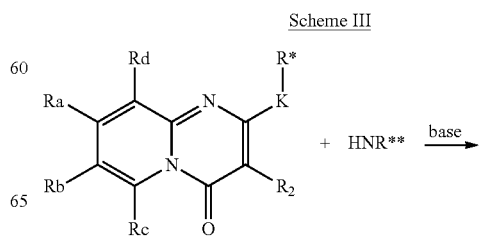

-continued

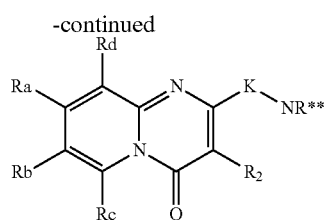

wherein:
R* is a suitable leaving group as described herein;
HNR** is a nitrogen-containing cyclic nucleophile such as, for example:

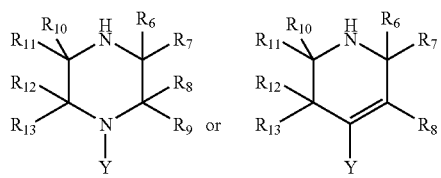

and
Y, K, $R_2$, $R_6$-$R_{13}$, and Ra-Rd are as defined hereinabove for Formula I.

Approximately equimolar amounts of 2-(chloromethyl)-4H-pyrido[1,2-a]pyrimidin-4-one (or a derivative thereof in which the pyridopyrimidine is substituted and/or in which the chloro is replaced by another leaving group) and a cyclic amine (HNR** in Scheme III above) are dissolved in a polar solvent (e.g., DMF). After a few seconds, an excess of a base (e.g., triethylamine) is added, and the reaction mixture is stirred at room temperature overnight. A further excess of the base is then added along with an excess of water and the reaction mixture is cooled. The precipitated solid is collected by vacuum filtration and dried to give the final product.

Since excess of base is used, the salt HR* (e.g., a hydrochloride salt, a methanesulfonate salt, a trifluromethane-sulfonate salt, see, Scheme III) is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds 301-307 (see, Table 1) have been prepared.

In a typical example, 2-((4-(2-fluorophenyl)piperazin-1-yl)methyl)-4H-pyrido[1,2-a]pyrimidin-4-one (Compound 303, see, Table 1) was prepared as follows:

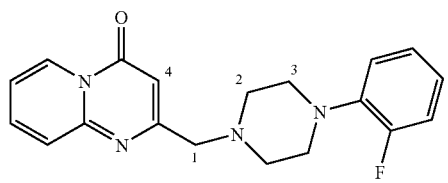 [SMILES: O=c1cc(CN2CCN(c3ccccc3F)CC2)nc2ccccn12]

2-((4-(2-fluorophenyl)piperazin-1-yl)methyl)-4H-pyrido[1,2-a]pyrimidin-4-one 300 mg of 2-(chloromethyl)-4H-pyrido[1,2-a]pyrimidin-4-one and 300 mg of 1-(2-fluorophenyl)piperazine were dissolved in 10 ml of DMF at room temperature. After a few seconds, 0.8 ml of triethylamine was added and the reaction mixture was stirred at ambient temperature overnight. Thereafter, another 0.2 ml of triethylamine was added, followed by 3 ml of water, and the reaction mixture was cooled to 0° C. The precipitated solid was collected by vacuum filtration, washed with cold water and dried at 50° C., to give 358 mg (62% yield) of the Compound 303.

$^1$H-NMR (CDCl$_3$): δ=9.07-6.92 (m, 8H, H$_{ar}$), 6.72 (s, 1H), 3.64 (s, 2H), 3.20-3.15 (t, 4H) 2.80-2.75 (t, 4H) ppm.

Example 4

Preparation of Family 4 Compounds

General Procedure

The general synthetic pathway for preparing Family 4 compounds is depicted in Scheme IV below:

Scheme IV

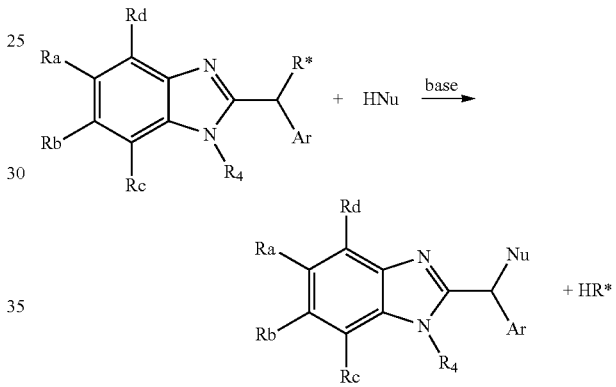

wherein:
R* is a suitable leaving group as described herein;
Ar is aryl;
Nu is a nucleophile such as, for example:

(a)
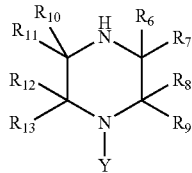

(b)
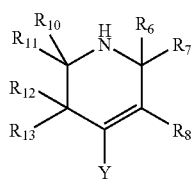

(c) an alcohol (e.g. ethanol);
and
Y, $R_4$, $R_6$-$R_{13}$, and Ra-Rd are as defined hereinabove for general Formula I.

2-(chloro(phenyl)methyl)-1H-benzo[d]imidazole (substituted or non-substituted), or a derivative is which the chloro is replaced by another leaving group, and a nucleophile such as a cyclic amine (e.g., a piperazine, Nu in Scheme IV above) are dissolved in a polar solvent (e.g., DMF). After a few seconds, an excess of a base (e.g., triethylamine) is added, and the reaction mixture is stirred until the starting material is no longer detected by TLC. A further excess of the base is then added along with an excess of water and the reaction mixture is cooled. The precipitated solid is collected by vacuum filtration and dried for several hours to give the final product.

Since excess of base is used, the salt HR* (e.g., a hydrochloride salt, a methanesulfonate salt, a trifluromethanesulfonate salt, see, Scheme IV) is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds 501-511 (see, Table 1) have been prepared.

In a typical example, 5-benzyl-2-(phenyl(4-(pyrimidin-2-yl)piperazin-1-yl)methyl)-1H-benzo[d]imidazole was prepared as follows:

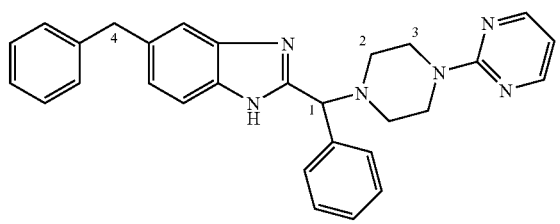 [SMILES: c1ccc(Cc2ccc3[nH]c(C(c4ccccc4)N4CCN(c5ncccn5)CC4)nc3c2)cc1]

5-benzyl-2-(phenyl(4-(pyrimidin-2-yl)piperazin-1-yl)methyl)-1H-benzo[d]imidazole 300 mg of 5-benzyl-2-(chloro(phenyl)methyl)-1H-benzo[d]imidazole and 300 mg 2-(piperazin-1-yl)pyrimidine were dissolved in 5 ml of DMF at room temperature. After a few seconds, 0.5 ml of triethylamine was added, and the reaction mixture was stirred at room temperature, while being monitored by TLC. Once the starting material was no longer detected (overnight), additional 0.2 ml of triethylamine was added, followed by 3 ml of water, and the reaction mixture was cooled to 0° C. The precipitated solid was collected by vacuum filtration, washed with cold water and dried for 2 hours at 50° C., to give 360 mg (80% yield) of the product (BPRM-VR-2'b).

$^1$H-NMR (CDCl$_3$): δ=12.34 (bs, 1H, NH) 8.22-6.38 (m, 16H, H$_{ar}$), 4.72 (s, 1H), 4.07 (s, 2H), 3.81-3.76 (t, 4H), 2.56-2.40 (t, 4H) ppm.

Example 5

Preparation of Family 5 Compounds

General Procedure

The general synthetic pathway for preparing Family 5 compounds is depicted in Scheme V below:

Scheme V

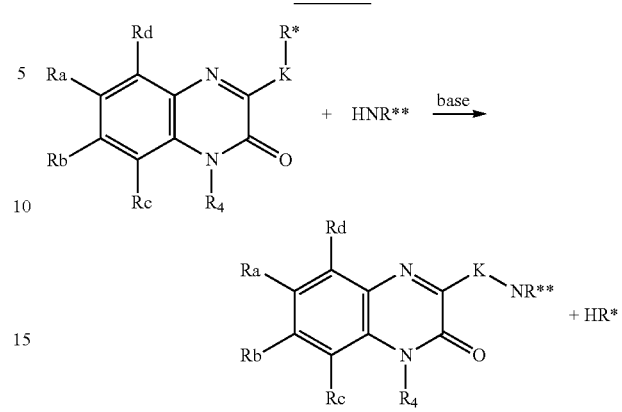

wherein:
R* is a suitable leaving group as described herein;
HNR** is a nitrogen-containing cyclic nucleophile such as, for example:

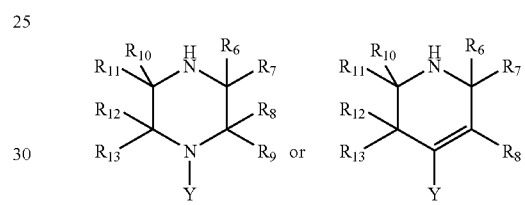

and

Y, K, R$_1$, R$_4$, R$_6$-R$_{13}$, R$_{15}$ and Ra-Rd are as defined hereinabove for Formula I.

Approximately equimolar amounts of 3-(bromomethyl)quinoxalin-2(1H)-one (or a derivative thereof in which the quinoxalinone is substituted, or in which the bromo is replaced by another leaving group) and a cyclic amine (HNR** in Scheme V above) are dissolved in a polar solvent (e.g., ethanol). After a few seconds, an excess of a base (e.g., sodium carbonate) is added, and the reaction mixture is refluxed for a few hours. The solvent is then distilled under reduced pressure, and the remaining residue is collected in a mixture of dichloromethane and water (e.g. at a 2:1 ratio of dichloromethane to water). After separating the organic phase, the solvent is evaporated and the product is purified by column chromatography (e.g. by using a 9:1 mixture of ethyl acetate and methanol as the eluent).

Since excess of base is used, the salt HR* (e.g., a hydrochloride salt, a methanesulfonate salt, a trifluromethanesulfonate salt, see, Scheme V) is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds B-34, B-37, B-42 and B-44 (see, Table) are obtained.

In a typical example, 3-((4-(2-methoxyphenyl)piperazin-1-yl)methyl)-3,4-dihydroquinoxalin-2(1H)-one was prepared as follows:

239 mg (1 mmol) of 3-(bromomethyl)quinoxalin-2(1H)-one was mixed with 195 mg (1 mmol) of 1-(2-methoxyphenyl)piperazine hydrochloride in ethanol in presence of 318 mg (3 mmol) sodium carbonate. The mixture was refluxed for 5 hours. Thereafter, the ethanol was evaporated under reduced pressure, and the remaining residue was dissolved in a 2:1 mixture of dichloromethane and water. The organic phase was separated, the solvent was then evaporated and the product was purified by column chromatography using a 9:1 mixture of ethyl acetate and methanol as the eluent. The product was obtained in 57% yield.

$^1$H-NMR (CDCl$_3$): δ=9.1 (bs, 1H, NH), 8.21-6.22 (m, 8H, H$_{ar}$), 3.90-3.85 (t, 4H), 3.65 (s, 2H), 3.45 (s, 2H), 2.70-2.67 (t, 4H) ppm.

Example 6

Preparation of Family 6 Compounds

General Procedure

The general synthetic pathway for preparing Family 6 compounds is depicted in Scheme VIa below:

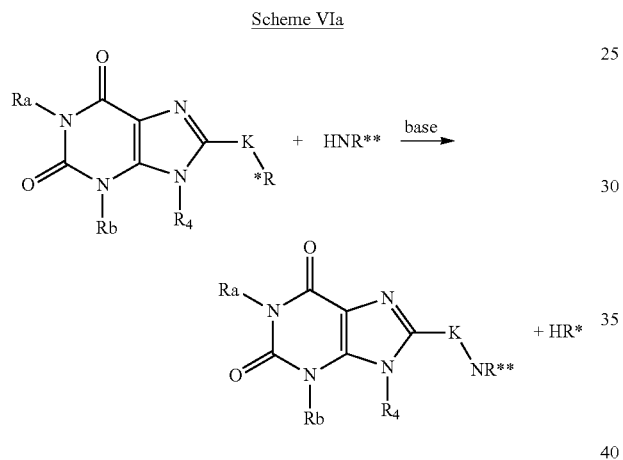

wherein:

R* is a leaving group, as described herein;

HNR** is a nitrogen-containing cyclic nucleophile such as, for example:

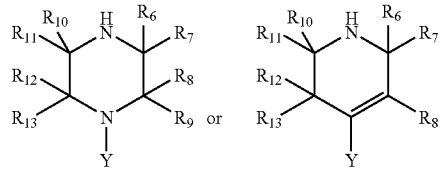

and

Y, K, R$_4$, R$_6$-R$_{13}$, and Ra-Rb are as defined hereinabove for Formula I.

Approximately equimolar amounts of 8-(chloromethyl)-1H-purine-2,6(3H,7H)-dione or a derivative thereof (in which the purinedione is substituted and/or in which chloro is replaced by another leaving group), and a cyclic amine (HNR** in Scheme VIa above) are dissolved in a polar solvent (e.g., ethanol). After a few seconds, an excess of a base (e.g., sodium carbonate) is added, and the reaction mixture is refluxed for a few hours. The solvent is then distilled under reduced pressure, and the remaining residue is collected in a mixture of dichloromethane and water (e.g. at a 2:1 ratio of dichloromethane to water). After separating the organic phase, the solvent is evaporated and the product is purified by column chromatography (e.g. by using a 9:1 mixture of ethyl acetate and methanol as the eluent).

Since excess of base is used, the salt HR* (e.g., a hydrochloride salt, a methanesulfonate salt, a trifluromethanesulfonate salt, see, Scheme VI) is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds Xan-1 and Xan-2 (see, Table 1) are obtained.

In a typical example, 1,3-diethyl-8-((4-(2-fluorophenyl)piperazin-1-yl)-1H-purine-2,6(3H,7H)-dione was prepared as depicted in Scheme VIb below:

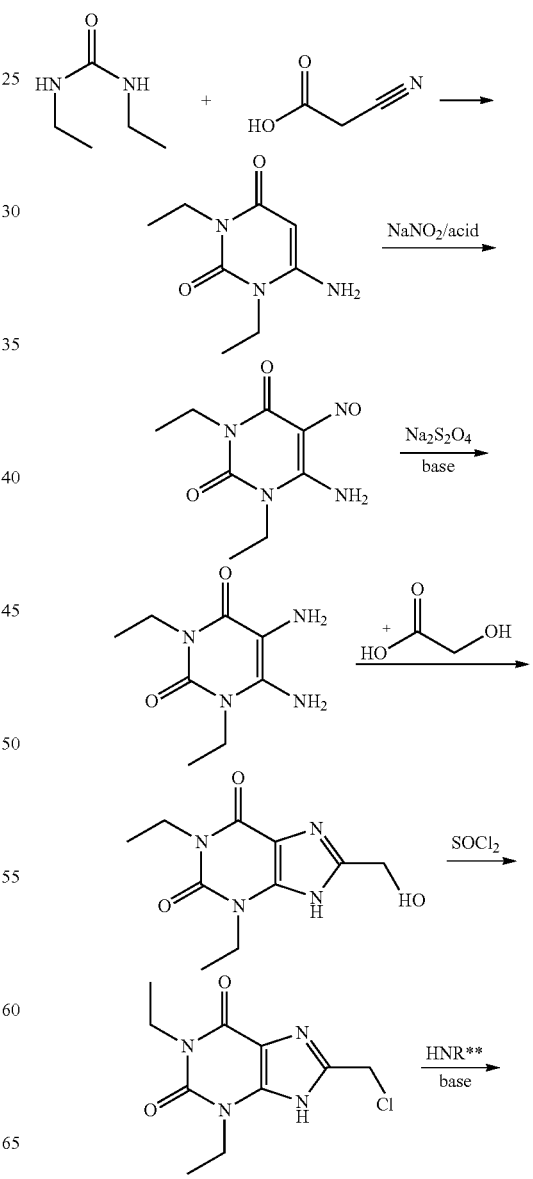

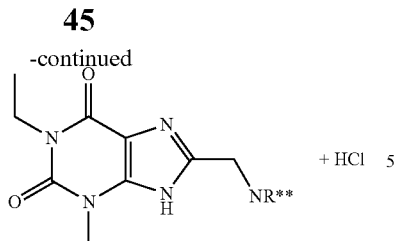

wherein NR** is 1-(2-fluorophenyl)piperazine.

12.69 grams (0.14 mol) of diethylurea and 11.90 grams (0.14 mol) of cyanoacetic acid were heated in acetic anhydride at 60° C. for 3 hours, under dry atmosphere. Thereafter, the acetic anhydride and remaining cyanoacetic acid were evaporated, 5% sodium hydroxide was added and the mixture was stirred and cooled. 20 grams of 6-amino-1,3-diethyluracil were obtained as a precipitate. 11.8 grams of sodium nitrite in 70 ml water were then added while cooling and stirring and the solution was then acidified by adding 70 ml acetic acid. The mixture was stirred at room temperature for additional 2.5 hours. The resulting precipitate was filtered, washed with water, ethanol and finally ether so afford 10.1 grams of 6-amino-1,3-diethyl-5-nitrosouracil, as a violet product.

10 grams of this product were heated in 64 ml ammonium hydroxide at 60° C. while stirring vigorously. 28 grams of sodium hydrosulfite in 150 ml water were thereafter during 20 minutes resulting in a color change of the solution to yellowish, and heating was then continued for additional 15 minutes. The mixture was cooled to room temperature and then cooled at 4° C. overnight to afford 5,6-diamino-1,3-diethyluracil (6.1 grams) as a precipitate.

2.1 grams of 5,6-diamino-1,3-diethyluracil were stirred in 3.4 grams glycolic acid for 1 hour at 100° C. A 1:1 solution of ethanol and water (20 ml) was thereafter added to the cooled and stirred mixture, followed by the addition of 8 grams of sodium hydroxide in 30 ml water, which raised the pH to above 12. The solution was then refluxed for 2.5 hours, cooled, 30 ml acetic acid were added, and the mixture was then cooled overnight at 4° C. The resulting precipitate was collected and dried, to give 1,3-diethyl-8-hydroxymethylxanthine (1.5 gram).

1 gram of 1,3-diethyl-8-hydroxymethylxanthine was added to an excess (3 grams) of thionyl chloride and the mixture was refluxed for 1 hour. The excess thionyl chloride was evaporated and the resulting residue was crystallized from hexane, to yield 1,3-diethyl-8-chloromethylxanthine (0.8 gram).

256 mg (1 mmol) of 1,3-diethyl-8-chloromethylxanthine and 180 mg (1 mmol) of 1-(2-fluorophenyl)piperazine were mixed in ethanol with 318 mg of sodium carbonate. The mixture was then refluxed for 7 hours. The ethanol was then evaporated and the resulting residue was collected in a 2:1 mixture of dichloromethane and water. The organic phase was then separated, the solvent was evaporated and the product was purified by column chromatography using a 9:1 mixture of ethylacetate and methanol as eluent, to yield 200 mg (50% yield) of the final product.

$^1$H-NMR (CDCl$_3$): δ=11.52 (bs, 1H, NH), 7.19-6.83 (m, 4H, H$_{ar}$), 4.16-4.01 (m, 4H), 3.74 (s, 2H), 3.14-3.05 (t, 2H), 2.72-2.69 (t, 4H), 1.33-0.096 (m, 6H) ppm.

Using the above procedure, with different starting materials, yields other compound of Family 6.

Example 7

Preparation of Family 7 Compounds

General Procedure

The general synthetic pathway for preparing Family 7 compounds is depicted in Scheme VII below:

Scheme VII

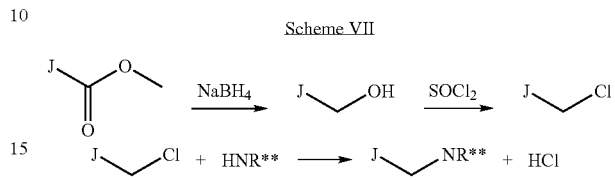

wherein:

J is the substituted or non-substituted 9H-pyrido[3,4-b]indole (β-carboline) heterocyclic core moiety for family 7 compounds, as defined hereinabove;

HNR** is a cyclic nitrogen-containing nucleophile such as:

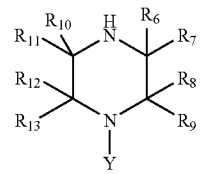

and Y and R$_6$-R$_{13}$ are as defined hereinabove for general Formula I.

3-carbomethoxy-β-carboline or a derivative thereof (J in Scheme VII above) is dissolved in a polar solvent (e.g., THF), and a reducing agent (e.g., NaBH$_4$) is added to the solution. The mixture is stirred for a few hours and cooled. An excess of water is then added, and the mixture is stirred for another few hours. The solvent is thereafter evaporated and the resulting residue is dissolved in water, washed several times with one or more non-polar solvents such as dichloromethane and ethyl acetate, and the combined organic extracts are then evaporated. The remaining residue is purified by column chromatography (e.g., on a silica gel with elution by a 9:1 mixture of ethylacetate and methanol), to give a 3-hydroxymethyl-β-carboline intermediate.

The intermediate is added to an excess of thionyl chloride, and the mixture is refluxed for approximately 1 hour. The excess thionyl chloride is then evaporated and a residue of a 3-(chloromethyl)-β-carboline intermediate is crystallized from hexane.

Alternatively, the hydroxymethyl carboline can be reacted with other reagents, such as triflic anhydride or mesyl chloride, so as to produce a carboline substituted by a moiety that contains a leaving group other than chloride.

The obtained residue is then reacted with an approximately equimolar amount of cyclic amine (HNR** in Scheme II above), in the presence of an excess of a base such as K$_2$CO$_3$ in an alcoholic solvent (e.g., ethanol), while refluxing the reaction mixture for a few hours. The solvent is thereafter evaporated and the crude product is optionally purified by column chromatography to yield the final product.

Since excess of base is used, the salt HCl (or any other salt, depending on the leaving group), is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

In a typical example, 3-(4-((9H-pyrido[3,4-b]indol-3-yl)methyl)piperazin-1-yl)phenol was prepared as follows:

3.5 grams (15 mmol) of 3-carbomethoxy-β-carboline were suspended in 300 ml THF, 2.7 grams (75 mmol) sodium borohydride were added and the mixture was stirred at room temperature for 12 hours. The mixture was then cooled, 50 ml water were added and the resulting mixture was stirred overnight. The solvent was evaporated under reduced pressure and water (300 ml) was again added. The aqueous suspension was extracted with dichloromethane, followed by ethylacetate, the organic extracts were combined, and the solvent was evaporated under reduced pressure. The remaining residue was purified by column chromatography on silica gel, using and a 9:1 mixture of ethylacetate and methanol as eluent, to give 3-(hydroxymethyl)-β-carboline (2.5 grams, 81% yield).

The 3-(hydroxymethyl)-β-carboline was added to an excess (3 grams) of thionyl chloride and the mixture was refluxed for 1 hour. The excess thionyl chloride was then evaporated and the obtained residue was crystallized from hexane. 2.5 grams of 3-(chloromethyl)-β-carboline was obtained.

216 mg (1 mmol) of 3-(chloromethyl)-β-carboline and 178 mg (1 mmol) of 1-(3-hydroxyphenyl)piperazine were mixed in ethanol, 318 mg of sodium carbonate were added and the mixture was refluxed for 7 hours. Thereafter, the ethanol was distilled under reduced pressure, and the remaining residue was collected in a 2:1 mixture of dichloromethane and water. The organic phase was separated, the solvent was evaporated and the product was then purified by column chromatography using a 9:1 mixture of ethyl acetate and methanol as eluent, to give 214 mg (60% yield) of the final product.

$^1$H-NMR (CDCl$_3$): δ=11.70 (bs, 1H, NH), 8.61-6.11 (m, 10H, H$_{ar}$), 3.70 (s, 2H), 3.34-3.23 (t, 2H), 2.83-2.52 (t, 4H) ppm.

Example 8

Preparation of Family 8 Compounds

General Procedure

The general synthetic pathway for preparing Family 8 compounds is depicted in Scheme VIII below:

Scheme VIII

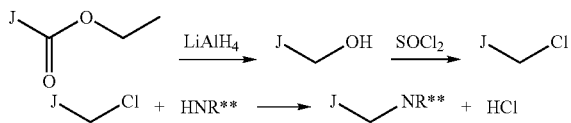

wherein:

J is the substituted or non-substituted quinolin-4-ol heterocyclic core moiety for family 8 compounds, as defined hereinabove;

HNR** is a cyclic nitrogen-containing nucleophile such as:

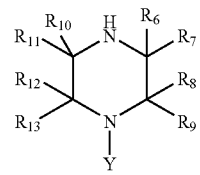

wherein Y and R$_6$-R$_{13}$ are as defined hereinabove for general Formula I.

Ethyl 4-hydroxy-3-quinolinecarboxylate or a derivative thereof (J in Scheme VII above) is dissolved in a polar solvent (e.g., THF), and a reducing agent (e.g., LiAlH$_4$) is added to the solution. The mixture is then stirred for a few hours, cooled, an excess of water is added, and the mixture is stirred for another few hours. The solvent is then evaporated and the resulting residue is dissolved in water. The water is then washed several times with a non-polar solvent such as dichloromethane. The solvent of the organic extract is n evaporated, and the remaining residue is purified by column chromatography (e.g., on a silica gel with elution by a 9:1 mixture of ethylacetate and methanol), and a 3-(hydroxymethyl)quinolin-4-ol intermediate is obtained.

The intermediate is added to an excess of thionyl chloride, and the mixture is refluxed for approximately 1 hour. The excess thionyl chloride is then evaporated and a residue of a 3-(chloromethyl)quinolin-4-ol intermediate is crystallized from hexane.

Alternatively, the intermediate can be reacted with other reagents, such as triflic anhydride or mesyl chloride, so as to produce a quinoline substituted by a moiety that contains a leaving group other than chloride.

The obtained residue is then reacted with an approximately equimolar amount of a cyclic amine (HNR** in Scheme II above), in the presence of an excess of a base (e.g., K$_2$CO$_3$) in an alcoholic solvent (e.g., ethanol), while refluxing the reaction mixture for a few hours. The solvent is thereafter evaporated and the remaining residue is dissolved in a mixture of water with a non-polar solvent such as dichloromethane. The non-polar extract is then separated, and the solvent removed by evaporation. The crude product is optionally purified by column chromatography to yield the final product.

Since excess of base is used, the salt HCl (or any other salt, depending on the leaving group), is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

In a typical example, 3-((4-(3-hydroxyphenyl)piperazin-1-yl)methyl)-7-(trifluoromethyl)quinolin-4-ol was prepared as follows:

14 grams (50 mmol) of ethyl 4-hydroxy-7-trifluoromethyl-3-quinolinecarboxylate was suspended in 400 ml THF, and 9.5 grams (250 mmol) lithium aluminum hydride were added slowly. The mixture was stirred at room temperature for 12 hours, cooled, 250 ml water were added and the resulting mixture was stirred overnight. The solvent was thereafter evaporated, and water (300 ml) was again added. The aqueous suspension was extracted with dichloromethane. The organic extract was evaporated, and the remaining residue was purified by column chromatography on silica gel, using a 9:1 mixture of ethylacetate and methanol as eluent, to yield 4-hydroxy-7-trifluoromethyl-3-(hydroxymethyl)-quinoline (12 grams, 82% yield).

4-Hydroxy-7-trifluoromethyl-3-(hydroxymethyl)-quinoline (3.6 grams) was added to an excess (5.9 grams) of thionyl chloride and the mixture was refluxed for 1 hour. Excess thionyl chloride was then evaporated and the remaining residue was crystallized from hexane to give 4-hydroxy-7-trifluoromethyl-3-(chloromethyl)-quinoline (3.2 grams).

250 mg (1 mmol) of 4-hydroxy-7-trifluoromethyl-3-(chloromethyl)-quinoline and 178 mg (1 mmol) of 1-(3-hydroxyphenyl)piperazine were mixed in ethanol, 318 mg of sodium carbonate were added, and the mixture was refluxed for 8 hours. Thereafter, the ethanol was evaporated, and the remaining residue was collected in a 2:1 mixture of dichloromethane and water. The organic phase was separated, the solvent was evaporated and the residue was purified by column chromatography using a 9:1 mixture of ethylacetate and methanol as eluent to give 312 mg (78% yield) of the final product.

$^1$H-NMR (CDCl$_3$): δ=8.77-6.22 (m, 8H, H$_{ar}$), 3.82 (s, 2H), 3.37-3.21 (t, 2H), 2.66-2.55 (t, 4H), ppm.

Example 9

Activity Assays

The results obtained in the assays for D4 binding and PDE5 inhibition described hereinabove, for some of the exemplary compounds described herein, are presented in Table 2 below. The data displayed in Table represents the results obtained in current studies, whereby in some experiments, the observed activity was not quantitated and hence is designated as "active"; na denotes no activity; and ND denotes not determined (not tested yet).

As can be seen in Table 2, substantial inhibition of PDE5 was observed with many compounds at micromolar concentrations.

Additionally, a selective binding to D4 and agonistic activity with respect to this receptor were also observed in many compounds at micromolar concentrations, and with a desirable D4/D2 selectivity of from about 50:1 to over 500:1.

Importantly, as can further be seen in Table 2, several compounds were found to exhibit both PDE5 inhibition and D4 agonist activity (see, for example, Compounds 113, B-14 and B-72, indicating the potent activity of the designed compounds in treating various sexual disorders.

Further analysis of the obtained data may provide some insights on the structure activity relationship (SAR) of the tested compounds.

First, it is shown that, as envisioned herein, Family 1 compounds, having a heterocyclic core (a bicyclic moiety) that resembles that of known PDE-5 inhibitors (e.g., Sildenafil), exhibit a PDE-5 inhibition, presumably via hydrogen bonding to GLN817 and stacking interaction with PHR820 amino acid residues of the PDE5 enzyme [see, for example, Sung et al. *Nature*, 2003, 425(6953), 98-102; and David P. Rotella, *Nature Reviews Drug Discovery*, 2002, 1(9):674-82].

It is further shown that these structures (Family 1 compounds) have further demonstrated remarkable D4 binding affinity and D4/D2 selectivity, which were maintained also when other heterocyclic cores (compounds of other families) were used, particularly upon manipulating the other moieties in general Formula I (namely, the cyclic amine moiety and the moiety denoted as Y).

In order to explore the effect of the various components in general Formula I on the selective binding to D4, preliminary conformational analyses were performed for the compounds described herein, compared with other D4 ligands taken from available libraries (data not shown).

These studies were based on several publications describing the pharmacophoric binding sites of D4 and ligands having an affinity thereto [see, for example, Komiskey et al. *Proc. Nati. Acad. Sci.* USA, Vol. 75, No. 6, pp. 2641-2643, June 1978; Seiler et al. *Mol. Pharmacol.* 1989 May, 35(5), 643-51; Bostrom et al. *J. Chem. Inf. Comput. Sci.* 2003, 43, 1020-1027; Boeckler et al. *J. Med. Chem.* 2005, 48, 694-709; and Ortore et al. *J. Med. Chem.* 2006, 49, 1397-1407, all being incorporated by reference as if fully set forth herein].

In these studies, it has been suggested that there is a direct correlation between D4 binding affinity and the conformation of the cyclic amine moiety (denoted as the moiety L-Z—X-G in Formula I above). It has been further found that this conformation can be manipulated by interplay between the different heterocyclic moieties and the different "tail" groups (denoted as Y in Formula I), so as to adopt the correct conformation that would provide a precise orientation of a ligand in D4 receptor site.

In order to achieve compounds that would exhibit both enhanced binding to PDE-5 and affinity to D4 receptor, the effect of structural parameters other than the heterocyclic core and the cyclic amine moiety has been explored.

Thus, as shown in Table 2, it has been shown that compounds having a halogen atom (a halo substituent) as Ra in Formula I above favor both D4 and PDE-5 binding (see, for example, Table 2, Compound N123 versus Compound B-72 in Table 2).

Compound having a halogen atom as Rd and/or Rb in Formula I, however, are characterized by somewhat reduced affinity to D4, whereby hydrogens and alkoxy groups as Ra and/or Rb in Formula I favor D4 binding (see, for Example, Table 2, Compounds B-7, N-113 and B-4).

Enhanced PDE-5 inhibition and favorable D4 affinity were also observed in compounds having a short alkyl (e.g., methyl) or halo as Rc in Formula I above (see, for example, Table 2, Compounds B-9 and B-36).

In the cyclic amine linker moiety, data have shown that a protonated form of such a cyclic amine is beneficial for both PDE-5 and D4 binding (see, for example, Table 2, Compound B-14). Substituting the cyclic amine moiety by a bulky group, however, weakens interactions with D4.

As mentioned hereinabove, it has been observed that an aryl or heteroaryl group as Y in Formula I is preferred, and, furthermore, that the substituents of this group play an important role in defining the binding affinity of the compounds to PDE-5 and/or D4.

Thus, for example, an alkoxy group as a substituent at the ortho position with respect to the carbon linked to the cyclic amine was shown to effect both PDE-5 inhibition and D4 agonism, whereby various chain length of the alkoxy group, as well as a benzoxy group, exhibited the same effect.

A similar beneficial effect was also observed with the presence of a nitrogen heteroatom at the same position, in a heteroaryl ring.

A hydroxy group as a substituent at the meta position with respect to the carbon linked to the cyclic amine was also shown to effect both PDE-5 inhibition and D4 agonism.

TABLE 1

| No. | Structure | IUPAC | MW |
|---|---|---|---|
| 101 | 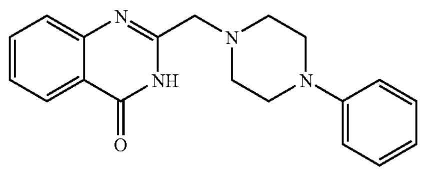 [SMILES: O=c1[nH]c(CN2CCN(c3ccccc3)CC2)nc2ccccc12] | 2-[(4-phenylpiperazin-1-yl)methyl]quinazolin-4(3H)-one | 320.40 |
| 102 | 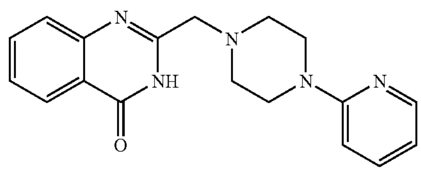 [SMILES: O=c1[nH]c(CN2CCN(c3ccccn3)CC2)nc2ccccc12] | 2-[(4-pyridin-2-ylpiperazin-1-yl)methyl]quinazolin-4(3H)-one | 321.39 |
| 103 | 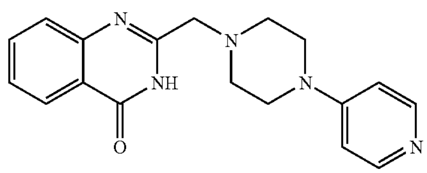 [SMILES: O=c1[nH]c(CN2CCN(c3ccncc3)CC2)nc2ccccc12] | 2-[(4-pyridin-4-ylpiperazin-1-yl)methyl]quinazolin-4(3H)-one | 321.39 |
| 104 | 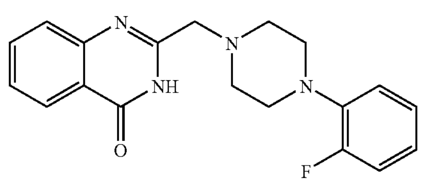 | 2-{[4-(2-fluorophenyl)piperazin-1-yl]methyl}quinazolin-4(3H)-one | 338.39 |
| 105 | 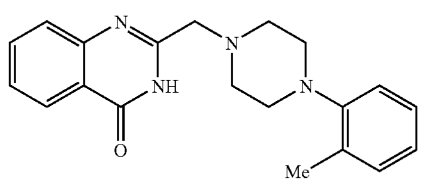 | 2-{[4-(2-methylphenyl)piperazin-1-yl]methyl}quinazolin-4(3H)-one | 334.41 |
| 106 | 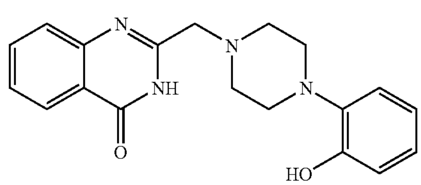 | 2-{[4-(2-hydroxyphenyl)piperazin-1-yl]methyl}quinazolin-4(3H)-one | 336.40 |
| 107 | 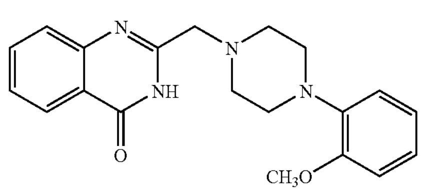 | 2-{[4-(2-methoxyphenyl)piperazin-1-yl]methyl}quinazolin-4(3H)-one | 350.41 |
| 108 | 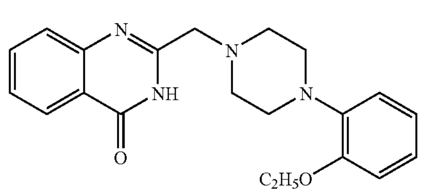 | 2-{[4-(2-ethoxyphenyl)piperazin-1-yl]methyl}quinazolin-4(3H)-one | 364.44 |

TABLE 1-continued

| No. | Structure | IUPAC | MW |
|---|---|---|---|
| 109 | 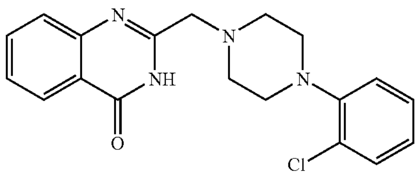 [SMILES: O=c1[nH]c(CN2CCN(c3ccccc3Cl)CC2)nc2ccccc12] | 2-{[4-(2-chlorophenyl)piperazin-1-yl]methyl}quinazolin-4(3H)-one | 354.84 |
| 110 | 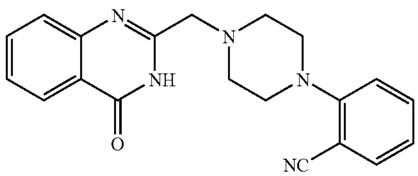 | 2-{4-[(4-oxo-3,4-dihydroquinazolin-2-yl)methyl]piperazin-1-yl}benzonitrile | 345.41 |
| 111 | 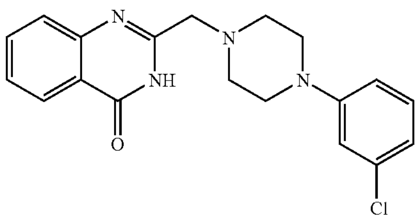 [SMILES: O=c1[nH]c(CN2CCN(c3cccc(Cl)c3)CC2)nc2ccccc12] | 2-{[4-(3-chlorophenyl)piperazin-1-yl]methyl}quinazolin-4(3H)-one | 354.84 |
| 112 | 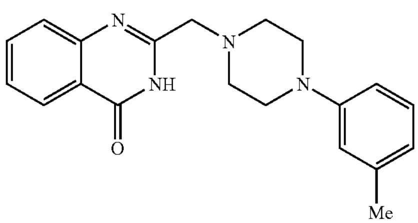 [SMILES: Cc1cccc(N2CCN(Cc3nc4ccccc4c(=O)[nH]3)CC2)c1] | 2-{[4-(3-methylphenyl)piperazin-1-yl]methyl}quinazolin-4(3H)-one | 334.42 |
| 113 | 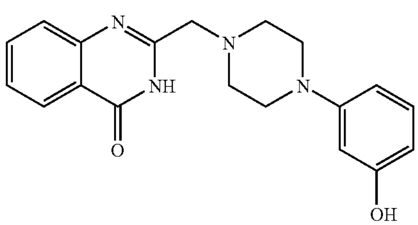 [SMILES: O=c1[nH]c(CN2CCN(c3cccc(O)c3)CC2)nc2ccccc12] | 2-{[4-(3-hydroxyphenyl)piperazin-1-yl]methyl}quinazolin-4(3H)-one | 336.40 |
| 114 | 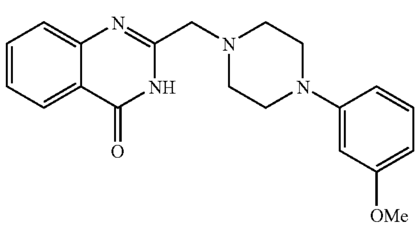 | 2-{[4-(3-methoxyphenyl)piperazin-1-yl]methyl}quinazolin-4(3H)-one | 350.42 |
| 115 | 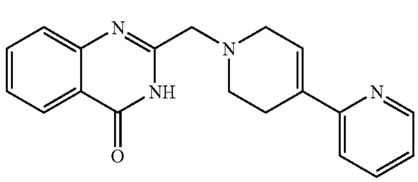 [SMILES: O=c1[nH]c(CN2CC=C(c3ccccn3)CC2)nc2ccccc12] | 2-(3',6'-dihydro-2,4'-bipyridin-1'(2'H)-ylmethyl)quinazolin-4(3H)-one | 318.38 |

TABLE 1-continued

| No. | Structure | IUPAC | MW |
|---|---|---|---|
| 116 | 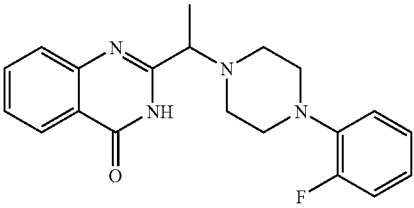 [SMILES: CC(c1nc2ccccc2c(=O)[nH]1)N1CCN(c2ccccc2F)CC1] | 2-{1-[4-(2-fluorophenyl)piperazin-1-yl]ethyl}quinazolin-4(3H)-one | 352.41 |
| 117 | 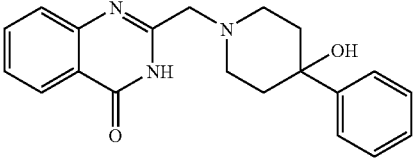 [SMILES: O=c1[nH]c(CN2CCC(O)(c3ccccc3)CC2)nc2ccccc12] | 2-[(4-hydroxy-4-phenylpiperidin-1-yl)methyl]quinazolin-4(3H)-one | 335.41 |
| 118 | 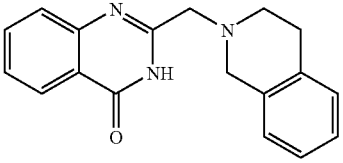 [SMILES: O=c1[nH]c(CN2CCc3ccccc3C2)nc2ccccc12] | 2-(3,4-dihydroisoquinolin-2(1H)-ylmethyl)quinazolin-4(3H)-one | 291.36 |
| 119 | 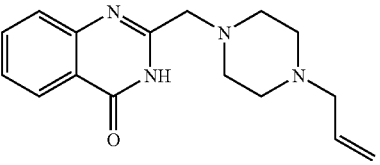 [SMILES: C=CCN1CCN(Cc2nc3ccccc3c(=O)[nH]2)CC1] | 2-[(4-allylpiperazin-1-yl)methyl]quinazolin-4(3H)-one | 284.36 |
| 120 | 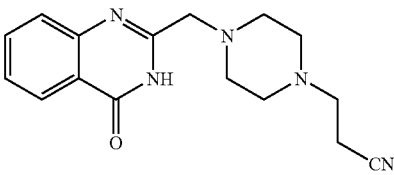 [SMILES: N#CCCN1CCN(Cc2nc3ccccc3c(=O)[nH]2)CC1] | 3-{4-[(4-oxo-3,4-dihydroquinazolin-2-yl)methyl]piperazin-1-yl}propanenitrile | 297.36 |
| 121 | 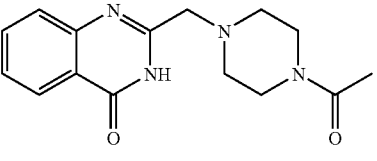 [SMILES: CC(=O)N1CCN(Cc2nc3ccccc3c(=O)[nH]2)CC1] | 2-[(4-acetylpiperazin-1-yl)methyl]quinazolin-4(3H)-one | 286.34 |
| 122 | 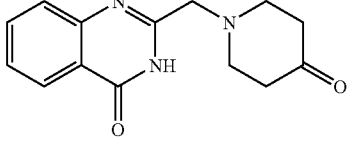 | 2-[(4-oxopiperidin-1-yl)methyl]quinazolin-4(3H)-one | 257.29 |
| 123 | 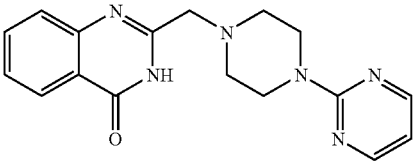 [SMILES: O=c1[nH]c(CN2CCN(c3ncccn3)CC2)nc2ccccc12] | 2-[(4-pyrimidin-2-ylpiperazin-1-yl)methyl]quinazolin-4(3H)-one | 322.37 |

TABLE 1-continued

| No. | Structure | IUPAC | MW |
|---|---|---|---|
| 124 | 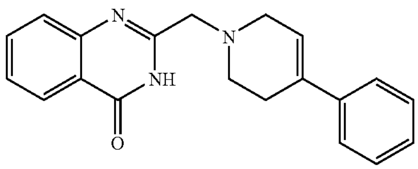 | 2-[(4-phenyl-3,6-dihydropyridin-1(2H)-yl)methyl]quinazolin-4(3H)-one | 317.39 |
| 125 | 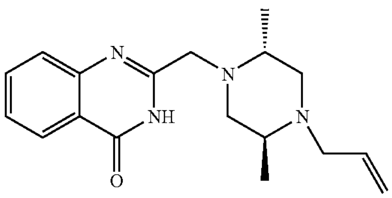 [SMILES: C=CCN1C[C@@H](C)N(Cc2nc3ccccc3c(=O)[nH]2)C[C@@H]1C] | 2-{[(2R,5S)-4-allyl-2,5-dimethylpiperazin-1-yl]methyl}quinazolin-4(3H)-one | 312.42 |
| 126 | 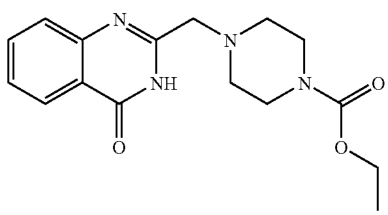 [SMILES: CCOC(=O)N1CCN(Cc2nc3ccccc3c(=O)[nH]2)CC1] | ethyl 4-[(4-oxo-3,4-dihydroquinazolin-2-yl)methyl]piperazine-1-carboxylate | 316.36 |
| 127 | 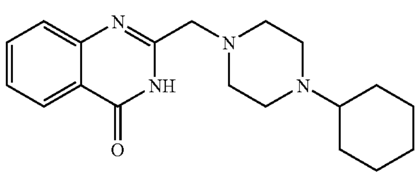 [SMILES: O=c1[nH]c(CN2CCN(C3CCCCC3)CC2)nc2ccccc12] | 2-[(4-cyclohexylpiperazin-1-yl)methyl]quinazolin-4(3H)-one | 326.45 |
| 128 | 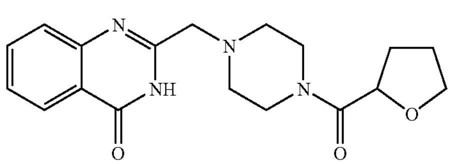 [SMILES: O=C(C1CCCO1)N1CCN(Cc2nc3ccccc3c(=O)[nH]2)CC1] | 2-{[4-(tetrahydrofuran-2-ylcarbonyl)piperazin-1-yl]methyl}quinazolin-4(3H)-one | 342.40 |
| 129 | 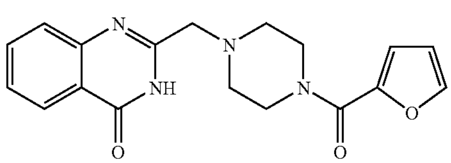 [SMILES: O=C(c1ccco1)N1CCN(Cc2nc3ccccc3c(=O)[nH]2)CC1] | 2-{[4-(2-furoyl)piperazin-1-yl]methyl}quinazolin-4(3H)-one | 338.37 |
| 130 | 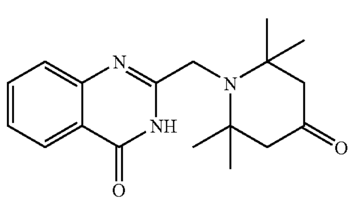 [SMILES: CC1(C)CC(=O)CC(C)(C)N1Cc1nc2ccccc2c(=O)[nH]1] | 2-[(2,2,6,6-tetramethyl-4-oxopiperidin-1-yl)methyl]quinazolin-4(3H)-one | 313.40 |
| 201 | 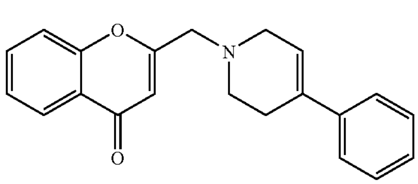 [SMILES: O=c1cc(CN2CC=C(c3ccccc3)CC2)oc2ccccc12] | 2-[(4-phenyl-3,6-dihydropyridin-1(2H)-yl)methyl]-4H-chromen-4-one | 317.39 |

TABLE 1-continued

| No. | Structure | IUPAC | MW |
|---|---|---|---|
| 202 | 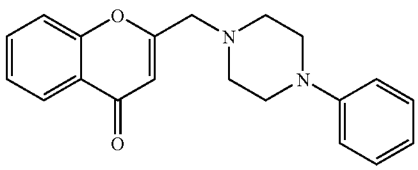 [SMILES: O=c1cc(CN2CCN(c3ccccc3)CC2)oc2ccccc12] | 2-[(4-phenylpiperazin-1-yl)methyl]-4H-chromen-4-one | 320.39 |
| 203 | 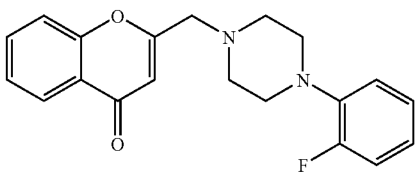 [SMILES: O=c1cc(CN2CCN(c3ccccc3F)CC2)oc2ccccc12] | 2-{[4-(2-fluorophenyl)piperazin-1-yl]methyl}-4H-chromen-4-one | 338.39 |
| 204 | 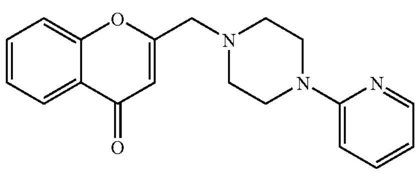 [SMILES: O=c1cc(CN2CCN(c3ccccn3)CC2)oc2ccccc12] | 2-[(4-pyridin-2-ylpiperazin-1-yl)methyl]-4H-chromen-4-one | 321.38 |
| 205 | 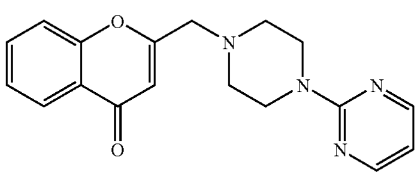 | 2-[(4-pyrimidin-2-ylpiperazin-1-yl)methyl]-4H-chromen-4-one | 322.37 |
| 206 | 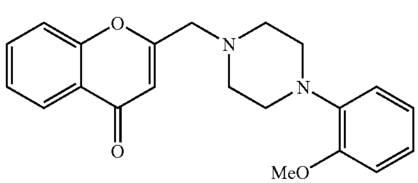 [SMILES: COc1ccccc1N1CCN(Cc2cc(=O)c3ccccc3o2)CC1] | 2-{[4-(2-methoxyphenyl)piperazin-1-yl]methyl}-4H-chromen-4-one | 350.42 |
| 207 | 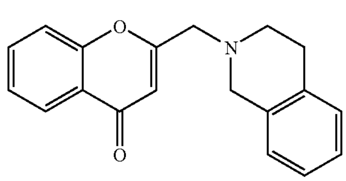 [SMILES: O=c1cc(CN2CCc3ccccc3C2)oc2ccccc12] | 2-(3,4-dihydroisoquinolin-2(1H)-ylmethyl)-4H-chromen-4-one | 291.35 |
| 301 | 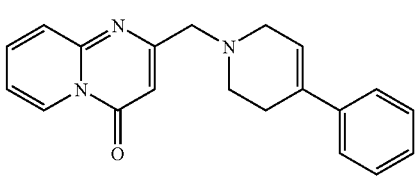 [SMILES: O=c1cc(CN2CC=C(c3ccccc3)CC2)nc2ccccn12] | 2-[(4-phenyl-3,6-dihydropyridin-1(2H)-yl)methyl]-4H-pyrido[1,2-a]pyrimidin-4-one | 317.39 |
| 302 | 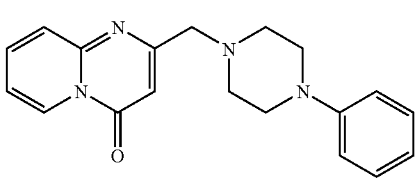 [SMILES: O=c1cc(CN2CCN(c3ccccc3)CC2)nc2ccccn12] | 2-[(4-phenylpiperazin-1-yl)methyl]-4H-pyrido[1,2-a]pyrimidin-4-one | 320.40 |

TABLE 1-continued

| No. | Structure | IUPAC | MW |
|---|---|---|---|
| 303 | 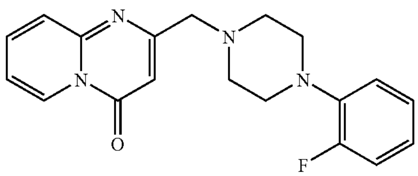 [SMILES: O=c1cc(CN2CCN(c3ccccc3F)CC2)nc2ccccn12] | 2-{[4-(2-fluorophenyl)piperazin-1-yl]methyl}-4H-pyrido[1,2-a]pyrimidin-4-one | 338.39 |
| 304 | 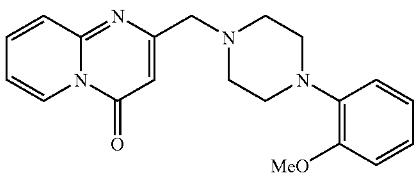 [SMILES: COc1ccccc1N1CCN(Cc2cc(=O)n3ccccc3n2)CC1] | 2-{[4-(2-methoxyphenyl)piperazin-1-yl]methyl}-4H-pyrido[1,2-a]pyrimidin-4-one | 350.42 |
| 305 | 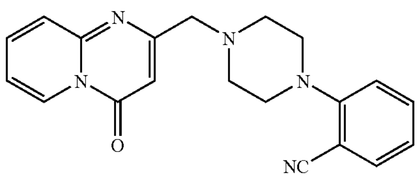 | 2-{4-[(4-oxo-4H-pyrido[1,2-a]pyrimidin-2-yl)methyl]piperazin-1-yl}benzonitrile | 345.41 |
| 306 | 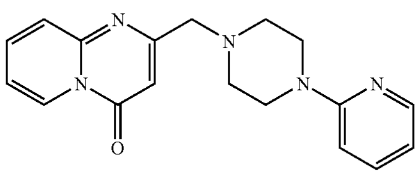 [SMILES: O=c1cc(CN2CCN(c3ccccn3)CC2)nc2ccccn12] | 2-[(4-pyridin-2-ylpiperazin-1-yl)methyl]-4H-pyrido[1,2-a]pyrimidin-4-one | 321.39 |
| 307 | 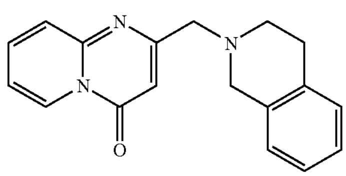 [SMILES: O=c1cc(CN2CCc3ccccc3C2)nc2ccccn12] | 2-(3,4-dihydroisoquinolin-2(1H)-ylmethyl)-4H-pyrido[1,2-a]pyrimidin-4-one | 291.36 |
| 401 | 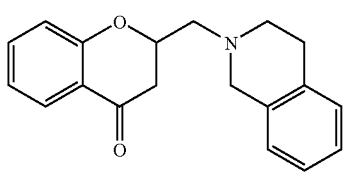 [SMILES: O=C1CC(CN2CCc3ccccc3C2)Oc2ccccc21] | 2-(3,4-dihydroisoquinolin-2(1H)-ylmethyl)-2,3-dihydro-4H-chromen-4-one | 293.37 |
| 402 | 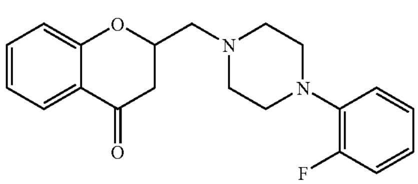 [SMILES: O=C1CC(CN2CCN(c3ccccc3F)CC2)Oc2ccccc21] | 2-{[4-(2-fluorophenyl)piperazin-1-yl]methyl}-2,3-dihydro-4H-chromen-4-one | 340.40 |
| 403 | 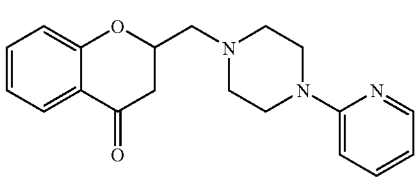 [SMILES: O=C1CC(CN2CCN(c3ccccn3)CC2)Oc2ccccc21] | 2-[(4-pyridin-2-ylpiperazin-1-yl)methyl]-2,3-dihydro-4H-chromen-4-one | 323.40 |

TABLE 1-continued

| No. | Structure | IUPAC | MW |
|---|---|---|---|
| 404 | 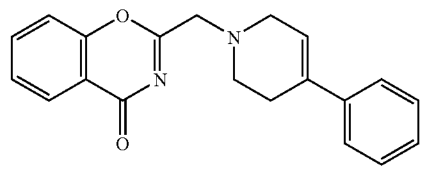 [SMILES: O=c1nc(CN2CC=C(c3ccccc3)CC2)oc2ccccc12] | 2-[(4-phenyl-3,6-dihydropyridin-1(2H)-yl)methyl]-4H-1,3-benzoxazin-4-one | 318.38 |
| 405 | BF6 | 3-[(4-oxo-3,4-dihydroquinazolin-2-yl)methyl]-1-phenyl-1H-imidazol-3-ium | 319.39 |
| 408 | 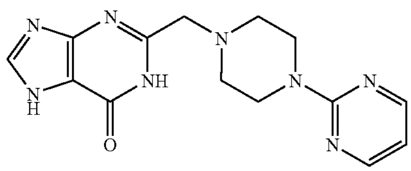 [SMILES: O=c1[nH]c(CN2CCN(c3ncccn3)CC2)nc2nc[nH]c12] | 2-((4-(pyrimidin-2-yl)piperazin-1-yl)methyl)-1H-purin-6(7H)-one | 312.33 |
| 409 | 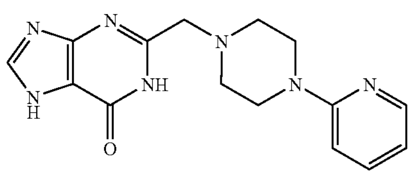 [SMILES: O=c1[nH]c(CN2CCN(c3ccccn3)CC2)nc2nc[nH]c12] | 2-((4-(pyridin-2-yl)piperazin-1-yl)methyl)-1H-purin-6(7H)-one | 311.34 |
| 501 | 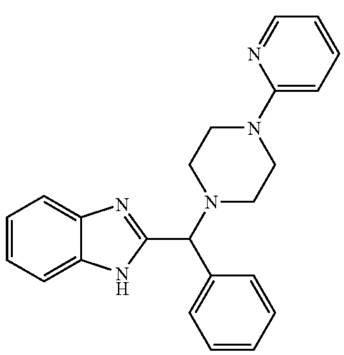 [SMILES: c1ccc(C(c2nc3ccccc3[nH]2)N2CCN(c3ccccn3)CC2)cc1] | 2-(phenyl(4-(pyridin-2-yl)piperazin-1-yl)methyl)-1H-benzo[d]imidazole | 369.47 |
| 502 | 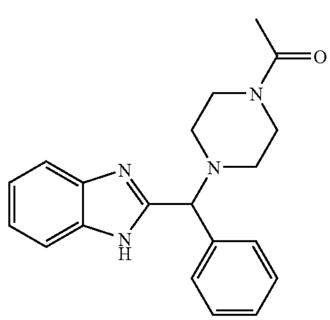 [SMILES: CC(=O)N1CCN(C(c2ccccc2)c2nc3ccccc3[nH]2)CC1] | 2-[(4-acetylpiperazin-1-yl)(phenyl)methyl]-1H-benzimidazole | 334.42 |

TABLE 1-continued

| No. | Structure | IUPAC | MW |
|---|---|---|---|
| 503 | 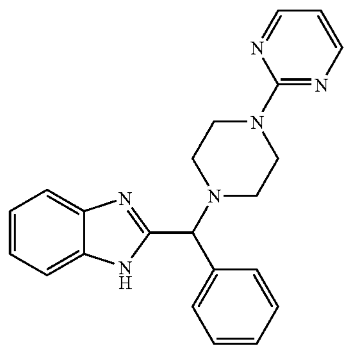 | 2-[phenyl(4-pyrimidin-2-ylpiperazin-1-yl)methyl]-1H-benzimidazole | 370.46 |
| 504 | 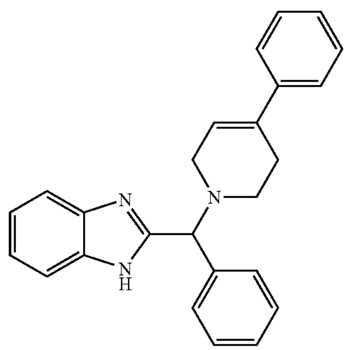 [SMILES: C1=C(c2ccccc2)CCN(C(c2ccccc2)c2nc3ccccc3[nH]2)C1] | 2-((5,6-dihydro-4-phenylpyridin-1(2H)-yl)(phenyl)methyl)-1H-benzo[d]imidazole | 365.48 |
| 505 | 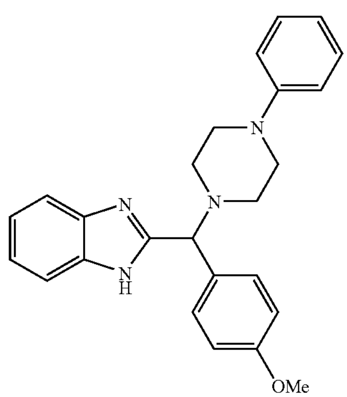 [SMILES: COc1ccc(C(c2nc3ccccc3[nH]2)N2CCN(c3ccccc3)CC2)cc1] | 2-((4-methoxyphenyl)(4-phenylpiperazin-1-yl)methyl)-1H-benzo[d]imidazole | 398.51 |
| 506 | 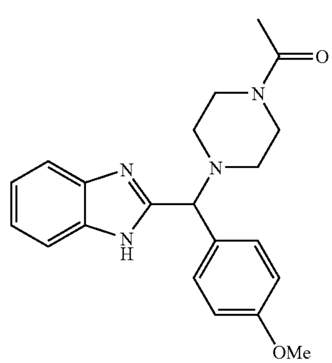 [SMILES: COc1ccc(C(c2nc3ccccc3[nH]2)N2CCN(C(C)=O)CC2)cc1] | 1-(4-((1H-benzo[d]imidazol-2-yl)(4-methoxyphenyl)methyl)piperazin-1-yl)ethanone | 364.45 |

TABLE 1-continued

| No. | Structure | IUPAC | MW |
|---|---|---|---|
| 507 | 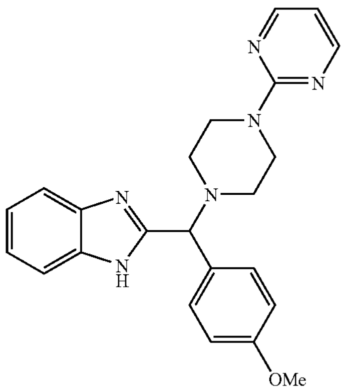 [SMILES: COc1ccc(C(c2nc3ccccc3[nH]2)N2CCN(c3ncccn3)CC2)cc1] | 2-((4-methoxyphenyl)(4-(pyrimidin-2-yl)piperazin-1-yl)methyl)-1H-benzo[d]imidazole | 400.49 |
| 508 | 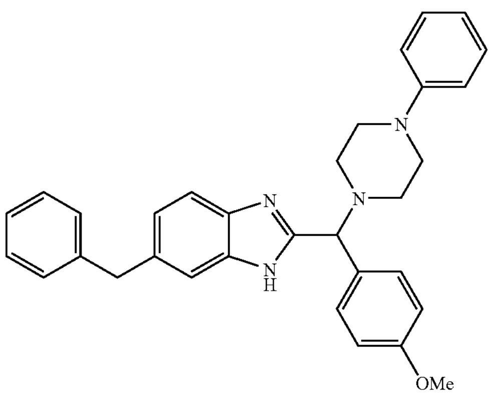 [SMILES: COc1ccc(C(c2nc3ccc(Cc4ccccc4)cc3[nH]2)N2CCN(c3ccccc3)CC2)cc1] | 6-benzyl-2-((4-methoxyphenyl)(4-phenylpiperazin-1-yl)methyl)-1H-benzo[d]imidazole | 488.64 |
| 509 | 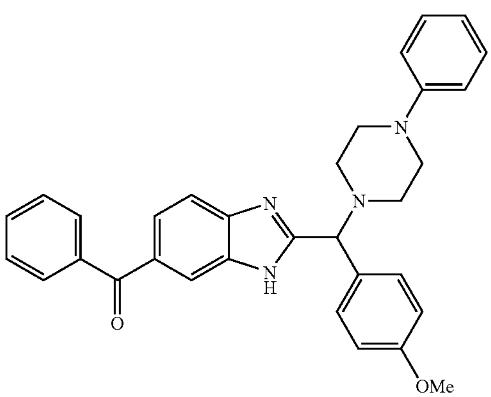 [SMILES: COc1ccc(C(c2nc3ccc(C(=O)c4ccccc4)cc3[nH]2)N2CCN(c3ccccc3)CC2)cc1] | (2-((4-methoxyphenyl)(4-phenylpiperazin-1-yl)methyl)-1H-benzo[d]imidazol-6-yl)(phenyl)methanone | 502.62 |
| 510 | 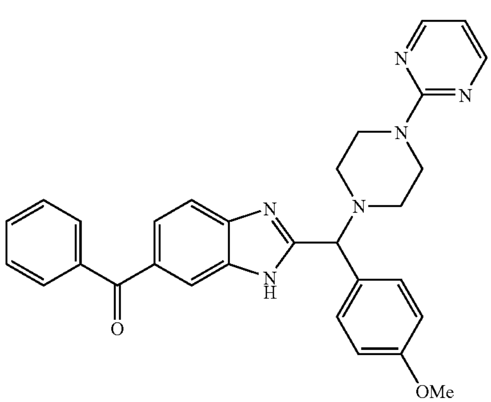 [SMILES: COc1ccc(C(c2nc3ccc(C(=O)c4ccccc4)cc3[nH]2)N2CCN(c3ncccn3)CC2)cc1] | (2-((4-methoxyphenyl)(4-(pyrimidin-2-yl)piperazin-1-yl)methyl)-1H-benzo[d]imidazol-6-yl)(phenyl)methanone | 504.60⁻ |

TABLE 1-continued

| No. | Structure | IUPAC | MW |
|---|---|---|---|
| 511 | 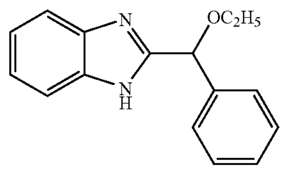 [SMILES: CCOC(c1ccccc1)c1nc2ccccc2[nH]1] | 2-(1-phenylethyl)-1H-benzimidazole | 222.29 |
| 801 | 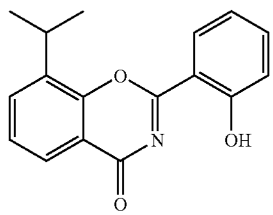 [SMILES: CC(C)c1cccc2c(=O)nc(-c3ccccc3O)oc12] | 2-(2-hydroxyphenyl)-8-isopropyl-4H-1,3-benzoxazin-4-one | 281.31 |
| B-4 | 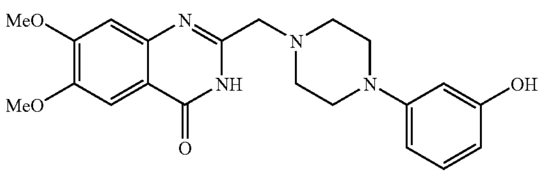 [SMILES: COc1cc2nc(CN3CCN(c4cccc(O)c4)CC3)[nH]c(=O)c2cc1OC] | 2-((4-(3-hydroxyphenyl)piperazin-1-yl)methyl)-6,7-dimethoxyquinazolin-4(3H)-one | 396.44 |
| B-8 | 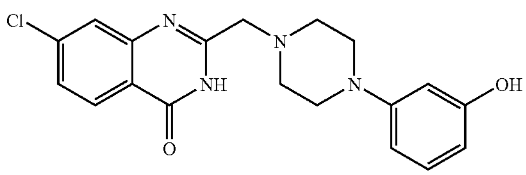 [SMILES: O=c1[nH]c(CN2CCN(c3cccc(O)c3)CC2)nc2cc(Cl)ccc12] | 7-chloro-2-((4-(3-hydroxyphenyl)piperazin-1-yl)methyl)quinazolin-4(3H)-one | 370.83 |
| B-9 | 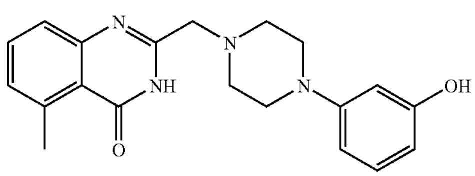 [SMILES: Cc1cccc2nc(CN3CCN(c4cccc(O)c4)CC3)[nH]c(=O)c12] | 2-((4-(3-hydroxyphenyl)piperazin-1-yl)methyl)-5-methylquinazolin-4(3H)-one | 350.41 |
| B-10 | 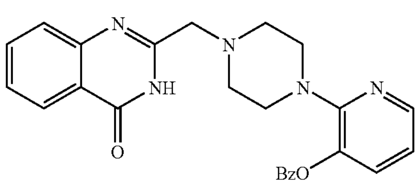 | 2-((4-(3-(benzyloxy)pyridin-2-yl)piperazin-1-yl)methyl)quinazolin-4(3H)-one | 427.5 |
| B-11 | 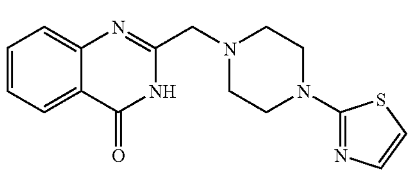 [SMILES: O=c1[nH]c(CN2CCN(c3nccs3)CC2)nc2ccccc12] | 2-((4-(thiazol-2-yl)piperazin-1-yl)methyl)quinazolin-4(3H)-one | 327.4 |
| B-13 | 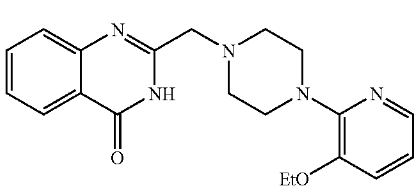 | 2-((4-(3-ethoxypyridin-2-yl)piperazin-1-yl)methyl)quinazolin-4(3H)-one | 365.43 |

TABLE 1-continued

| No. | Structure | IUPAC | MW |
|---|---|---|---|
| B-14 | 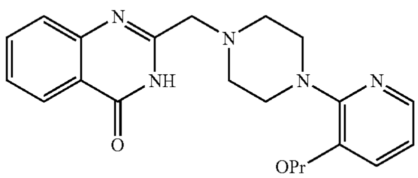 | 2-((4-(3-propoxypyridin-2-yl)piperazin-1-yl)methyl)quinazolin-4(3H)-one | 379.46 |
| B-31 | 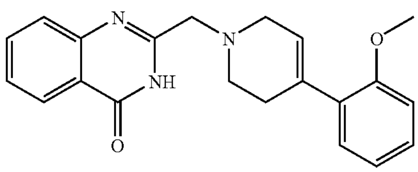 [SMILES: COc1ccccc1C1=CCN(Cc2nc3ccccc3c(=O)[nH]2)CC1] | 2-((5,6-dihydro-4-(2-methoxyphenyl)pyridin-1(2H)-yl)methyl)quinazolin-4(3H)-one | 347.41 |
| B-33 | 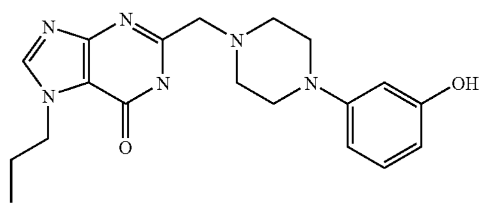 [SMILES: CCCn1cnc2nc(CN3CCN(c4cccc(O)c4)CC3)[nH]c(=O)c21] | 2-((4-(3-hydroxyphenyl)piperazin-1-yl)methyl)-7-propyl-1H-purin-6(7H)-one | 368.43 |
| B-34 | 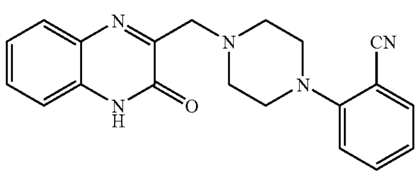 [SMILES: N#Cc1ccccc1N1CCN(Cc2nc3ccccc3[nH]c2=O)CC1] | 2-(4-((1,2-dihydro-2-oxoquinoxalin-3-yl)methyl)piperazin-1-yl)benzonitrile | 345.40 |
| B-36 | 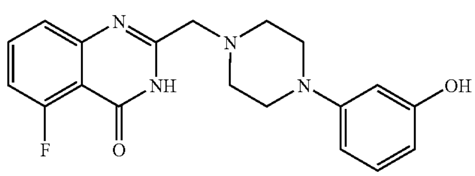 | 5-fluoro-2-((4-(3-hydroxyphenyl)piperazin-1-yl)methyl)quinazolin-4(3H)-one | 354.38 |
| B-37 | 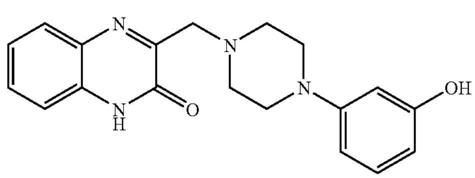 [SMILES: O=c1[nH]c2ccccc2nc1CN1CCN(c2cccc(O)c2)CC1] | 3-((4-(3-hydroxyphenyl)piperazin-1-yl)methyl)quinoxalin-2(1H)-one | 336.39 |
| B-38 | 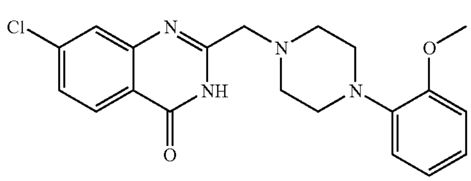 [SMILES: COc1ccccc1N1CCN(Cc2nc3cc(Cl)ccc3c(=O)[nH]2)CC1] | 7-chloro-2-((4-(2-methoxyphenyl)piperazin-1-yl)methyl)quinazolin-4(3H)-one | 384.86 |
| B-39 | 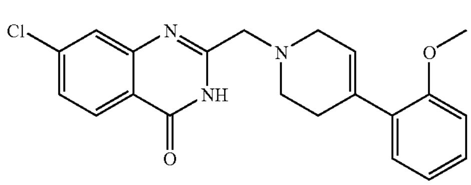 [SMILES: COc1ccccc1C1=CCN(Cc2nc3cc(Cl)ccc3c(=O)[nH]2)CC1] | 7-chloro-2-((5,6-dihydro-4-(2-methoxyphenyl)pyridin-1(2H)-yl)methyl)quinazolin-4(3H)-one | 381.86 |

TABLE 1-continued

| No. | Structure | IUPAC | MW |
|---|---|---|---|
| B-42 | 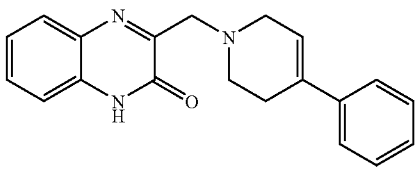 [SMILES: O=c1[nH]c2ccccc2nc1CN1CC=C(c2ccccc2)CC1] | 3-((5,6-dihydro-4-phenylpyridin-1(2H)-yl)methyl)quinoxalin-2(1H)-one | 317.38 |
| B-43 | 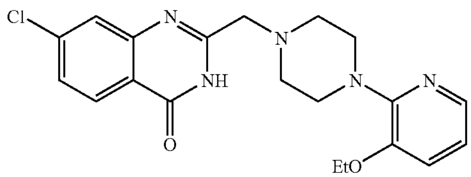 [SMILES: CCOc1cccnc1N1CCN(Cc2nc3cc(Cl)ccc3c(=O)[nH]2)CC1] | 7-chloro-2-((4-(3-ethoxypyridin-2-yl)piperazin-1-yl)methyl)quinazolin-4(3H)-one | 399.87 |
| B-44 | 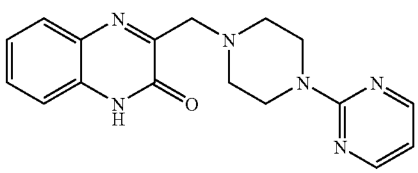 [SMILES: O=c1[nH]c2ccccc2nc1CN1CCN(c2ncccn2)CC1] | 3-((4-(pyrimidin-2-yl)piperazin-1-yl)methyl)quinoxalin-2(1H)-one | 322.36 |
| B-45 | 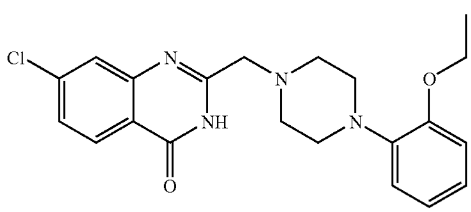 [SMILES: CCOc1ccccc1N1CCN(Cc2nc3cc(Cl)ccc3c(=O)[nH]2)CC1] | 7-chloro-2-((4-(2-ethoxyphenyl)piperazin-1-yl)methyl)quinazolin-4(3H)-one | 398.89 |
| B-47 | 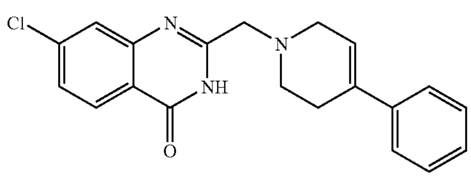 [SMILES: O=c1[nH]c(CN2CC=C(c3ccccc3)CC2)nc2cc(Cl)ccc12] | 7-chloro-2-((5,6-dihydro-4-phenylpyridin-1(2H)-yl)methyl)quinazolin-4(3H)-one | 351.83 |
| B-51 | 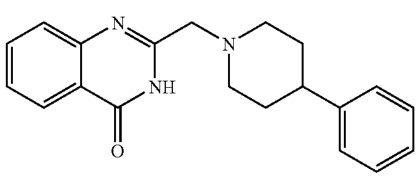 [SMILES: O=c1[nH]c(CN2CCC(c3ccccc3)CC2)nc2ccccc12] | 2-((4-phenylpiperidin-1-yl)methyl)quinazolin-4(3H)-one | 319.40 |
| B-71 | 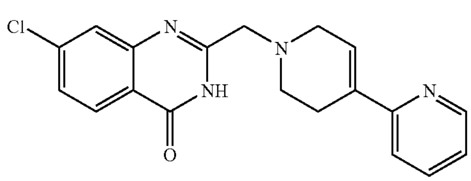 | 7-chloro-2-((5,6-dihydro-4-(pyridin-2-yl)pyridin-1(2H)-yl)methyl)quinazolin-4(3H)-one | 352.82 |
| B-72 | 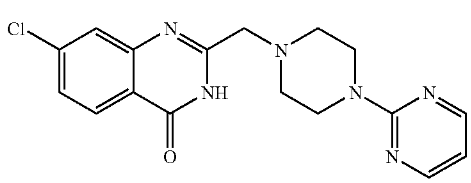 [SMILES: O=c1[nH]c(CN2CCN(c3ncccn3)CC2)nc2cc(Cl)ccc12] | 7-chloro-2-((4-(pyrimidin-2-yl)piperazin-1-yl)methyl)quinazolin-4(3H)-one | 356.81 |

TABLE 1-continued

| No. | Structure | IUPAC | MW |
|---|---|---|---|
| B-75 | 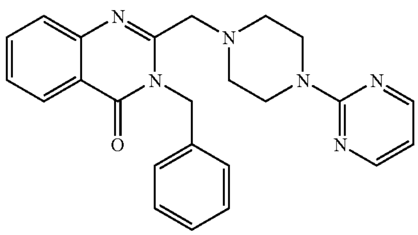 [SMILES: O=c1c2ccccc2nc(CN2CCN(c3ncccn3)CC2)n1Cc1ccccc1] | 3-benzyl-2-((4-(pyrimidin-2-yl)piperazin-1-yl)methyl)quinazolin-4(3H)-one | 412.49 |
| B-82 | 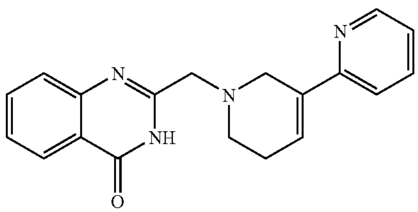 [SMILES: O=c1[nH]c(CN2CCC=C(c3ccccn3)C2)nc2ccccc12] | 2-((5,6-dihydro-3-(pyridin-2-yl)pyridin-1(2H)-yl)methyl)quinazolin-4(3H)-one | 318.37 |
| B-83 | 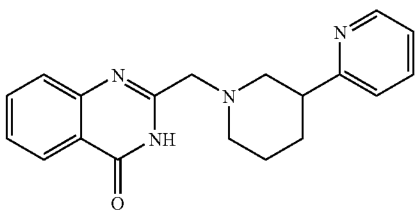 [SMILES: O=c1[nH]c(CN2CCCC(c3ccccn3)C2)nc2ccccc12] | 2-((3-(pyridin-2-yl)piperidin-1-yl)methyl)quinazolin-4(3H)-one | 320.39 |
| Xan-1 | | 1,3-diethyl-8-((4-(3-hydroxyphenyl)piperazin-1-yl)methyl)-1H-purine-2,6(3H,7H)-dione | 398.46 |
| Xan-1 | | 1,3-diethyl-8-((4-(3-hydroxyphenyl)piperazin-1-yl)methyl)-1H-purine-2,6(3H,7H)-dione | 398.46 |

TABLE 2

| No. | Structure | D4.4(h) Competitive Binding, % at 5 mcM | D4.4(h) GTPgammaS$^{35}$ Cellular Assay, Agonist Response, % | D4/D2 Selectivity | PDE5 % inhibition at 50 mcM | IC50, $10^{-6}$ M |
|---|---|---|---|---|---|---|
| B-14 | | 81 | ND | ND | 70 | 9 |

TABLE 2-continued

| No. | Structure | D4.4(h) Competitive Binding, % at 5 mcM | GTPgammaS$^{35}$ Cellular Assay, Agonist Response, % | D4/D2 Selectivity | PDE5 % inhibition at 50 mcM | IC50, $10^{-6}$ M |
|---|---|---|---|---|---|---|
| B-72 | 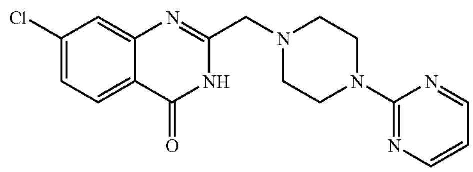 [SMILES: O=c1[nH]c(CN2CCN(c3ncccn3)CC2)nc2cc(Cl)ccc12] | 70 | ND | ND | 62 | 2 |
| B-39 | 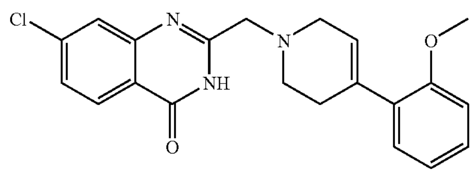 [SMILES: COc1ccccc1C1=CCN(Cc2nc3cc(Cl)ccc3c(=O)[nH]2)CC1] | 95 | ND | ND | ND | ND |
| B-4 | 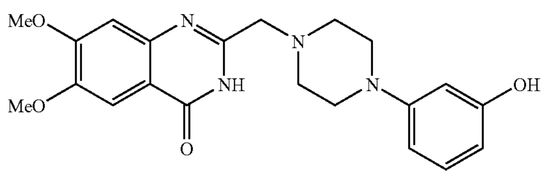 [SMILES: COc1cc2nc(CN3CCN(c4cccc(O)c4)CC3)[nH]c(=O)c2cc1OC] | 91 | ND | ND | 25 | active |
| B-8 | 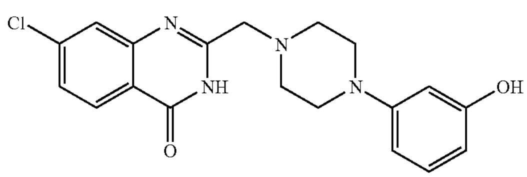 [SMILES: O=c1[nH]c(CN2CCN(c3cccc(O)c3)CC2)nc2cc(Cl)ccc12] | 90 | ND | ND | 28 | active |
| B-9 | 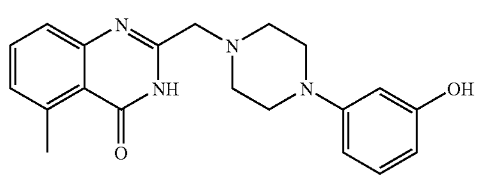 [SMILES: Cc1cccc2nc(CN3CCN(c4cccc(O)c4)CC3)[nH]c(=O)c12] | 89 | ND | ND | 47 | active |
| B-51 | 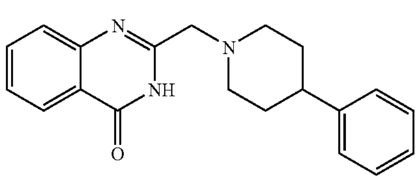 [SMILES: O=c1[nH]c(CN2CCC(c3ccccc3)CC2)nc2ccccc12] | 88 | ND | ND | ND | ND |
| B-3 | 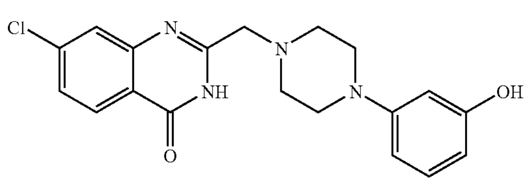 [SMILES: O=c1[nH]c(CN2CCN(c3cccc(O)c3)CC2)nc2cc(Cl)ccc12] | 82 | ND | ND | ND | ND |
| 113 | 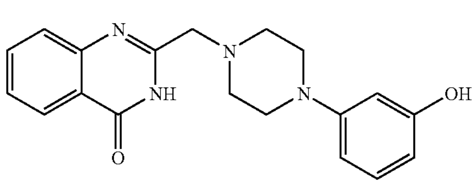 [SMILES: O=c1[nH]c(CN2CCN(c3cccc(O)c3)CC2)nc2ccccc12] | 91 | 42 | ~50 | ND | 20 |

TABLE 2-continued

| No. | Structure | D4.4(h) Competitive Binding, % at 5 mcM | GTPgammaS$^{35}$ Cellular Assay, Agonist Response, % | D4/D2 Selectivity | PDE5 % inhibition at 50 mcM | IC50, $10^{-6}$ M |
|---|---|---|---|---|---|---|
| 108 | 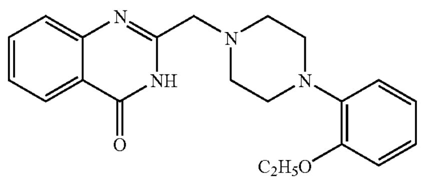 | 93 | 49 | >100 | ND | ND |
| 107 | 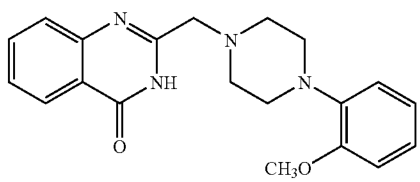 | 88 | 44 | >70 | ND | ND |
| B-13 | 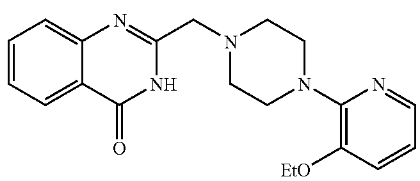 [SMILES: CCOc1cccnc1N1CCN(Cc2nc3ccccc3c(=O)[nH]2)CC1] | 86 | ND | ND | ND | ND |
| B-34 | 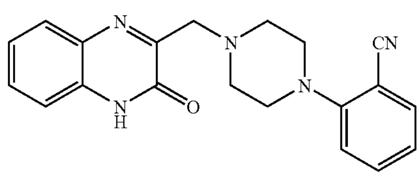 [SMILES: N#Cc1ccccc1N1CCN(Cc2nc3ccccc3[nH]c2=O)CC1] | 84 | ND | ND | ND | ND |
| B-36 | 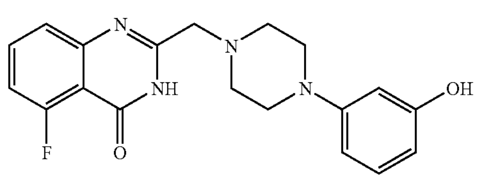 | 82 | ND | ND | ND | ND |
| B-31 | 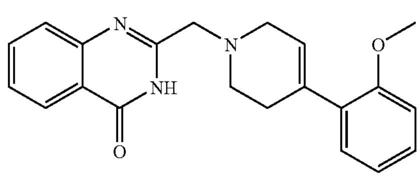 [SMILES: COc1ccccc1C1=CCN(Cc2nc3ccccc3c(=O)[nH]2)CC1] | 74 | ND | ND | ND | ND |
| B-42 | 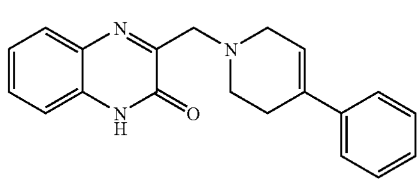 [SMILES: O=c1[nH]c2ccccc2nc1CN1CC=C(c2ccccc2)CC1] | 62 | ND | ND | ND | ND |
| B-38 | 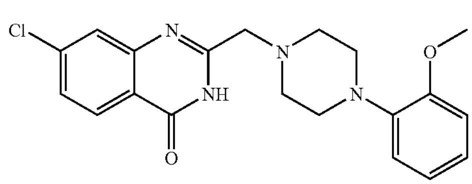 | 65 | ND | ND | ND | ND |

TABLE 2-continued
| No. | Structure | Competitive Binding, % at 5 mcM | D4.4(h) GTPgammaS35 Cellular Assay, Agonist Response, % | D4/D2 Selectivity | PDE5 % inhibition at 50 mcM | IC50, 10⁻⁶ M |
|---|---|---|---|---|---|---|
| B-47 | 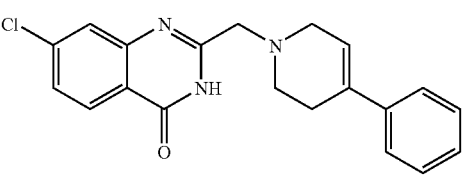 | 63 | ND | ND | ND | ND |
| B-37 | 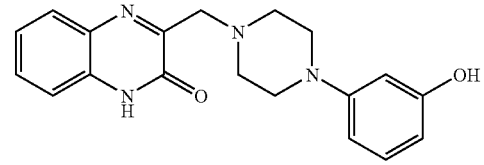 [SMILES: O=c1[nH]c2ccccc2nc1CN1CCN(c2cccc(O)c2)CC1] | 62 | ND | ND | ND | ND |
| 115 | 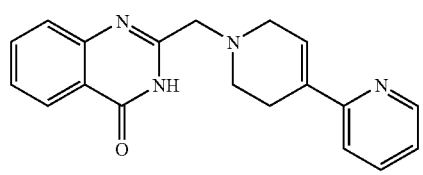 [SMILES: O=c1[nH]c(CN2CC=C(c3ccccn3)CC2)nc2ccccc12] | 66 | ND | ND | ND | ND |
| B-10 | 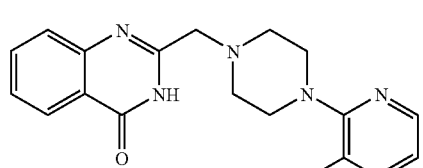 | 60 | ND | ND | 40 | active |
| B-83 | 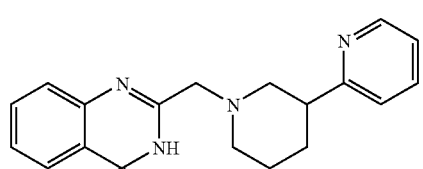 | 57 | ND | ND | ND | ND |
| Xan1 | 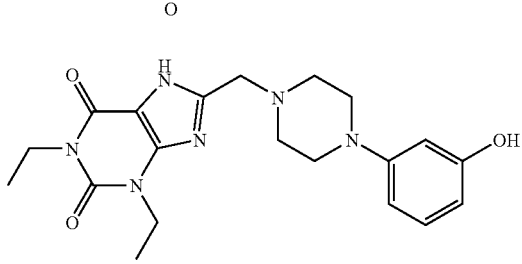 | 54 | ND | ND | ND | ND |
| Xan2 | 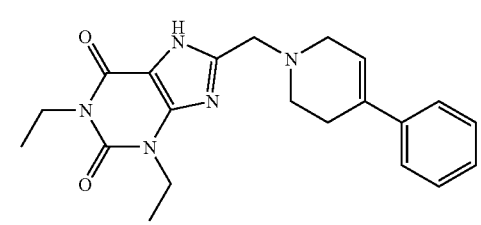 [SMILES: CCn1c(=O)c2[nH]c(CN3CC=C(c4ccccc4)CC3)nc2n(CC)c1=O] | 25 | ND | ND | ND | ND |

TABLE 2-continued
| No. | Structure | D4.4(h) Competitive Binding, % at 5 mcM | GTPgammaS35 Cellular Assay, Agonist Response, % | D4/D2 Selectivity | PDE5 % inhibition at 50 mcM | IC50, 10⁻⁶ M |
|---|---|---|---|---|---|---|
| 104 | 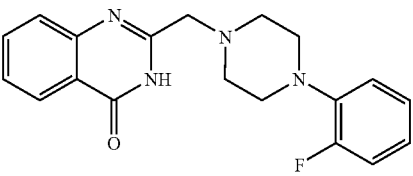 [SMILES: O=c1[nH]c(CN2CCN(c3ccccc3F)CC2)nc2ccccc12] | 59 | 62 | >100 | ND | ND |
| 109 | 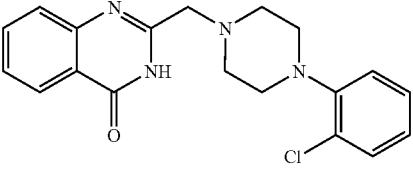 | 57 | 54 | >100 | ND | ND |
| 110 | 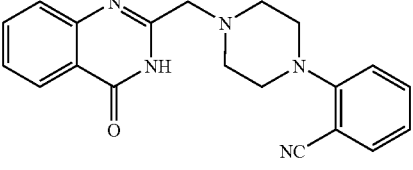 | 52 | 69 | >500 | ND | ND |
| 124 | 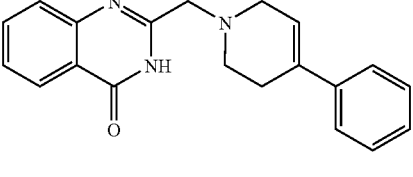 | 73 | 57 | ~85 | ND | ND |
| 301 | 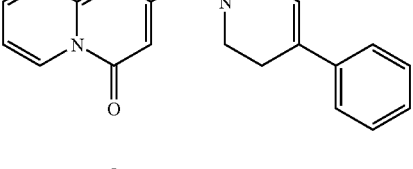 | 59 | 69 | ~10 | ND | ND |
| 201 | 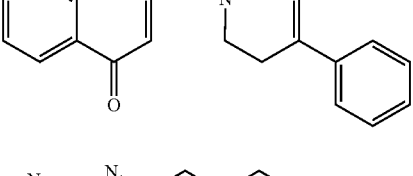 | 72 | 75 | ~10 | ND | ND |
| 408 | 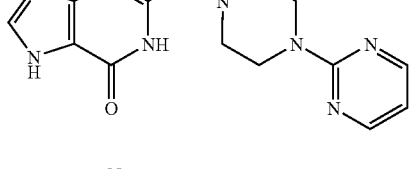 | 33 | ND | ND | 32 | active |
| B-44 | 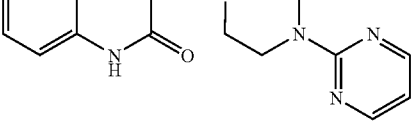 | 29 | ND | ND | ND | ND |

TABLE 2-continued

| No. | Structure | D4.4(h) Competitive Binding, % at 5 mcM | D4.4(h) GTPgammaS³⁵ Cellular Assay, Agonist Response, % | D4/D2 Selectivity | PDE5 % inhibition at 50 mcM | IC50, 10⁻⁶ M |
|---|---|---|---|---|---|---|
| B-45 | 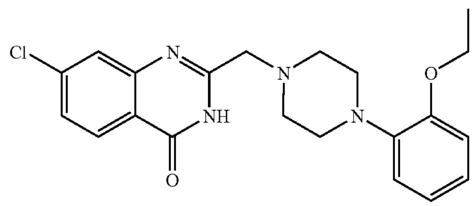 [SMILES: CCOc1ccccc1N1CCN(Cc2nc3cc(Cl)ccc3c(=O)[nH]2)CC1] | 46 | ND | ND | ND | ND |
| B-71 | 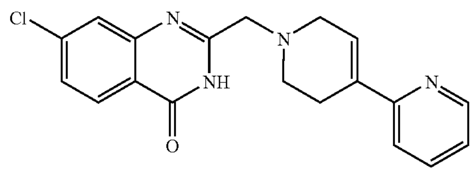 [SMILES: O=c1[nH]c(CN2CC=C(c3ccccn3)CC2)nc2cc(Cl)ccc12] | ND | ND | ND | 63 | 27 |
| 123 | 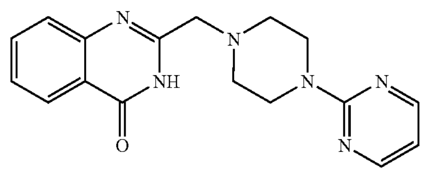 [SMILES: O=c1[nH]c(CN2CCN(c3ncccn3)CC2)nc2ccccc12] | 13 | ND | ND | 61 | 26 |
| 102 | 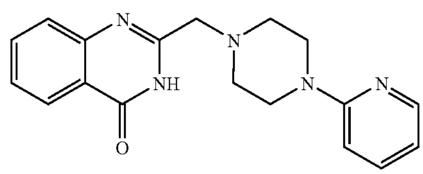 [SMILES: O=c1[nH]c(CN2CCN(c3ccccn3)CC2)nc2ccccc12] | na | na | ND | 29 | active |
| B-11 | 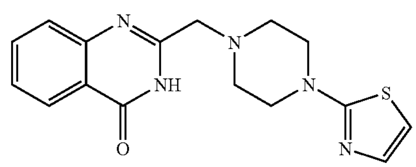 [SMILES: O=c1[nH]c(CN2CCN(c3nccs3)CC2)nc2ccccc12] | 18 | ND | ND | 68 | 2 |
| B-75 | 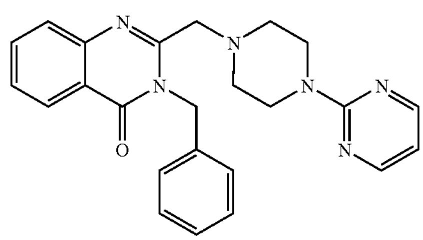 [SMILES: O=c1c2ccccc2nc(CN2CCN(c3ncccn3)CC2)n1Cc1ccccc1] | na | na | ND | 73 | 21 |
| B-33 | 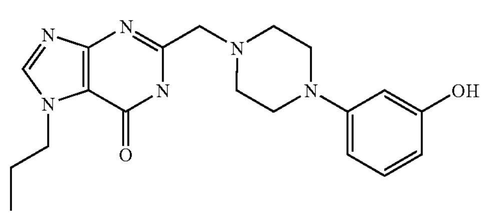 [SMILES: CCCn1cnc2nc(CN3CCN(c4cccc(O)c4)CC3)[nH]c(=O)c21] | 11 | ND | ND | 31 | active |

TABLE 2-continued

| | | D4.4(h) | | | | |
|---|---|---|---|---|---|---|
| No. | Structure | Competitive Binding, % at 5 mcM | GTPgammaS$^{35}$ Cellular Assay, Agonist Response, % | D4/D2 Selectivity | PDE5 % inhibition at 50 mcM | IC50, $10^{-6}$ M |
| B-43 | [structure: 7-chloro-quinazolinone with CH2-piperazine-(3-ethoxypyridin-2-yl)] | ND | ND | ND | 26 | active |
| B-82 | [structure: quinazolinone with CH2-tetrahydropyridine-pyridyl] | 12 | ND | ND | Problems with solubility | Problems with solubility |
| 409 | [structure: purinone with CH2-piperazine-(pyridin-2-yl)] | 8 | ND | ND | 24 | active |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LIST OF REFERENCES CITED

Alcantara, A. G. 1999, J. Sex Marital Ther., 25:125-129
Andersson, K. Pharmacol. Rev. 2001, 53, 417-450.
Andrews, R, Cowley, A. J. Drug Safety 1993, 404
Ashton, A. K. Am J Psychiatry. 2004, 161:2133
Balon, R. 1996, J. Sex Marital Ther., 22:290-292
Beavo, J. A. Physiol. Rev. 1998, 75, 725.
Ben Zion, I. Z., Tessler, R., Cohen, L., Lerer, E., Raz, Y., Bachner-Melman, R., Gritsenko, I., Nemanov, L., Zohar, A. H., Belmaker, R. H., Benjamin, J., Ebstein, R. P. 2006, Mol. Psychiatry, 11:782-786
Brioni, J. D., Moreland, R. B., Cowart, M., Hsieh, G. C., Stewart, A. O., Hedlund, P., Donnelly-Roberts, D. L., Nakane, M., Lynch, J. J., III, Kolasa, T., Polakowski, J. S., Osinski, M. A., Marsh, K., Andersson, K. E., Sullivan, J. P. Proc. Natl. Acad. Sci. U.S.A. 2004, 101, 6758.
Burnett, A. L. Nitric oxide in the penis; physiology and pathology. Journal of Urology 1997, 157, 320-324.
Corbin, J. D., Francis, S. H. Cyclic GMP phosphodiesterase-5: target of sildenafil. Journal of Biological Chemistry 1999, 274, 13729-13732.
Corbin, J. D., Francis, S. H., Webb, D. J. Phosphodiesterase type 5 as a pharmacologic target in erectile dysfunction. Urology 2002, 60, 4-11.
Cowart, M., Latshaw, S. P., Bhatia, P., Daanen, J. F., Rohde, J., Nelson, S. L., Patel, M., Kolasa, T., Nakane, M., Uchic, M. E., Miller, L. N., Terranova, M. A., Chang, R., Donnelly-Roberts, D. L., Namovic, M. T., Hollingsworth, P. R., Martino, B., Lynch, J. J., Sullivan, J., Hsieh, G. C., Moreland, R. B., Brioni, J. D., Stewart, A. O. J. Med. Chem. 2004, 47(15), 3853-64.
Damis, M., Patel, Y., Simpson, G. M. Prim. Care Companion J. Clin. Psychiatry 1999, 1:184-187
Dumaitre, B., Dodic, N. J. Med. Chem. 1996, 39, 1635.
Evans L. E., Bett, J. H., Cox, J. R., Dupois, J. P., Van Hees, T. Prog. Neuropsychopharmacol. 1980, 4:293-302
Francis, S. H., Corbin, J. D. Methods Enzym. 1988, 159, 722.
Hyttel, J. Prog. Neuro-Psychopharmacol. Biol. Psychiat. 1982, 6:277-95
Giuliano, F., Allard, J. 2001, Int. J. Impot. Res., 13 Suppl. 3:S18-28
Gundlach, A. L., Largent, B. L., Snyder, S. H. Life Sciences 1984, 35:1981-1988
Jarvis, K. R., Tiberi, M., Silvia, C., Gingrich, J. A. and Caron, M. G. J. Receptor Research 1973, 13(1-4): 573-590

Melis, M. & Argiolas, A. *Neurosci. Biobehav. Rev.* 1995, 19, 19-38.
Melis, M. R., Succu, S., Sanna, F., Melis, T., Mascia, M. S., Enghard-Gueiffier, C., Hubner, H., Gmeiner, P., Gueiffier, A., Argiolas, A. *Eur. J. Neurosci.* 2006, 24:2021-2030
Missale, C., Nash, S., Robinson, S., Jaber, M. & Caron, M. *Physiol. Rev.* 1998, 78, 189-225
Missale, C., Nash, S., Robinson, S., Jaber, M. & Caron, M. Physiol. Rev. 1998, 78, 189-225
Modell, J. G., May, R. S., Katholi, C. R. J. Sex Marital Ther. 2000, 26:231-240
Moreland, R. B., Goldstein, I., Traish, A. Life Sci. 1995, 62, PL309.
Moreland, R. B., Hsieh, G., Nakane, M., Brioni, J. D. J. Pharm. Exper. Therap. 2001, 296, 225.
Moreland, R. B., Patel, M., Hsieh, G. C., Wetter, J. M., Marsh, K., Brioni, J. D. *Pharmacol. Biochem. Behav.* 2005, 82:140-147
Nakane, M., Cowart, M. D., Hsieh, G. C., Miller, L., Uchic, M. E., Chang, R., Terranova, M. A., Donnely-Roberts, D. L., Namovic, M. T., Miller, T. R., Wetter, J. M., Marsh, K., Stewart, A. O., Brioni, J. D., Moreland, R. B. *Neuropharmacology* 2005, 49:112-121
Rotella D P. Phosphodiesterase 5 inhibitors: current status and potential applications. Nat Rev Drug Discov. 2002 September; 1(9):674-82.
Stimmel, G. L., Gutierrez, M. A. 2006, CNS Spectr., 11:24-30
Takase, Y., Saeki, T., Watanabe, N., Adachi, H., Souda, S., Saito, I. J. Med. Chem. 1993, 37, 2104.
Takase, Y., Saeki, T., Fujimoto, M., Saito, I. J. Med. Chem. 1994, 36, 3765.
Terret, N. K., Bell, A. S., Brown, D., Ellis, P. Bioorg. Med. Chem. Lett. 1996, 6, 1819.
Ukida, T., Nakamura, Y., Kubo, A., Yamamoto, Y., Takahashi, M., Kotera, J., Ikeo, T. J. Med. Chem. 1999, 42, 1293
Ukida, T., Nakamura, Y., Kubo, A., Yamamoto, Y., Moritani, Y., Saruta, K., Higashijima, T., Kotera, J., Takagi, M., Kikkawa, K., Omori, K. J. Med. Chem. 2001, 44, 2204.
Van Tol H. H., Bunzow, J. R., Guan, H. C., Sunahara, R. K., Seeman, P., Niznik, H. B., Civelli, O. Nature 1991, 350: 610-614
Van Tol H. H., Wu, C. M., Guan, H. C., Ohara, K., Bunzow, J. R., Civelli, O., Kennedy, J., Seeman, P., Niznik, H. B., Jovanovic, V. Nature 1992, 358: 149-152
Watanabe, N., Adachi, H., Takase, Y., Ozaki, H., Matsukura, M., Miyazaki, K., Kabasawa, Y. J. Med. Chem. 2000, 43, 2523.
Wolters, J. P., Hellstrom, W. J. Rev. Urol. 2006, 8, Suppl. 4:S18-25

What is claimed is:

1. A compound having the Formula I:

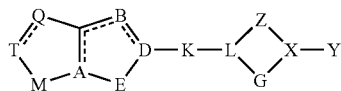

Formula I or a pharmaceutically acceptable salt thereof,
wherein:
the dashed line denotes a saturated or non-saturated bond;
M is —CRb=CRc—;
Q is CRd;
T is CRa;
A is C;
B is N;
D is =C—NR$_2$—;
E is C=O;
K is methylene;
L is N;
Z is —CR$_6$R$_7$—CR$_8$R$_9$—;
G is —CR$_{10}$R$_{11}$—CR$_{12}$R$_{13}$—;
X is N;
Y has the general formula II:

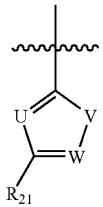

Formula II wherein:
U is CR$_{20}$;
V is —CR$_{24}$=CR$_{23}$—;
W is CR$_{22}$;
R$_6$-R$_{13}$ are each independently selected from the group consisting of hydrogen, alkyl, alkenyl, or cycloalkyl;
R$_{21}$ is hydroxy;
R$_2$, R$_{20}$ and R$_{22}$-R$_{24}$ are each hydrogen; and
Ra-Rd are each independently selected from the group consisting of hydrogen, alkyl, hydroxy, alkoxy, and halide, each being substituted or non-substituted.

2. A pharmaceutical composition comprising the compound of claim 1 and a pharmaceutically acceptable carrier.

3. A process of preparing the compound of claim 1, the process comprising:
reacting a compound having the general Formula:

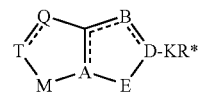

wherein R* is a leaving group,
and a compound having the general Formula:

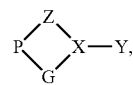

wherein P is NH,
thereby obtaining the compound having said Formula I.

* * * * *